(12) United States Patent
Alden et al.

(10) Patent No.: US 8,296,918 B2
(45) Date of Patent: Oct. 30, 2012

(54) METHOD OF MANUFACTURING A FLUID SAMPLING DEVICE WITH IMPROVED ANALYTE DETECTING MEMBER CONFIGURATION

(75) Inventors: Don Alden, Sunnyvale, CA (US); Travis Marsot, Mountain View, CA (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 169 days.

(21) Appl. No.: 12/861,514

(22) Filed: Aug. 23, 2010

(65) Prior Publication Data

US 2011/0016691 A1    Jan. 27, 2011

Related U.S. Application Data

(62) Division of application No. 11/028,952, filed on Jan. 3, 2005, now Pat. No. 7,822,454.

(60) Provisional application No. 60/533,997, filed on Dec. 31, 2003, provisional application No. 60/533,969, filed on Dec. 31, 2003.

(51) Int. Cl.
*B21D 53/00* (2006.01)
*A61B 5/00* (2006.01)

(52) U.S. Cl. .................. 29/407.01; 29/407.05; 29/458; 29/469; 600/583

(58) Field of Classification Search .............. 600/181, 600/583; 29/407.01, 407.05, 458, 469
See application file for complete search history.

(56) References Cited

U.S. PATENT DOCUMENTS

| 2,061 A | 4/1841 | Osdel | 606/182 |
|---|---|---|---|
| 55,620 A | 6/1866 | Capewell | 606/181 |
| 1,135,465 A | 4/1915 | Pollock | 606/181 |
| 1,733,847 A | 10/1929 | Wilmot | 292/332 |
| 2,258,857 A | 10/1941 | McCann | 601/81 |
| 2,628,319 A | 2/1953 | Vang | 310/15 |
| 2,714,890 A | 8/1955 | Alfred | 606/169 |
| 2,763,935 A | 9/1956 | Whaley | 33/511 |
| 2,801,633 A | 8/1957 | Ehrlich | 606/181 |
| 2,880,876 A | 4/1959 | Dujardin | 210/523 |
| 3,046,987 A | 7/1962 | Ehrlich | 128/314 |
| 3,030,959 A | 9/1962 | Grunert | 128/329 |
| 3,086,288 A | 4/1963 | Balamuth | 30/277.4 |
| 3,090,384 A | 5/1963 | Baldwin et al. | 604/272 |
| 3,208,452 A | 9/1965 | Stern | 606/182 |
| 3,358,689 A | 12/1967 | Higgins | 128/329 |
| 3,412,729 A | 11/1968 | Smith, Jr. | 128/2.05 |
| 3,448,307 A | 6/1969 | Rudolph | 310/23 |
| 3,494,358 A | 2/1970 | Grossenbacher | 128/218 |
| 3,620,209 A | 11/1971 | Kravitz | 601/79 |
| 3,626,929 A | 12/1971 | Sanz | 128/2 R |

(Continued)

FOREIGN PATENT DOCUMENTS

DE        4344452        6/1995

(Continued)

OTHER PUBLICATIONS

Machine translation of DE 10053974 pp. 1-4, provided by epo.org.

(Continued)

*Primary Examiner* — Jermie Cozart
(74) *Attorney, Agent, or Firm* — Paul Davis; Goodwin Procter LLP

(57) ABSTRACT

An assembly is described that combines blood chemical analysis with lancing in a single multiple-test disposable cartridge. The penetrating members can be assembled and sterilized without damaging the analytical chemistry, and the functioning of the present radical disc cartridge mechanism is not substantially modified.

7 Claims, 15 Drawing Sheets

U.S. PATENT DOCUMENTS

| | | | |
|---|---|---|---|
| 3,628,026 A | 12/1971 | Cronin | 250/214.1 |
| 3,665,672 A | 5/1972 | Speelman | 53/435 |
| 3,673,475 A | 6/1972 | Britton | 318/122 |
| 3,712,293 A | 1/1973 | Mielke, Jr. | 128/2 G |
| 3,734,812 A | 5/1973 | Yazawa | 428/107 |
| 3,742,954 A | 7/1973 | Strickland | 128/302 |
| 3,780,960 A | 12/1973 | Tokuno | 242/555.2 |
| 3,832,776 A | 9/1974 | Sawyer | 30/272 |
| 3,836,148 A | 9/1974 | Manning | 273/368 |
| 3,851,543 A | 12/1974 | Krom | 74/493 |
| 3,853,010 A | 12/1974 | Christen | 73/864.24 |
| 3,924,818 A | 12/1975 | Pfeifle | 242/364.7 |
| 3,938,526 A | 2/1976 | Anderson | 128/303.1 |
| 3,953,172 A | 4/1976 | Shapiro | 23/230 |
| 3,971,365 A | 7/1976 | Smith | 128/2.17 |
| 4,057,394 A | 11/1977 | Genshaw | 23/230 |
| 4,077,406 A | 3/1978 | Sandhage | 604/61 |
| 4,109,655 A | 8/1978 | Chaconac | 128/253 |
| 4,139,011 A | 2/1979 | Benoit | 606/182 |
| 4,154,228 A | 5/1979 | Feldstein | 606/169 |
| 4,168,130 A | 9/1979 | Barth | 404/99 |
| 4,184,486 A | 1/1980 | Papa | 600/373 |
| 4,190,420 A | 2/1980 | Covington | 422/63 |
| 4,191,193 A | 3/1980 | Seo | 600/488 |
| 4,193,690 A | 3/1980 | Levenson | 356/301 |
| 4,203,446 A | 5/1980 | Hofert | 606/182 |
| 4,207,870 A | 6/1980 | Eldridge | 128/766 |
| 4,223,674 A | 9/1980 | Fluent | 604/504 |
| 4,224,125 A | 9/1980 | Nakamura | 204/195 B |
| 4,224,949 A | 9/1980 | Scott | 128/734 |
| 4,230,118 A | 10/1980 | Holman et al. | 128/314 |
| 4,240,439 A | 12/1980 | Abe | 600/412 |
| 4,254,083 A | 3/1981 | Columbus | 422/55 |
| 4,258,001 A | 3/1981 | Pierce | 422/56 |
| 4,259,653 A | 3/1981 | McGonigal | 310/15 |
| 4,299,230 A | 11/1981 | Kubota | 600/300 |
| 4,301,412 A | 11/1981 | Hill | 324/442 |
| 4,321,397 A | 3/1982 | Nix | 548/366 |
| 4,338,174 A | 7/1982 | Tamura | 204/195 |
| 4,340,669 A | 7/1982 | Bauer | 435/14 |
| 4,350,762 A | 9/1982 | De Luca | 435/10 |
| 4,353,984 A | 10/1982 | Yamada | 435/14 |
| 4,356,826 A | 11/1982 | Kubota | 600/300 |
| 4,360,016 A | 11/1982 | Sarrine | 128/763 |
| 4,388,922 A | 6/1983 | Telang | 604/319 |
| 4,391,905 A | 7/1983 | Bauer | 435/14 |
| 4,391,906 A | 7/1983 | Bauer | 435/14 |
| 4,392,933 A | 7/1983 | Nakamura | 204/403.14 |
| 4,394,512 A | 7/1983 | Batz | 548/365 |
| 4,397,556 A | 8/1983 | Muller | 356/301 |
| 4,407,008 A | 9/1983 | Schmidt | 356/301 |
| 4,411,266 A | 10/1983 | Cosman | 128/303.18 |
| 4,414,975 A | 11/1983 | Ryder | 128/314 |
| 4,418,037 A | 11/1983 | Katsuyama | 422/56 |
| 4,420,564 A | 12/1983 | Tsuji | 435/288 |
| 4,425,039 A | 1/1984 | Grant | 356/35.5 |
| 4,426,451 A | 1/1984 | Columbus | 436/518 |
| 4,426,884 A | 1/1984 | Polchaninoff | 73/172 |
| 4,440,301 A | 4/1984 | Intengan | 206/456 |
| 4,442,836 A | 4/1984 | Meinecke | 128/314 |
| 4,442,972 A | 4/1984 | Sahay | 236/1 EA |
| 4,449,529 A | 5/1984 | Burns | 606/182 |
| 4,462,405 A | 7/1984 | Ehrlich | 606/182 |
| 4,469,110 A | 9/1984 | Slama | 128/770 |
| 4,517,978 A | 5/1985 | Levin | 128/314 |
| 4,518,384 A | 5/1985 | Tarello | 604/61 |
| 4,523,994 A | 6/1985 | Shono | 549/352 |
| 4,535,769 A | 8/1985 | Burns | 128/314 |
| 4,535,773 A | 8/1985 | Yoon | 606/185 |
| 4,537,197 A | 8/1985 | Hulka | 128/633 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,561,445 A | 12/1985 | Berke | 128/642 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,586,819 A | 5/1986 | Tochigi | 356/301 |
| 4,586,926 A | 5/1986 | Osborne | 604/272 |
| 4,590,411 A | 5/1986 | Kelly | 318/687 |
| 4,595,479 A | 6/1986 | Kimura | 204/294 |
| 4,600,014 A | 7/1986 | Beraha | 128/754 |
| 4,603,209 A | 7/1986 | Tsien | 549/352 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,627,445 A | 12/1986 | Garcia | 600/583 |
| 4,637,393 A | 1/1987 | Ray | 128/305 |
| 4,637,403 A | 1/1987 | Garcia | 600/583 |
| 4,643,189 A | 2/1987 | Mintz | 128/314 |
| 4,648,408 A | 3/1987 | Hutcheson | 128/770 |
| 4,648,714 A | 3/1987 | Benner | 356/301 |
| 4,653,511 A | 3/1987 | Goch | 128/763 |
| 4,653,513 A | 3/1987 | Dombrowski | 600/578 |
| 4,655,225 A | 4/1987 | Dahne | 600/316 |
| 4,661,768 A | 4/1987 | Carusillo | 324/678 |
| 4,666,438 A | 5/1987 | Raulerson | 604/272 |
| 4,676,244 A | 6/1987 | Enstrom | 128/314 |
| 4,677,979 A | 7/1987 | Burns | 128/314 |
| 4,678,277 A | 7/1987 | Delhaye | 356/301 |
| 4,682,892 A | 7/1987 | Chawla | 356/353 |
| 4,702,594 A | 10/1987 | Grant | 356/35.5 |
| 4,711,245 A | 12/1987 | Higgins | 128/635 |
| 4,712,460 A | 12/1987 | Allen | 83/208 |
| 4,712,548 A | 12/1987 | Enstrom | 128/314 |
| 4,714,462 A | 12/1987 | DiDomenico | 604/67 |
| 4,715,374 A | 12/1987 | Maggio | 128/314 |
| 4,731,330 A | 3/1988 | Hill J | 436/16 |
| 4,731,726 A | 3/1988 | Allen, III | 600/300 |
| 4,734,360 A | 3/1988 | Phillips | 435/25 |
| 4,735,203 A | 4/1988 | Ryder | 128/314 |
| 4,737,458 A | 4/1988 | Batz | 435/28 |
| 4,750,489 A | 6/1988 | Berkman | 606/166 |
| 4,753,776 A | 6/1988 | Hillman | 422/101 |
| 4,756,884 A | 7/1988 | Hillman | 422/73 |
| 4,757,022 A | 7/1988 | Shults | 204/403.05 |
| 4,758,323 A | 7/1988 | Davis | 204/403 |
| 4,774,192 A | 9/1988 | Teriniello | 436/530 |
| 4,784,486 A | 11/1988 | Van Wagenen | 356/301 |
| 4,787,398 A | 11/1988 | Garcia | 600/583 |
| 4,790,979 A | 12/1988 | Teriniello | 422/56 |
| 4,794,926 A | 1/1989 | Munsch et al. | 606/183 |
| 4,797,283 A | 1/1989 | Allen | 424/443 |
| 4,814,142 A | 3/1989 | Gleisner | 422/56 |
| 4,814,661 A | 3/1989 | Ratzlaff et al. | 310/328 |
| 4,817,603 A | 4/1989 | Turner | 606/182 |
| 4,818,493 A | 4/1989 | Coville | 422/102 |
| 4,820,010 A | 4/1989 | Scifres | 385/43 |
| 4,820,399 A | 4/1989 | Senda | 204/403 |
| 4,823,806 A | 4/1989 | Bajada | 600/557 |
| 4,824,639 A | 4/1989 | Hildenbrand | 422/56 |
| RE32,922 E | 5/1989 | Levin | 128/314 |
| 4,825,711 A | 5/1989 | Jensen | 73/865.8 |
| 4,827,763 A | 5/1989 | Bourland | 73/172 |
| 4,829,011 A | 5/1989 | Gibbons | 436/512 |
| 4,830,959 A | 5/1989 | McNeil | 435/53 |
| 4,836,904 A | 6/1989 | Armstron et al. | 204/294 |
| 4,840,893 A | 6/1989 | Hill | 435/6 |
| 4,844,095 A | 7/1989 | Chiodo | 128/314 |
| 4,845,392 A | 7/1989 | Mumbower | 310/14 |
| 4,850,973 A | 7/1989 | Jordan | 604/157 |
| 4,857,274 A | 8/1989 | Simon | 422/72 |
| 4,868,129 A | 9/1989 | Gibbons | 436/179 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,877,026 A | 10/1989 | de Laforcade | 128/305 |
| 4,882,013 A | 11/1989 | Turner | 204/1 |
| 4,883,055 A | 11/1989 | Merrick | 128/633 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |

| Patent No. | Kind | Date | Inventor | Class |
|---|---|---|---|---|
| 4,895,156 | A | 1/1990 | Schulze | 600/342 |
| 4,897,173 | A | 1/1990 | Nankai | 204/403 |
| 4,900,424 | A | 2/1990 | Birth | 204/409 |
| 4,900,666 | A | 2/1990 | Phillips | 435/25 |
| 4,911,794 | A | 3/1990 | Parce | 204/1 T |
| 4,920,977 | A | 5/1990 | Haynes | 128/770 |
| 4,924,879 | A | 5/1990 | O'brien | 600/583 |
| 4,935,346 | A | 6/1990 | Phillips | 435/14 |
| 4,938,218 | A | 7/1990 | Goodman | 128/633 |
| 4,940,468 | A | 7/1990 | Petillo | 606/170 |
| 4,944,304 | A | 7/1990 | Nishina | 128/667 |
| 4,945,045 | A | 7/1990 | Forrest | 435/25 |
| 4,946,795 | A | 8/1990 | Gibbons | 436/179 |
| 4,948,727 | A | 8/1990 | Cass | 435/18 |
| 4,948,961 | A | 8/1990 | Hillman | 250/252.1 |
| 4,952,373 | A | 8/1990 | Sugarman | 422/99 |
| 4,952,515 | A | 8/1990 | Gleisner | 436/169 |
| 4,953,552 | A | 9/1990 | DeMarzo | 128/635 |
| 4,953,976 | A | 9/1990 | Adler-Golden | 356/301 |
| 4,963,498 | A | 10/1990 | Hillman | 436/69 |
| 4,966,581 | A | 10/1990 | Landau | 604/72 |
| 4,966,646 | A | 10/1990 | Zdeblick | 156/633 |
| 4,966,671 | A | 10/1990 | Nylander | 204/153.14 |
| 4,975,581 | A | 12/1990 | Robinson | 250/339 |
| 4,976,724 | A | 12/1990 | Nieto | 606/167 |
| 4,977,910 | A | 12/1990 | Miyahara | 134/7 |
| 4,983,178 | A | 1/1991 | Schnell | 606/181 |
| 4,984,085 | A | 1/1991 | Landowski | 358/213 |
| 4,990,154 | A | 2/1991 | Brown | 606/182 |
| 4,995,402 | A | 2/1991 | Smith | 600/584 |
| 4,999,582 | A | 3/1991 | Parks | 324/438 |
| 5,001,054 | A | 3/1991 | Wagner | 435/14 |
| 5,001,873 | A | 3/1991 | Rufin | 451/39 |
| 5,004,923 | A | 4/1991 | Hillman | 250/341 |
| 5,010,772 | A | 4/1991 | Bourland | 73/862.04 |
| 5,010,774 | A | 4/1991 | Kikuo et al. | 73/862.04 |
| 5,014,718 | A | 5/1991 | Mitchen | 128/771 |
| 5,019,974 | A | 5/1991 | Beckers | 364/413.02 |
| 5,026,388 | A | 6/1991 | Ingalz | 606/182 |
| D318,331 | S | 7/1991 | Phillips | D24/169 |
| 5,028,142 | A | 7/1991 | Ostoich | 366/273 |
| 5,029,583 | A | 7/1991 | Meserol | 600/316 |
| 5,035,704 | A | 7/1991 | Lambert | 606/182 |
| 5,039,617 | A | 8/1991 | McDonald | 436/69 |
| 5,043,143 | A | 8/1991 | Shaw | 422/65 |
| 5,046,496 | A | 9/1991 | Betts | 600/352 |
| 5,047,044 | A | 9/1991 | Smith | 606/182 |
| 5,049,373 | A | 9/1991 | Ballou | 549/499 |
| 5,049,487 | A | 9/1991 | Phillips | 435/4 |
| 5,054,487 | A | 10/1991 | Clarke | 128/633 |
| 5,054,499 | A | 10/1991 | Swierczek | 128/770 |
| 5,057,082 | A | 10/1991 | Burchette, Jr. | 604/164 |
| 5,057,277 | A | 10/1991 | Mauze | 422/56 |
| 5,059,394 | A | 10/1991 | Phillips | 422/68.1 |
| 5,059,789 | A | 10/1991 | Salcudean | 250/206.1 |
| 5,060,174 | A | 10/1991 | Gross | 702/139 |
| 5,062,898 | A | 11/1991 | McDermott | 134/7 |
| 5,064,411 | A | 11/1991 | Gordon, III | 604/48 |
| 5,070,874 | A | 12/1991 | Barnes | 128/633 |
| 5,070,886 | A | 12/1991 | Mitchen | 128/771 |
| 5,074,872 | A | 12/1991 | Brown | 606/182 |
| 5,077,017 | A | 12/1991 | Gorin | 422/100 |
| 5,077,199 | A | 12/1991 | Basagni | 435/14 |
| 5,080,865 | A | 1/1992 | Leiner | 422/68.1 |
| 5,086,229 | A | 2/1992 | Rosenthal | 250/341 |
| 5,089,112 | A | 2/1992 | Skotheim | 204/403 |
| 5,092,842 | A | 3/1992 | Bechtold | 604/135 |
| 5,094,943 | A | 3/1992 | Siedel | 435/25 |
| 5,096,669 | A | 3/1992 | Lauks | 204/403.02 |
| 5,097,810 | A | 3/1992 | Fishman | 600/556 |
| 5,100,427 | A | 3/1992 | Crossman | 606/182 |
| 5,100,428 | A | 3/1992 | Mumford | 606/182 |
| 5,104,380 | A | 4/1992 | Holman | 604/117 |
| 5,104,382 | A | 4/1992 | Brinkerhoff et al. | 604/164.12 |
| 5,104,619 | A | 4/1992 | Castro | 422/56 |
| 5,104,813 | A | 4/1992 | Besemer | 436/179 |
| 5,107,764 | A | 4/1992 | Gasparrini | 101/425 |
| 5,108,564 | A | 4/1992 | Szuminsky | 204/153.12 |
| 5,108,889 | A | 4/1992 | Smith | 435/4 |
| 5,116,759 | A | 5/1992 | Klainer | 435/288 |
| 5,120,420 | A | 6/1992 | Nankai et al. | 204/403 |
| 5,122,244 | A | 6/1992 | Hoenes | 204/153 |
| 5,126,034 | A | 6/1992 | Carter | 204/403 |
| 5,128,015 | A | 7/1992 | Szuminsky | 204/403 |
| 5,128,171 | A | 7/1992 | Gleisner | 427/2 |
| 5,132,801 | A | 7/1992 | Yamano | 358/213 |
| 5,133,730 | A | 7/1992 | Biro | 606/182 |
| 5,135,719 | A | 8/1992 | Hillman | 422/101 |
| 5,139,685 | A | 8/1992 | Castro | 210/767 |
| 5,140,161 | A | 8/1992 | Hillman | 250/341 |
| 5,141,868 | A | 8/1992 | Shanks | 435/288 |
| 5,144,139 | A | 9/1992 | Hillman | 250/341 |
| 5,145,565 | A | 9/1992 | Kater | 600/341 |
| 5,146,091 | A | 9/1992 | Knudson | 250/341.6 |
| 5,152,296 | A | 10/1992 | Simons | 128/670 |
| 5,152,775 | A | 10/1992 | Ruppert | 606/182 |
| 5,153,671 | A | 10/1992 | Miles | 356/301 |
| 5,156,611 | A | 10/1992 | Haynes | 606/181 |
| 5,162,525 | A | 11/1992 | Masilamani | 549/352 |
| 5,163,442 | A | 11/1992 | Ono | 128/760 |
| 5,164,598 | A | 11/1992 | Hillman | 250/341 |
| 5,167,619 | A | 12/1992 | Wuchinich | 604/22 |
| 5,170,364 | A | 12/1992 | Gross | 702/139 |
| 5,174,726 | A | 12/1992 | Findlay | 417/205 |
| D332,490 | S | 1/1993 | Brown | D24/146 |
| 5,178,142 | A | 1/1993 | Harjunmaa | 128/633 |
| 5,179,005 | A | 1/1993 | Phillips | 435/14 |
| 5,181,910 | A | 1/1993 | Scanlon | 604/67 |
| 5,181,914 | A | 1/1993 | Zook | 604/307 |
| 5,183,042 | A | 2/1993 | Harjunmaa | 128/633 |
| 5,185,256 | A | 2/1993 | Nankai | 435/174 |
| 5,187,100 | A | 2/1993 | Matzinger | 436/16 |
| 5,188,118 | A | 2/1993 | Terwilliger | 600/566 |
| 5,189,751 | A | 3/1993 | Giuliani | 15/22.1 |
| 5,192,415 | A | 3/1993 | Yoshioka | 204/403 |
| 5,194,391 | A | 3/1993 | Mauze | 436/166 |
| 5,196,025 | A | 3/1993 | Ranalletta | 606/182 |
| 5,201,324 | A | 4/1993 | Swierczek | 128/770 |
| 5,205,920 | A | 4/1993 | Oyama | 204/403 |
| 5,209,028 | A | 5/1993 | McDermott | 51/426 |
| 5,211,652 | A | 5/1993 | Derbyshire | 606/182 |
| 5,212,879 | A | 5/1993 | Biro | 29/437 |
| 5,215,587 | A | 6/1993 | McConnellogue | 118/699 |
| 5,216,597 | A | 6/1993 | Beckers | 364/413.02 |
| 5,217,476 | A | 6/1993 | Wishinsky | 606/167 |
| 5,217,480 | A | 6/1993 | Haber | 606/182 |
| 5,218,966 | A | 6/1993 | Yamasawa | 600/499 |
| 5,222,504 | A | 6/1993 | Solomon | 600/557 |
| 5,228,972 | A | 7/1993 | Osaka | 204/415 |
| 5,229,282 | A | 7/1993 | Yoshioka | 435/177 |
| 5,230,866 | A | 7/1993 | Shartle | 422/103 |
| 5,231,993 | A | 8/1993 | Haber | 128/770 |
| 5,241,969 | A | 9/1993 | Carson | 600/566 |
| 5,247,932 | A | 9/1993 | Chung | 128/633 |
| 5,249,583 | A | 10/1993 | Mallaby | 600/567 |
| 5,250,066 | A | 10/1993 | Lambert | 606/181 |
| 5,251,126 | A | 10/1993 | Kahn | 364/413.11 |
| 5,253,656 | A | 10/1993 | Rincoe | 128/782 |
| 5,256,998 | A | 10/1993 | Becker | 335/229 |
| 5,264,103 | A | 11/1993 | Yoshioka | 204/403 |
| 5,264,105 | A | 11/1993 | Gregg | 204/403 |
| 5,264,106 | A | 11/1993 | McAleer | 204/403 |
| 5,266,179 | A | 11/1993 | Nankai | 204/401 |
| 5,266,359 | A | 11/1993 | Spielvogel | 427/388.4 |
| D342,573 | S | 12/1993 | Cerola | D24/147 |
| 5,267,974 | A | 12/1993 | Lambert | 604/195 |
| 5,272,087 | A | 12/1993 | El Murr | 435/291 |
| 5,277,181 | A | 1/1994 | Mendelson | 128/633 |
| 5,279,294 | A | 1/1994 | Anderson | 600/322 |
| 5,279,791 | A | 1/1994 | Aldrich | 422/58 |
| 5,282,822 | A | 2/1994 | Macors | 606/182 |
| 5,286,362 | A | 2/1994 | Hoenes | 204/403 |
| 5,286,364 | A | 2/1994 | Yacynych | 204/418 |
| 5,288,636 | A | 2/1994 | Pollmann | 435/288 |
| 5,294,261 | A | 3/1994 | McDermott | 134/7 |
| 5,296,378 | A | 3/1994 | Sakata | 436/63 |
| 5,300,779 | A | 4/1994 | Hillman | 250/341 |
| 5,304,192 | A | 4/1994 | Crouse | 606/181 |

| Patent | Date | Inventor | Class |
|---|---|---|---|
| 5,304,193 A | 4/1994 | Zhadanov | 606/182 |
| 5,304,347 A | 4/1994 | Mann | 422/67 |
| 5,304,468 A | 4/1994 | Phillips | 435/14 |
| 5,306,623 A | 4/1994 | Kiser | 435/14 |
| 5,307,263 A | 4/1994 | Brown | 600/301 |
| 5,312,590 A | 5/1994 | Gunasingham | 422/56 |
| 5,314,441 A | 5/1994 | Cusack | 606/182 |
| 5,314,442 A | 5/1994 | Morita | 606/182 |
| 5,315,793 A | 5/1994 | Peterson | 451/2 |
| 5,316,012 A | 5/1994 | Siegal | 128/744 |
| 5,318,583 A | 6/1994 | Rabenau | 606/182 |
| 5,318,584 A | 6/1994 | Lange | 606/182 |
| 5,320,607 A | 6/1994 | Ishibashi | 604/115 |
| 5,320,808 A | 6/1994 | Holen | 422/64 |
| 5,324,302 A | 6/1994 | Crouse | 606/181 |
| 5,324,303 A | 6/1994 | Strong | 606/182 |
| 5,330,634 A | 7/1994 | Wong | 205/777.5 |
| 5,332,479 A | 7/1994 | Uenoyama | 204/153.12 |
| 5,341,206 A | 8/1994 | Pittaro | 356/301 |
| 5,342,382 A | 8/1994 | Brinkerhoff | 606/184 |
| 5,344,703 A | 9/1994 | Kovar | 428/312.6 |
| 5,350,392 A | 9/1994 | Purcell | 606/182 |
| 5,352,351 A | 10/1994 | White | 204/406 |
| 5,354,287 A | 10/1994 | Wacks | 604/232 |
| 5,354,447 A | 10/1994 | Uenoyama | 204/403 |
| 5,356,420 A | 10/1994 | Czernecki | 606/182 |
| 5,360,410 A | 11/1994 | Wacks | 604/232 |
| 5,365,699 A | 11/1994 | Armstrong | 451/7 |
| 5,366,469 A | 11/1994 | Steg | 606/182 |
| 5,366,470 A | 11/1994 | Ramel | 606/183 |
| 5,366,609 A | 11/1994 | White | 204/403 |
| 5,368,047 A | 11/1994 | Suzuki | 600/578 |
| 5,370,509 A | 12/1994 | Golding | 417/423.1 |
| 5,371,687 A | 12/1994 | Holmes | 364/514 |
| 5,372,135 A | 12/1994 | Mendelson | 600/322 |
| 5,375,397 A | 12/1994 | Ferrand | 54/66 |
| 5,378,628 A | 1/1995 | Graetzel | 435/288 |
| 5,382,346 A | 1/1995 | Uenoyama | 204/403 |
| 5,383,885 A | 1/1995 | Bland | 606/182 |
| 5,389,534 A | 2/1995 | von Gentzkow | 435/180 |
| 5,390,450 A | 2/1995 | Goenka | 451/39 |
| 5,393,903 A | 2/1995 | Gratzel | 556/137 |
| 5,395,339 A | 3/1995 | Talonn | 604/111 |
| 5,395,387 A | 3/1995 | Burns | 606/181 |
| 5,397,334 A | 3/1995 | Schenk | 606/182 |
| 5,401,376 A | 3/1995 | Foos | 204/415 |
| 5,402,798 A | 4/1995 | Swierczek | 128/770 |
| 5,405,283 A | 4/1995 | Goenka | 451/39 |
| 5,405,510 A | 4/1995 | Betts | 205/782 |
| 5,405,511 A | 4/1995 | White | 204/153.1 |
| 5,407,545 A | 4/1995 | Hirose | 204/153.12 |
| 5,407,554 A | 4/1995 | Saurer et al. | 204/403 |
| 5,407,818 A | 4/1995 | Gentzkow | 435/14 |
| 5,409,583 A | 4/1995 | Yoshioka | 204/153.12 |
| 5,409,664 A | 4/1995 | Allen | 422/56 |
| 5,410,059 A | 4/1995 | Fraser | 546/10 |
| 5,415,169 A | 5/1995 | Siczek | 600/427 |
| 5,418,142 A | 5/1995 | Kiser | 435/14 |
| 5,423,847 A | 6/1995 | Strong et al. | 606/182 |
| 5,424,545 A | 6/1995 | Block | 350/343 |
| 5,426,032 A | 6/1995 | Phillips | 435/14 |
| 5,436,161 A | 7/1995 | Bergstrom | 435/291 |
| 5,437,999 A | 8/1995 | Diebold | 435/288 |
| 5,438,271 A | 8/1995 | White | 324/444 |
| 5,443,701 A | 8/1995 | Willner | 204/153 |
| 5,445,920 A | 8/1995 | Saito | 430/311 |
| D362,719 S | 9/1995 | Kaplan | D24/147 |
| 5,453,360 A | 9/1995 | Yu | 435/28 |
| 5,454,828 A | 10/1995 | Schraga | 606/181 |
| 5,456,875 A | 10/1995 | Lambert | 264/328.1 |
| 5,459,325 A | 10/1995 | Hueton | 250/458.1 |
| 5,460,342 A | 10/1995 | Goodman | 600/342 |
| 5,462,533 A | 10/1995 | Daugherty | 604/164 |
| 5,464,418 A | 11/1995 | Schraga | 606/182 |
| 5,465,722 A | 11/1995 | Fort | 600/447 |
| 5,471,102 A | 11/1995 | Becker | 310/50 |
| 5,472,427 A | 12/1995 | Rammler | 604/164.01 |
| 5,474,084 A | 12/1995 | Cunniff | 600/557 |
| 5,476,474 A | 12/1995 | Davis | 606/182 |
| 5,480,387 A | 1/1996 | Gabriel | 604/134 |
| 5,487,748 A | 1/1996 | Marshall | 606/182 |
| D367,109 S | 2/1996 | Ryner | D24/224 |
| 5,490,505 A | 2/1996 | Diab | 600/323 |
| 5,496,274 A | 3/1996 | Graves | 604/86 |
| 5,496,453 A | 3/1996 | Uenoyama | 205/777.5 |
| 5,498,542 A | 3/1996 | Corey | 435/283.1 |
| 5,501,836 A | 3/1996 | Myerson | 42/57 |
| 5,501,893 A | 3/1996 | Laermer | 428/161 |
| 5,507,288 A | 4/1996 | Bocker | 128/633 |
| 5,507,629 A | 4/1996 | Jarvik | 417/423.3 |
| 5,508,171 A | 4/1996 | Walling | 205/777.5 |
| 5,509,410 A | 4/1996 | Hill | 128/637 |
| 5,510,266 A | 4/1996 | Bonner et al. | 436/43 |
| 5,512,159 A | 4/1996 | Yoshioka | 204/403 |
| 5,514,152 A | 5/1996 | Smith | 606/182 |
| 5,515,170 A | 5/1996 | Matzinger | 356/423 |
| 5,518,006 A | 5/1996 | Mawhirt | 128/770 |
| D371,198 S | 6/1996 | Savage | D24/169 |
| 5,524,636 A | 6/1996 | Sarvazyan | 128/774 |
| 5,525,511 A | 6/1996 | D'Costa | 435/287.9 |
| 5,525,518 A | 6/1996 | Lundsgaard | 436/68 |
| 5,526,120 A | 6/1996 | Jina | 356/446 |
| 5,527,333 A | 6/1996 | Nikkels | 606/182 |
| 5,527,334 A | 6/1996 | Kanner | 606/182 |
| 5,529,074 A | 6/1996 | Greenfield | 600/557 |
| 5,540,676 A | 7/1996 | Freiberg | 606/3 |
| 5,540,709 A | 7/1996 | Ramel | 606/183 |
| 5,543,326 A | 8/1996 | Heller | 435/287.9 |
| 5,545,174 A | 8/1996 | Schenk | 606/182 |
| 5,545,291 A | 8/1996 | Smith | 438/107 |
| 5,547,702 A | 8/1996 | Gleisner | 427/2.13 |
| D373,419 S | 9/1996 | Muramatsu | D24/165 |
| 5,554,153 A | 9/1996 | Costello | 606/9 |
| 5,554,166 A | 9/1996 | Lange | 606/182 |
| 5,558,834 A | 9/1996 | Chu | 422/55 |
| 5,562,384 A | 10/1996 | Alvite | 414/226.01 |
| 5,562,696 A | 10/1996 | Nobles | 606/185 |
| 5,563,031 A | 10/1996 | Yu | 435/4 |
| 5,563,042 A | 10/1996 | Phillips | 435/14 |
| 5,569,286 A | 10/1996 | Peckham | 606/181 |
| 5,569,287 A | 10/1996 | Tezuka | 606/182 |
| 5,571,132 A | 11/1996 | Mawhirt | 606/182 |
| 5,575,284 A | 11/1996 | Athan | 600/323 |
| 5,575,403 A | 11/1996 | Charlton | 221/31 |
| 5,575,895 A | 11/1996 | Ikeda | 204/403 |
| 5,582,697 A | 12/1996 | Ikeda | 204/403 |
| 5,584,846 A | 12/1996 | Mawhirt | 606/182 |
| 5,591,139 A | 1/1997 | Lin | 604/264 |
| 5,593,852 A | 1/1997 | Heller | 435/14 |
| 5,599,501 A | 2/1997 | Carey | 422/64 |
| 5,605,837 A | 2/1997 | Karimi | 436/14 |
| D378,612 S | 3/1997 | Clark | D24/169 |
| 5,608,006 A | 3/1997 | Myerson | 525/54.1 |
| 5,609,749 A | 3/1997 | Yamauchi | 205/777.5 |
| 5,611,809 A | 3/1997 | Marshall | 606/181 |
| 5,611,810 A | 3/1997 | Arnold | 606/185 |
| 5,613,978 A | 3/1997 | Harding | 606/181 |
| 5,616,135 A | 4/1997 | Thorne | 604/192 |
| 5,617,851 A | 4/1997 | Lipkovker | 600/573 |
| 5,618,297 A | 4/1997 | Hart | 606/185 |
| 5,620,579 A | 4/1997 | Genshaw | 204/402 |
| 5,620,863 A | 4/1997 | Tomasco | 435/14 |
| 5,624,458 A | 4/1997 | Lipscher | 606/181 |
| 5,624,459 A | 4/1997 | Kortenbach | 606/185 |
| 5,624,537 A | 4/1997 | Turner | 204/403 |
| D379,516 S | 5/1997 | Rutter | D24/146 |
| 5,628,764 A | 5/1997 | Schraga | 606/182 |
| 5,628,765 A | 5/1997 | Morita | 606/182 |
| 5,628,890 A | 5/1997 | Carter | 204/403 |
| 5,628,961 A | 5/1997 | Davis | 422/63 |
| 5,630,828 A | 5/1997 | Mawhirt | 606/187 |
| 5,630,986 A | 5/1997 | Charlton | 422/64 |
| 5,632,410 A | 5/1997 | Moulton | 221/79 |
| 5,640,954 A | 6/1997 | Pfeiffer | 128/635 |
| D381,591 S | 7/1997 | Rice | D10/81 |
| 5,643,306 A | 7/1997 | Schraga | 606/182 |
| 5,643,308 A | 7/1997 | Markman | 606/187 |
| 5,645,555 A | 7/1997 | Davis | 606/182 |

| Patent No. | Date | Inventor | Class |
|---|---|---|---|
| 5,647,851 A | 7/1997 | Pokras | 604/131 |
| 5,650,062 A | 7/1997 | Ikeda | 205/778 |
| 5,653,863 A | 8/1997 | Genshaw | 205/777.5 |
| 5,657,760 A | 8/1997 | Ying | 128/660.03 |
| 5,658,444 A | 8/1997 | Black | 204/415 |
| 5,660,791 A | 8/1997 | Brenneman | 422/58 |
| D383,550 S | 9/1997 | Larson | D24/225 |
| 5,662,127 A | 9/1997 | De Vaughn | 128/765 |
| 5,662,672 A | 9/1997 | Pambianchi | 606/181 |
| 5,666,966 A | 9/1997 | Horie | 128/760 |
| 5,676,143 A | 10/1997 | Simonsen | 128/633 |
| 5,678,306 A | 10/1997 | Bozeman | 29/888.025 |
| 5,680,858 A | 10/1997 | Hansen | 128/635 |
| 5,680,872 A | 10/1997 | Sesekura | 128/760 |
| 5,682,233 A | 10/1997 | Brinda | 356/246 |
| 5,682,884 A | 11/1997 | Hill | 128/637 |
| 5,683,562 A | 11/1997 | Schaffar | 204/403 |
| 5,691,898 A | 11/1997 | Rosenberg | 700/85 |
| 5,692,514 A | 12/1997 | Bowman | 600/504 |
| 5,695,947 A | 12/1997 | Guo | 435/11 |
| 5,700,695 A | 12/1997 | Yassinzadeh | 436/180 |
| 5,705,045 A | 1/1998 | Park | 204/403 |
| 5,707,384 A | 1/1998 | Kim | 606/181 |
| 5,708,247 A | 1/1998 | McAleer | 204/403 |
| 5,709,668 A | 1/1998 | Wacks | 604/232 |
| 5,709,699 A | 1/1998 | Warner | 606/181 |
| 5,710,011 A | 1/1998 | Forrow | 435/25 |
| 5,714,123 A | 2/1998 | Sohrab | 422/99 |
| 5,714,390 A | 2/1998 | Hallowitz | 436/526 |
| 5,719,034 A | 2/1998 | Kiser | 435/14 |
| 5,720,862 A | 2/1998 | Hamamoto | 204/403 |
| 5,720,924 A | 2/1998 | Eikmeier | 422/102 |
| D392,391 S | 3/1998 | Douglas | D24/225 |
| D392,740 S | 3/1998 | Yung | D24/169 |
| 5,723,284 A | 3/1998 | Ye | 435/4 |
| 5,727,548 A | 3/1998 | Hill | 128/637 |
| 5,729,905 A | 3/1998 | Mathiasmeier | 33/3 R |
| 5,730,753 A | 3/1998 | Morita | 606/181 |
| 5,733,085 A | 3/1998 | Shida | 411/442 |
| 5,733,300 A | 3/1998 | Pambianchi | 606/181 |
| D393,716 S | 4/1998 | Brenneman | D24/147 |
| D393,717 S | 4/1998 | Brenneman | D24/147 |
| 5,735,868 A | 4/1998 | Lee | 606/189 |
| 5,736,103 A | 4/1998 | Pugh | 422/68.1 |
| 5,738,244 A | 4/1998 | Charlton | 221/26 |
| 5,741,228 A | 4/1998 | Lambrecht | 604/93 |
| 5,741,634 A | 4/1998 | Nozoe | 435/4 |
| RE35,803 E | 5/1998 | Lange | 606/182 |
| 5,746,217 A | 5/1998 | Erickson | 128/760 |
| 5,746,761 A | 5/1998 | Turchin | 606/181 |
| 5,746,898 A | 5/1998 | Preidel | 204/403 |
| 5,753,429 A | 5/1998 | Pugh | 435/4 |
| 5,753,452 A | 5/1998 | Smith | 435/14 |
| 5,755,228 A | 5/1998 | Wilson | 600/459 |
| 5,755,733 A | 5/1998 | Morita | 606/182 |
| 5,758,643 A | 6/1998 | Wong | 600/309 |
| 5,759,364 A | 6/1998 | Charlton | 204/403 |
| 5,762,770 A | 6/1998 | Pritchard | 204/403 |
| 5,770,086 A | 6/1998 | Indriksons | 210/643 |
| 5,770,369 A | 6/1998 | Meade | 435/6 |
| 5,772,586 A | 6/1998 | Heinonen | 600/300 |
| 5,772,677 A | 6/1998 | Mawhirt | 606/181 |
| 5,773,270 A | 6/1998 | D'Orazio | 435/177 |
| 5,776,157 A | 7/1998 | Thorne | 606/182 |
| 5,776,719 A | 7/1998 | Douglas | 435/28 |
| 5,779,365 A | 7/1998 | Takaki | 374/161 |
| 5,780,304 A | 7/1998 | Matzinger | 436/169 |
| 5,782,770 A | 7/1998 | Mooradian | 600/476 |
| 5,782,852 A | 7/1998 | Foggia | 606/182 |
| 5,788,651 A | 8/1998 | Weilandt | 600/567 |
| 5,788,652 A | 8/1998 | Rahn | 600/577 |
| 5,789,255 A | 8/1998 | Yu | 536/95 |
| 5,794,219 A | 8/1998 | Brown | 705/37 |
| 5,795,725 A | 8/1998 | Buechler | 435/7.1 |
| 5,795,774 A | 8/1998 | Matsumoto | 435/287.9 |
| 5,797,940 A | 8/1998 | Mawhirt | 606/167 |
| 5,797,942 A | 8/1998 | Schraga | 606/182 |
| 5,798,030 A | 8/1998 | Raguse | 204/403 |
| 5,798,031 A | 8/1998 | Charlton | 204/403 |
| 5,800,781 A | 9/1998 | Gavin | 422/73 |
| 5,801,057 A | 9/1998 | Smart | 436/68 |
| 5,807,375 A | 9/1998 | Gross | 604/890.1 |
| 5,810,199 A | 9/1998 | Charlton | 221/31 |
| D399,566 S | 10/1998 | Sohrab | D24/169 |
| 5,820,551 A | 10/1998 | Hill | 600/347 |
| 5,822,715 A | 10/1998 | Worthington | 702/19 |
| 5,823,973 A | 10/1998 | Racchini | 600/573 |
| 5,824,491 A | 10/1998 | Priest | 435/28 |
| 5,827,181 A | 10/1998 | Dias | 600/322 |
| 5,828,943 A | 10/1998 | Brown | 434/258 |
| 5,829,589 A | 11/1998 | Nguyen | 206/366 |
| 5,830,219 A | 11/1998 | Bird | 606/130 |
| 5,832,448 A | 11/1998 | Brown | 705/2 |
| 5,840,020 A | 11/1998 | Heinonen | 600/309 |
| 5,840,171 A | 11/1998 | Birch | 205/335 |
| 5,843,691 A | 12/1998 | Douglas | 435/14 |
| 5,843,692 A | 12/1998 | Phillips | 435/14 |
| 5,846,216 A | 12/1998 | Gonzales | 604/2 |
| 5,846,486 A | 12/1998 | Pugh | 422/56 |
| 5,846,490 A | 12/1998 | Yokota | 422/66 |
| 5,849,174 A | 12/1998 | Sanghera | 205/775 |
| 5,853,373 A | 12/1998 | Griffith | 600/554 |
| 5,854,074 A | 12/1998 | Charlton | 436/46 |
| D403,975 S | 1/1999 | Douglas | D10/81 |
| 5,855,377 A | 1/1999 | Murphy | 279/50 |
| 5,855,801 A | 1/1999 | Lin | 216/2 |
| 5,856,174 A | 1/1999 | Lipshutz | 435/286.5 |
| 5,856,195 A | 1/1999 | Charlton | 436/50 |
| 5,857,967 A | 1/1999 | Frid | 600/301 |
| 5,857,983 A | 1/1999 | Douglas | 600/538 |
| 5,858,804 A | 1/1999 | Zanzucchi | 506/9 |
| 5,860,922 A | 1/1999 | Gordon et al. | 600/431 |
| 5,863,800 A | 1/1999 | Eikmeier | 436/48 |
| 5,866,353 A | 2/1999 | Berneth | 435/26 |
| 5,868,135 A | 2/1999 | Kaufman | 128/630 |
| 5,868,772 A | 2/1999 | LeVaughn | 606/181 |
| 5,869,972 A | 2/1999 | Birch | 324/439 |
| 5,871,494 A | 2/1999 | Simons | 606/181 |
| 5,872,713 A | 2/1999 | Douglas | 702/85 |
| 5,873,887 A | 2/1999 | King | 606/182 |
| 5,876,351 A | 3/1999 | Rohde | 600/523 |
| 5,876,957 A | 3/1999 | Douglas | 435/28 |
| 5,879,163 A | 3/1999 | Brown | 434/236 |
| 5,879,310 A | 3/1999 | Sopp | 600/578 |
| 5,879,311 A | 3/1999 | Duchon | 600/583 |
| 5,879,373 A | 3/1999 | Roeper | 606/344 |
| 5,880,829 A | 3/1999 | Kauhaniemi | 356/246 |
| 5,882,494 A | 3/1999 | van Antwerp | 204/403 |
| 5,885,211 A | 3/1999 | Eppstein | 600/309 |
| 5,886,056 A | 3/1999 | Hershkowitz | 518/703 |
| 5,887,133 A | 3/1999 | Brown | 395/200.3 |
| 5,890,128 A | 3/1999 | Diaz | 705/2 |
| RE36,191 E | 4/1999 | Solomon | 395/308 |
| 5,891,053 A | 4/1999 | Sesekura | 600/583 |
| 5,892,569 A | 4/1999 | Van de Velde | 351/221 |
| 5,893,848 A | 4/1999 | Negus | 606/41 |
| 5,893,870 A | 4/1999 | Talen | 606/201 |
| 5,897,493 A | 4/1999 | Brown | 600/300 |
| 5,897,569 A | 4/1999 | Kellogg | 606/169 |
| 5,899,855 A | 5/1999 | Brown | 600/301 |
| 5,899,915 A | 5/1999 | Saadat | 606/170 |
| 5,900,130 A | 5/1999 | Benvegnu | 204/453 |
| 5,902,731 A | 5/1999 | Ouyang | 435/26 |
| 5,906,921 A | 5/1999 | Ikeda | 435/25 |
| D411,619 S | 6/1999 | Duchon | D24/146 |
| 5,908,416 A | 6/1999 | Costello | 606/9 |
| 5,911,937 A | 6/1999 | Hekal | 264/255 |
| 5,912,134 A | 6/1999 | Shartle | 435/7.24 |
| 5,913,310 A | 6/1999 | Brown | 128/897 |
| 5,916,156 A | 6/1999 | Hildenbrand | 600/347 |
| 5,916,229 A | 6/1999 | Evans | 606/171 |
| 5,916,230 A | 6/1999 | Brenneman | 606/172 |
| 5,918,603 A | 7/1999 | Brown | 128/897 |
| 5,919,711 A | 7/1999 | Boyd | 436/178 |
| 5,921,963 A | 7/1999 | Erez | 604/192 |
| 5,922,188 A | 7/1999 | Ikeda | 204/777.5 |
| 5,922,530 A | 7/1999 | Yu | 435/4 |
| 5,922,591 A | 7/1999 | Anderson | 435/287.2 |

| Patent No. | Date | Inventor | Class |
|---|---|---|---|
| RE36,268 E | 8/1999 | Szuminsky | 205/777.5 |
| 5,931,794 A | 8/1999 | Pitesky | 600/556 |
| 5,933,136 A | 8/1999 | Brown | 345/327 |
| 5,935,075 A | 8/1999 | Casscells | 600/474 |
| 5,938,635 A | 8/1999 | Kuhle | 604/506 |
| 5,938,679 A | 8/1999 | Freeman | 606/181 |
| 5,940,153 A | 8/1999 | Castaneda | 349/58 |
| 5,942,102 A | 8/1999 | Hodges | 205/775 |
| 5,942,189 A | 8/1999 | Wolfbeis | 422/82.08 |
| 5,947,957 A | 9/1999 | Morris | 606/13 |
| 5,951,300 A | 9/1999 | Brown | 434/236 |
| 5,951,492 A | 9/1999 | Douglas | 600/583 |
| 5,951,493 A | 9/1999 | Douglas | 600/583 |
| 5,951,582 A | 9/1999 | Thorne | 606/182 |
| 5,951,836 A | 9/1999 | McAleer | 204/403 |
| 5,954,738 A | 9/1999 | LeVaughn | 604/181 |
| 5,956,501 A | 9/1999 | Brown | 395/500.32 |
| 5,957,846 A | 9/1999 | Chiang | 600/447 |
| 5,958,199 A | 9/1999 | Miyamoto | 204/403 |
| 5,959,098 A | 9/1999 | Goldberg | 536/25.3 |
| 5,960,403 A | 9/1999 | Brown | 705/2 |
| 5,961,451 A | 10/1999 | Reber | 600/322 |
| 5,964,718 A | 10/1999 | Duchon | 600/583 |
| 5,965,380 A | 10/1999 | Heller | 435/14 |
| 5,968,063 A | 10/1999 | Chu | 606/185 |
| 5,968,760 A | 10/1999 | Phillips | 435/14 |
| 5,968,836 A | 10/1999 | Matzinger | 436/169 |
| 5,971,941 A | 10/1999 | Simons | 606/573 |
| 5,972,199 A | 10/1999 | Heller | 205/777.5 |
| 5,972,294 A | 10/1999 | Smith | 422/58 |
| 5,972,715 A | 10/1999 | Celentano | 436/164 |
| 5,974,124 A | 10/1999 | Schlueter | 379/106.02 |
| 5,976,085 A | 11/1999 | Kimball | 600/309 |
| 5,983,193 A | 11/1999 | Heinonen | 705/2 |
| 5,985,116 A | 11/1999 | Ikeda | 204/403 |
| 5,985,559 A | 11/1999 | Brown | 435/6 |
| 5,986,754 A | 11/1999 | Harding | 356/246 |
| 5,993,400 A | 11/1999 | Rincoe | 600/595 |
| 5,993,434 A | 11/1999 | Dev | 604/501 |
| D417,504 S | 12/1999 | Love | D24/169 |
| 5,997,476 A | 12/1999 | Brown | 600/300 |
| 5,997,561 A | 12/1999 | Boecker | 606/182 |
| 5,997,817 A | 12/1999 | Crismore | 422/58 |
| 5,997,818 A | 12/1999 | Hacker | 422/681 |
| 6,001,067 A | 12/1999 | Shults | 600/584 |
| 6,007,497 A | 12/1999 | Huitema | 600/567 |
| D418,602 S | 1/2000 | Prokop | D24/169 |
| 6,014,577 A | 1/2000 | Henning | 600/345 |
| 6,015,392 A | 1/2000 | Douglas | 600/583 |
| 6,018,289 A | 1/2000 | Sekura | 340/309.4 |
| 6,020,110 A | 2/2000 | Williams | 430/315 |
| 6,022,324 A | 2/2000 | Skinner | 600/566 |
| 6,022,366 A | 2/2000 | Schraga | 606/181 |
| 6,022,748 A | 2/2000 | Charych | 436/527 |
| 6,023,629 A | 2/2000 | Tamada | 600/347 |
| 6,023,686 A | 2/2000 | Brown | 705/37 |
| 6,027,459 A | 2/2000 | Shain | 600/573 |
| 6,030,399 A | 2/2000 | Ignotz | 606/167 |
| 6,030,827 A | 2/2000 | Davis | 435/287 |
| 6,030,967 A | 2/2000 | Marui | 514/215 |
| 6,032,059 A | 2/2000 | Henning | 600/345 |
| 6,032,119 A | 2/2000 | Brown | 705/2 |
| 6,033,421 A | 3/2000 | Theiss | 606/186 |
| 6,033,866 A | 3/2000 | Guo | 435/14 |
| 6,036,924 A | 3/2000 | Simons | 422/100 |
| 6,037,178 A | 3/2000 | Leiner | 436/50 |
| 6,041,253 A | 3/2000 | Kost | 604/20 |
| 6,045,567 A | 4/2000 | Taylor | 606/181 |
| 6,046,055 A | 4/2000 | Wolfbeis | 436/172 |
| 6,048,352 A | 4/2000 | Douglas | 606/181 |
| D424,696 S | 5/2000 | Ray | D24/169 |
| 6,056,701 A | 5/2000 | Duchon | 600/583 |
| 6,059,815 A | 5/2000 | Lee | 606/209 |
| 6,060,327 A | 5/2000 | Keen | 436/518 |
| 6,061,128 A | 5/2000 | Zweig | 356/243.4 |
| 6,063,039 A | 5/2000 | Cunningham | 600/573 |
| 6,066,103 A | 5/2000 | Duchon | 600/583 |
| 6,066,243 A | 5/2000 | Anderson | 422/82.01 |
| 6,066,296 A | 5/2000 | Brady | 422/63 |
| 6,067,463 A | 5/2000 | Jeng | 600/336 |
| 6,068,615 A | 5/2000 | Brown | 604/207 |
| D426,638 S | 6/2000 | Ray | D24/169 |
| 6,070,761 A | 6/2000 | Bloom | 222/81 |
| 6,071,249 A | 6/2000 | Cunningham | 600/578 |
| 6,071,250 A | 6/2000 | Douglas et al. | 600/583 |
| 6,071,251 A | 6/2000 | Cunningham | 600/584 |
| 6,071,294 A | 6/2000 | Simons | 606/181 |
| 6,071,391 A | 6/2000 | Gotoh | 204/403 |
| 6,074,360 A | 6/2000 | Haar | 604/57 |
| 6,077,408 A | 6/2000 | Miyamoto | 204/403 |
| 6,080,106 A | 6/2000 | Lloyd | 600/300 |
| 6,080,172 A | 6/2000 | Fujiwara | 606/166 |
| D428,150 S | 7/2000 | Ruf | D24/146 |
| 6,083,196 A | 7/2000 | Trautman | 604/46 |
| 6,083,710 A | 7/2000 | Heller | 435/14 |
| 6,084,660 A | 7/2000 | Shartle | 356/39 |
| 6,085,576 A | 7/2000 | Sunshine | 73/29.01 |
| 6,086,544 A | 7/2000 | Hibner | 600/568 |
| 6,086,545 A | 7/2000 | Roe | 600/570 |
| 6,086,562 A | 7/2000 | Jacobsen | 604/156 |
| 6,090,078 A | 7/2000 | Erskine | 604/198 |
| 6,091,975 A | 7/2000 | Daddona | 600/345 |
| 6,093,146 A | 7/2000 | Filangeri | 600/300 |
| 6,093,156 A | 7/2000 | Cunningham | 600/573 |
| D428,993 S | 8/2000 | Lubs | D24/165 |
| 6,099,484 A | 8/2000 | Douglas | 600/583 |
| 6,099,802 A | 8/2000 | Pugh | 422/58 |
| 6,100,107 A | 8/2000 | Lei | 438/50 |
| 6,101,478 A | 8/2000 | Brown | 705/2 |
| 6,102,933 A | 8/2000 | Lee | 606/209 |
| 6,103,033 A | 8/2000 | Say | 156/73.1 |
| 6,103,509 A | 8/2000 | Sode | 435/190 |
| 6,104,940 A | 8/2000 | Watanabe | 600/345 |
| 6,106,751 A | 8/2000 | Talbot | 264/81 |
| 6,107,083 A | 8/2000 | Collins | 435/288 |
| 6,113,578 A | 9/2000 | Brown | 604/207 |
| 6,117,155 A | 9/2000 | Lee | 606/189 |
| 6,117,630 A | 9/2000 | Reber | 435/4 |
| 6,118,126 A | 9/2000 | Zanzucchi | 250/458.1 |
| 6,119,033 A | 9/2000 | Spigelman | 600/426 |
| 6,120,462 A | 9/2000 | Hibner | 600/566 |
| 6,120,676 A | 9/2000 | Heller | 205/777.5 |
| 6,121,009 A | 9/2000 | Heller | 435/14 |
| 6,122,536 A | 9/2000 | Sun | 600/341 |
| 6,126,804 A | 10/2000 | Andresen | 204/601 |
| 6,126,899 A | 10/2000 | Woudenberg | 422/50 |
| 6,129,823 A | 10/2000 | Hughes | 204/403.01 |
| 6,132,449 A | 10/2000 | Lum | 606/181 |
| 6,133,837 A | 10/2000 | Riley | 340/573.1 |
| 6,134,461 A | 10/2000 | Say | 600/345 |
| 6,136,013 A | 10/2000 | Marshall | 606/167 |
| 6,139,562 A | 10/2000 | Mauze | 606/171 |
| 6,143,164 A | 11/2000 | Heller | 600/583 |
| 6,144,837 A | 11/2000 | Quy | 434/307 R |
| 6,144,976 A | 11/2000 | Silva et al. | 708/100 |
| 6,149,203 A | 11/2000 | Hanlon | 283/72 |
| 6,151,586 A | 11/2000 | Brown | 705/14 |
| 6,152,875 A | 11/2000 | Hakamata | 600/319 |
| 6,152,942 A | 11/2000 | Brenneman | 606/181 |
| 6,153,069 A | 11/2000 | Pottgen | 204/403 |
| RE36,991 E | 12/2000 | Yamamoto | 204/403 |
| 6,155,267 A | 12/2000 | Nelson | 128/899 |
| 6,155,992 A | 12/2000 | Henning et al. | 600/583 |
| 6,156,051 A | 12/2000 | Schraga | 606/181 |
| 6,157,442 A | 12/2000 | Raskas | 356/39 |
| 6,159,147 A | 12/2000 | Lichter | 600/300 |
| 6,159,424 A | 12/2000 | Kauhaniemi | 422/63 |
| 6,161,095 A | 12/2000 | Brown | 705/2 |
| 6,162,397 A | 12/2000 | Jurik | 422/56 |
| 6,162,611 A | 12/2000 | Heller | 435/14 |
| 6,167,362 A | 12/2000 | Brown | 703/11 |
| 6,167,386 A | 12/2000 | Brown | 705/37 |
| 6,168,563 B1 | 1/2001 | Brown | 600/301 |
| 6,168,957 B1 | 1/2001 | Matzinger | 436/518 |
| 6,171,325 B1 | 1/2001 | Mauze | 606/171 |
| 6,172,743 B1 | 1/2001 | Kley et al. | 356/39 |
| 6,175,752 B1 | 1/2001 | Say | 600/345 |
| 6,176,847 B1 | 1/2001 | Humphreys | 604/246 |

| Patent | Kind | Date | Name | Class |
|---|---|---|---|---|
| 6,176,865 | B1 | 1/2001 | Mauze | 606/171 |
| 6,177,000 | B1 | 1/2001 | Peterson | 205/777.5 |
| 6,177,931 | B1 | 1/2001 | Alexander | 725/52 |
| 6,183,489 | B1 | 2/2001 | Douglas | 606/181 |
| 6,186,145 | B1 | 2/2001 | Brown | 128/897 |
| 6,190,612 | B1 | 2/2001 | Berger | 422/82.07 |
| 6,191,852 | B1 | 2/2001 | Paffhausen | 356/244 |
| 6,192,891 | B1 | 2/2001 | Gravel | 128/920 |
| 6,193,673 | B1 | 2/2001 | Viola | 600/568 |
| 6,193,873 | B1 | 2/2001 | Ohara | 205/792 |
| 6,194,900 | B1 | 2/2001 | Freeman | 324/321 |
| 6,197,040 | B1 | 3/2001 | LeVaughn | 606/182 |
| 6,197,257 | B1 | 3/2001 | Raskas | 422/82.05 |
| 6,200,773 | B1 | 3/2001 | Ouyang | 435/26 |
| 6,203,504 | B1 | 3/2001 | Latterell | 600/576 |
| 6,206,841 | B1 | 3/2001 | Cunningham et al. | 600/584 |
| 6,210,133 | B1 | 4/2001 | Aboul-Hosn | 417/423.1 |
| 6,210,272 | B1 | 4/2001 | Brown | 463/1 |
| 6,210,369 | B1 | 4/2001 | Wilmot | 604/157 |
| 6,210,420 | B1 | 4/2001 | Mauze | 606/182 |
| 6,210,421 | B1 | 4/2001 | Bocker | 606/182 |
| 6,212,417 | B1 | 4/2001 | Ikeda | 204/403.14 |
| 6,214,626 | B1 | 4/2001 | Meller | 436/165 |
| 6,214,804 | B1 | 4/2001 | Felgner | 514/44 |
| 6,218,571 | B1 | 4/2001 | Zheng | 562/61 |
| 6,219,574 | B1 | 4/2001 | Cormier | 604/20 |
| 6,221,023 | B1 | 4/2001 | Matsuba | 600/486 |
| 6,221,238 | B1 | 4/2001 | Grundig | 205/777.5 |
| 6,224,617 | B1 | 5/2001 | Saadat et al. | 606/170 |
| 6,225,078 | B1 | 5/2001 | Ikeda | 435/25 |
| 6,228,100 | B1 | 5/2001 | Schraga | 606/183 |
| 6,230,051 | B1 | 5/2001 | Cormier | 604/20 |
| 6,230,501 | B1 | 5/2001 | Bailey | 62/51.1 |
| 6,231,531 | B1 | 5/2001 | Lum | 601/46 |
| 6,233,471 | B1 | 5/2001 | Berner | 600/345 |
| 6,233,539 | B1 | 5/2001 | Brown | 703/11 |
| 6,234,772 | B1 | 5/2001 | Wampler | 417/423.12 |
| 6,240,393 | B1 | 5/2001 | Brown | 705/1 |
| D444,235 | S | 6/2001 | Roberts | D24/169 |
| 6,241,862 | B1 | 6/2001 | McAleer | 204/403 |
| 6,242,207 | B1 | 6/2001 | Douglas | 435/25 |
| 6,245,060 | B1 | 6/2001 | Loomis | 606/9 |
| 6,245,215 | B1 | 6/2001 | Douglas | 205/775 |
| 6,246,992 | B1 | 6/2001 | Brown | 705/2 |
| 6,248,065 | B1 | 6/2001 | Brown | 600/300 |
| 6,251,083 | B1 | 6/2001 | Yum | 600/584 |
| 6,251,121 | B1 | 6/2001 | Saadat | 606/180 |
| 6,251,260 | B1 | 6/2001 | Heller | 205/777.5 |
| 6,251,344 | B1 | 6/2001 | Goldstein | 422/123 |
| D444,557 | S | 7/2001 | Levaughn | D24/146 |
| 6,254,831 | B1 | 7/2001 | Barnard | 422/82.08 |
| 6,256,533 | B1 | 7/2001 | Yuzhakov | 604/21 |
| 6,258,111 | B1 | 7/2001 | Ross | 606/181 |
| 6,258,229 | B1 | 7/2001 | Winarta | 204/403 |
| 6,258,254 | B1 | 7/2001 | Miyamoto | 205/777.5 |
| 6,261,241 | B1 | 7/2001 | Burbank | 600/564 |
| 6,261,245 | B1 | 7/2001 | Kawai | 600/576 |
| 6,261,519 | B1 | 7/2001 | Harding | 422/58 |
| 6,264,635 | B1 | 7/2001 | Wampler | 604/151 |
| 6,268,161 | B1 | 7/2001 | Han | 435/14 |
| 6,268,162 | B1 | 7/2001 | Phillips | 435/14 |
| 6,269,314 | B1 | 7/2001 | Iitawaki | 702/23 |
| 6,270,455 | B1 | 8/2001 | Brown | 600/300 |
| 6,270,637 | B1 | 8/2001 | Crismore | 204/403 |
| 6,272,359 | B1 | 8/2001 | Kivela | 455/567 |
| 6,272,364 | B1 | 8/2001 | Kurnik | 600/345 |
| 6,275,717 | B1 | 8/2001 | Gross | 600/345 |
| 6,280,254 | B1 | 8/2001 | Wu | 439/630 |
| 6,281,006 | B1 | 8/2001 | Heller | 435/287.9 |
| 6,283,926 | B1 | 9/2001 | Cunningham | 600/573 |
| 6,283,982 | B1 | 9/2001 | Levaughn | 606/172 |
| 6,284,478 | B1 | 9/2001 | Heller | 435/14 |
| 6,285,448 | B1 | 9/2001 | Kuenstner | 356/39 |
| 6,285,454 | B1 | 9/2001 | Douglas | 356/446 |
| 6,289,254 | B1 | 9/2001 | Shimizu | 700/96 |
| 6,290,683 | B1 | 9/2001 | Erez | 604/273 |
| 6,294,897 | B1 | 9/2001 | Champlin | 320/153 |
| 6,295,506 | B1 | 9/2001 | Heinonen | 702/104 |
| 6,299,578 | B1 | 10/2001 | Kurnik | 600/309 |
| 6,299,596 | B1 | 10/2001 | Ding | 604/96.01 |
| 6,299,757 | B1 | 10/2001 | Feldman | 205/775 |
| 6,302,844 | B1 | 10/2001 | Walker | 600/300 |
| 6,302,855 | B1 | 10/2001 | Lav | 600/584 |
| 6,305,804 | B1 | 10/2001 | Rice | 351/221 |
| 6,306,104 | B1 | 10/2001 | Cunningham | 600/573 |
| 6,306,152 | B1 | 10/2001 | Verdonk | 606/182 |
| 6,306,347 | B1 | 10/2001 | Mason | 422/58 |
| 6,309,351 | B1 | 10/2001 | Kurnik | 600/309 |
| 6,309,535 | B1 | 10/2001 | Williams | 205/777.5 |
| 6,312,612 | B1 | 11/2001 | Sherman | 216/2 |
| 6,315,738 | B1 | 11/2001 | Nishikawa | 600/583 |
| 6,318,970 | B1 | 11/2001 | Backhouse | 417/92 |
| 6,319,210 | B1 | 11/2001 | Douglas | 600/583 |
| 6,322,574 | B1 | 11/2001 | Lloyd | 606/181 |
| 6,322,808 | B1 | 11/2001 | Trautman | 424/448 |
| 6,322,963 | B1 | 11/2001 | Bauer | 435/4 |
| 6,329,161 | B1 | 12/2001 | Heller | 435/14 |
| 6,330,426 | B2 | 12/2001 | Brown | 434/307 R |
| 6,331,163 | B1 | 12/2001 | Kaplan | 600/486 |
| 6,332,871 | B1 | 12/2001 | Douglas | 600/583 |
| 6,334,363 | B1 | 1/2002 | Testud | 73/862 |
| 6,334,778 | B1 | 1/2002 | Brown | 434/258 |
| 6,334,856 | B1 | 1/2002 | Allen | 604/191 |
| 6,335,203 | B1 | 1/2002 | Patel | 436/169 |
| 6,335,856 | B1 | 1/2002 | Boisrayon | 604/191 |
| 6,336,900 | B1 | 1/2002 | Alleckson | 600/485 |
| 6,338,790 | B1 | 1/2002 | Feldman | 205/777.5 |
| 6,346,120 | B1 | 2/2002 | Yamazaki | 623/3.13 |
| 6,349,229 | B1 | 2/2002 | Watanabe | 600/345 |
| 6,350,273 | B1 | 2/2002 | Minagawa | 606/186 |
| 6,350,451 | B1 | 2/2002 | Horn | 424/184.1 |
| 6,352,514 | B1 | 3/2002 | Douglas | 600/583 |
| 6,352,523 | B1 | 3/2002 | Brown | 604/207 |
| 6,353,753 | B1 | 3/2002 | Flock | 600/473 |
| 6,364,889 | B1 | 4/2002 | Kheiri | 606/181 |
| 6,364,890 | B1 | 4/2002 | Lum | 606/181 |
| 6,368,273 | B1 | 4/2002 | Brown | 600/300 |
| 6,375,469 | B1 | 4/2002 | Brown | 434/236 |
| 6,375,627 | B1 | 4/2002 | Mauze | 600/584 |
| 6,379,301 | B1 | 4/2002 | Worthington | 600/309 |
| 6,379,317 | B1 | 4/2002 | Kintzig | 600/573 |
| 6,379,324 | B1 | 4/2002 | Gartstein | 604/22 |
| 6,379,969 | B1 | 4/2002 | Mauze | 436/68 |
| 6,381,577 | B1 | 4/2002 | Brown | 705/2 |
| D456,910 | S | 5/2002 | Clark | D24/225 |
| 6,387,709 | B1 | 5/2002 | Mason | 436/164 |
| 6,391,005 | B1 | 5/2002 | Lum | 604/117 |
| 6,395,227 | B1 | 5/2002 | Kiser | 422/56 |
| 6,398,522 | B2 | 6/2002 | Skill | 417/410.3 |
| 6,398,562 | B1 | 6/2002 | Butler | 439/91 |
| 6,399,394 | B1 | 6/2002 | Dahm | 436/180 |
| 6,402,701 | B1 | 6/2002 | Kaplan | 600/567 |
| 6,402,704 | B1 | 6/2002 | Mcmorrow | 600/576 |
| 6,409,740 | B1 | 6/2002 | Kuhr | 606/182 |
| 6,413,410 | B1 | 7/2002 | Hodges | 205/775 |
| 6,413,411 | B1 | 7/2002 | Pottgen | 205/777.5 |
| 6,415,821 | B2 | 7/2002 | Kamholz | 137/827 |
| 6,420,128 | B1 | 7/2002 | Ouyang | 435/14 |
| 6,421,633 | B1 | 7/2002 | Heinonen | 703/11 |
| 6,423,014 | B1 | 7/2002 | Churchill | 600/587 |
| 6,428,664 | B1 | 8/2002 | Bhullar | 204/403.03 |
| 6,436,055 | B1 | 8/2002 | Roe | 600/584 |
| 6,436,256 | B1 | 8/2002 | Williams | 204/403.06 |
| 6,436,721 | B1 | 8/2002 | Kuo | 436/514 |
| 6,440,645 | B1 | 8/2002 | Yon-Hin | 430/322 |
| 6,444,115 | B1 | 9/2002 | Hodges | 205/792 |
| 6,447,119 | B1 | 9/2002 | Stewart et al. | 351/212 |
| 6,447,265 | B1 | 9/2002 | Antaki | 417/354 |
| 6,451,040 | B1 | 9/2002 | Purcell | 606/181 |
| 6,453,810 | B1 | 9/2002 | Rossmeisl | 101/123 |
| 6,458,258 | B2 | 10/2002 | Taniike | 204/403 |
| 6,461,496 | B1 | 10/2002 | Feldman | 205/777.5 |
| 6,462,162 | B2 | 10/2002 | van Antwerp | 528/77 |
| 6,464,649 | B1 | 10/2002 | Duchon | 600/583 |
| 6,471,903 | B2 | 10/2002 | Sherman | 264/328.1 |
| 6,472,220 | B1 | 10/2002 | Simons | 436/63 |
| 6,475,360 | B1 | 11/2002 | Hodges | 204/403.14 |
| 6,475,372 | B1 | 11/2002 | Ohara | 205/777.5 |

| Patent No. | Date | Name | Class |
|---|---|---|---|
| 6,475,436 B1 | 11/2002 | Schabbach | 422/64 |
| 6,475,750 B1 | 11/2002 | Han | 435/14 |
| 6,477,394 B2 | 11/2002 | Rice | 600/318 |
| 6,477,424 B1 | 11/2002 | Thompson | 607/60 |
| 6,484,046 B1 | 11/2002 | Say | 600/345 |
| 6,485,439 B1 | 11/2002 | Roe | 600/578 |
| 6,485,461 B1 | 11/2002 | Mason | 604/132 |
| 6,485,923 B1 | 11/2002 | Yani | 435/14 |
| 6,488,827 B1 | 12/2002 | Shartle | 204/403 |
| 6,488,891 B2 | 12/2002 | Mason | 422/58 |
| 6,489,133 B2 | 12/2002 | Phillips | 435/14 |
| 6,491,709 B2 | 12/2002 | Sharma | 606/181 |
| 6,491,870 B2 | 12/2002 | Patel | 422/58 |
| 6,494,830 B1 | 12/2002 | Wessel | 600/300 |
| 6,497,845 B1 | 12/2002 | Sacherer | 422/104 |
| 6,501,404 B2 | 12/2002 | Walker | 341/143 |
| 6,501,976 B1 | 12/2002 | Sohrab | 600/347 |
| 6,503,210 B1 | 1/2003 | Hirao | 600/576 |
| 6,503,231 B1 | 1/2003 | Prausnitz | 604/272 |
| 6,503,290 B1 | 1/2003 | Jarosinski | 75/252 |
| 6,503,381 B1 | 1/2003 | Gotoh | 204/403.14 |
| 6,506,165 B1 | 1/2003 | Sweeney | 600/562 |
| 6,506,168 B1 | 1/2003 | Fathallah | 600/578 |
| 6,506,575 B1 | 1/2003 | Knappe | 435/25 |
| 6,508,785 B1 | 1/2003 | Eppstein | 604/113 |
| 6,512,986 B1 | 1/2003 | Harmon | 702/84 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,521,110 B1 | 2/2003 | Hodges | 204/403.14 |
| 6,521,182 B1 | 2/2003 | Shartle | 422/58 |
| 6,527,521 B2 | 3/2003 | Noda | 417/355 |
| 6,527,716 B1 | 3/2003 | Epstein | 600/309 |
| 6,527,778 B2 | 3/2003 | Athanasiou | 606/80 |
| 6,529,377 B1 | 3/2003 | Somadder | 361/699 |
| 6,530,892 B1 | 3/2003 | Kelly | 600/583 |
| 6,530,937 B1 | 3/2003 | Schraga | 606/182 |
| 6,531,322 B1 | 3/2003 | Jurik | 436/95 |
| 6,533,949 B1 | 3/2003 | Yeshurun | 216/11 |
| 6,537,207 B1 | 3/2003 | Rice | 600/121 |
| 6,537,242 B1 | 3/2003 | Palmer | 604/22 |
| 6,537,264 B1 | 3/2003 | Cormier et al. | 604/506 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,541,266 B2 | 4/2003 | Modzelewski | 436/95 |
| 6,547,954 B2 | 4/2003 | Ikeda | 205/777.5 |
| 6,549,796 B2 | 4/2003 | Sohrab | 600/345 |
| 6,551,494 B1 | 4/2003 | Feldman | 205/777.5 |
| 6,553,244 B2 | 4/2003 | Lesho | 600/309 |
| 6,554,381 B2 | 4/2003 | Locher | 347/7 |
| 6,555,061 B1 | 4/2003 | Leong | 422/58 |
| D475,136 S | 5/2003 | Taniguchi | D24/165 |
| 6,558,320 B1 | 5/2003 | Causey | 600/300 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,560,471 B1 | 5/2003 | Heller | 600/347 |
| 6,561,978 B1 | 5/2003 | Conn | 600/309 |
| 6,561,989 B2 | 5/2003 | Whitson | 600/573 |
| 6,562,210 B1 | 5/2003 | Bhullar | 204/403.3 |
| 6,565,509 B1 | 5/2003 | Plante | 600/365 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,572,822 B2 | 6/2003 | Jurik | 422/56 |
| 6,574,490 B2 | 6/2003 | Abbink | 600/316 |
| 6,575,905 B2 | 6/2003 | Knobbe | 600/365 |
| 6,576,101 B1 | 6/2003 | Heller | 204/403.14 |
| 6,576,117 B1 | 6/2003 | Iketaki | 205/777.5 |
| 6,576,416 B2 | 6/2003 | Haviland | 435/4 |
| 6,579,690 B1 | 6/2003 | Bonnecaze | 435/14 |
| 6,582,573 B2 | 6/2003 | Douglas | 204/403.1 |
| 6,584,338 B1 | 6/2003 | Van Muiswinkel | 600/419 |
| D477,670 S | 7/2003 | Jurik | D24/225 |
| 6,586,199 B2 | 7/2003 | Ouyang | 435/26 |
| 6,587,705 B1 | 7/2003 | Berner et al. | 600/347 |
| 6,589,260 B1 | 7/2003 | Schmelzeisen-Redeker | 606/181 |
| 6,589,261 B1 | 7/2003 | Abulhaj | 606/181 |
| 6,591,124 B2 | 7/2003 | Sherman | 600/345 |
| 6,591,125 B1 | 7/2003 | Buse | 600/347 |
| 6,592,744 B1 | 7/2003 | Hodges | 205/775 |
| 6,592,745 B1 | 7/2003 | Feldman | 205/777.5 |
| 6,595,919 B2 | 7/2003 | Berner | 600/365 |
| 6,599,407 B2 | 7/2003 | Taniike | 204/403.1 |
| 6,599,693 B1 | 7/2003 | Webb | 435/4 |
| 6,599,769 B2 | 7/2003 | Kondo | 438/28 |
| 6,601,534 B2 | 8/2003 | Hebrank | 119/6.8 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,604,050 B2 | 8/2003 | Trippel | 702/19 |
| 6,607,362 B2 | 8/2003 | Lum | 417/53 |
| 6,607,494 B1 | 8/2003 | Fowler | 600/570 |
| 6,607,658 B1 | 8/2003 | Heller | 205/777.5 |
| 6,612,111 B1 | 9/2003 | Hodges | 60/593 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,620,310 B1 | 9/2003 | Ohara | 205/792 |
| 6,623,501 B2 | 9/2003 | Heller | 606/181 |
| 6,626,851 B2 | 9/2003 | Hirao | 600/576 |
| 6,632,349 B1 | 10/2003 | Hodges | 205/792 |
| 6,635,222 B2 | 10/2003 | Kent | 422/22 |
| 6,638,415 B1 | 10/2003 | Hodges | 205/775 |
| 6,638,772 B1 | 10/2003 | Douglas | 436/518 |
| 6,641,533 B2 | 11/2003 | Causey | 600/300 |
| 6,645,142 B2 | 11/2003 | Braig | 600/300 |
| 6,645,219 B2 | 11/2003 | Roe | 606/182 |
| 6,645,368 B1 | 11/2003 | Beaty | 205/792 |
| 6,649,416 B1 | 11/2003 | Kauer | 436/164 |
| 6,650,915 B2 | 11/2003 | Routt | 600/319 |
| 6,652,720 B1 | 11/2003 | Mansouri | 204/403.11 |
| 6,652,734 B1 | 11/2003 | Hodges | 205/777.5 |
| 6,652,814 B1 | 11/2003 | House | 422/104 |
| D484,600 S | 12/2003 | Kaar | D24/169 |
| 6,656,428 B1 | 12/2003 | Clark et al. | 422/404 |
| 6,656,697 B1 | 12/2003 | Ouyang | 435/7.9 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,662,439 B1 | 12/2003 | Bhullar | 29/825 |
| 6,669,669 B2 | 12/2003 | Flaherty | 604/132 |
| 6,671,527 B2 | 12/2003 | Petersson | 600/316 |
| D484,980 S | 1/2004 | Hartwein | D24/165 |
| 6,673,617 B2 | 1/2004 | Patel | 436/8 |
| 6,676,995 B1 | 1/2004 | Dick | 427/286 |
| 6,679,841 B2 | 1/2004 | Bojan | 600/309 |
| 6,679,852 B1 | 1/2004 | Forster | 600/583 |
| 6,682,933 B2 | 1/2004 | Patel | 436/8 |
| 6,689,411 B2 | 2/2004 | Dick | 427/2.13 |
| 6,706,000 B2 | 3/2004 | Perez | 600/583 |
| 6,706,049 B2 | 3/2004 | Moerman | 606/181 |
| 6,706,159 B2 | 3/2004 | Moerman | 204/403.03 |
| 6,706,232 B2 | 3/2004 | Hasegawa | 264/403.09 |
| 6,709,692 B2 | 3/2004 | Sudor | 427/2.1 |
| 6,713,660 B1 | 3/2004 | Roe | 604/361 |
| 6,716,577 B1 | 4/2004 | Yu | 435/6 |
| 6,719,887 B2 | 4/2004 | Hasegawa | 204/403.09 |
| 6,719,923 B2 | 4/2004 | Stiene | 252/511 |
| 6,721,586 B2 | 4/2004 | Kiser | 600/345 |
| 6,723,046 B2 | 4/2004 | Lichtenstein | 600/300 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,729,546 B2 | 5/2004 | Roustaei | 235/462.45 |
| 6,730,494 B1 | 5/2004 | Toranto | 435/28 |
| 6,731,966 B1 | 5/2004 | Spigelman | 600/407 |
| 6,733,493 B2 | 5/2004 | Gruzdev | 606/9 |
| 6,736,777 B2 | 5/2004 | Kim | 600/365 |
| 6,738,654 B2 | 5/2004 | Sohrab | 600/345 |
| 6,740,215 B1 | 5/2004 | Nakaminami | 204/403.14 |

| | | | | | | | |
|---|---|---|---|---|---|---|---|
| 6,743,211 B1 | 6/2004 | Prausnitz | 604/239 | 6,849,168 B2 | 2/2005 | Madou | 204/416 |
| 6,743,597 B1 | 6/2004 | Guo | 435/14 | 6,849,216 B2 | 2/2005 | Rappin | 264/134 |
| 6,743,635 B2 | 6/2004 | Neel | 436/95 | 6,849,456 B2 | 2/2005 | Patel | 436/8 |
| 6,746,872 B2 | 6/2004 | Zheng | 436/16 | 6,850,790 B2 | 2/2005 | Berner | 600/347 |
| 6,749,618 B2 | 6/2004 | Levaughn | 606/182 | 6,852,119 B1 | 2/2005 | Abulhaj | 606/182 |
| 6,749,740 B2 | 6/2004 | Funderburk | 205/792 | 6,852,212 B2 | 2/2005 | Maxwell | 205/775 |
| 6,749,792 B2 | 6/2004 | Olsen | 264/328.1 | 6,852,500 B1 | 2/2005 | Hoss | 435/14 |
| 6,749,887 B1 | 6/2004 | Dick | 427/2.13 | 6,853,854 B1 | 2/2005 | Proniewicz | 600/319 |
| 6,751,491 B2 | 6/2004 | Lew | 600/345 | 6,855,243 B2 | 2/2005 | Khan | 205/777.5 |
| 6,752,817 B2 | 6/2004 | Flora | 606/181 | 6,856,125 B2 | 2/2005 | Kermani | 324/71.1 |
| 6,753,187 B2 | 6/2004 | Cizdziel | 436/169 | 6,856,928 B2 | 2/2005 | Harmon | 702/84 |
| 6,759,190 B2 | 7/2004 | Lin | 435/4 | 6,858,015 B2 | 2/2005 | List | 600/583 |
| 6,764,496 B2 | 7/2004 | Schraga | 606/182 | 6,858,401 B2 | 2/2005 | Phillips | 435/14 |
| 6,764,581 B1 | 7/2004 | Forrow | 204/403 | 6,859,738 B2 | 2/2005 | Bush | 702/25 |
| 6,767,441 B1 | 7/2004 | Cai | 204/403.03 | 6,862,466 B2 | 3/2005 | Ackerman | 600/347 |
| 6,773,671 B1 | 8/2004 | Lewis | 422/61 | 6,862,534 B2 | 3/2005 | Sterling | 702/23 |
| 6,776,888 B2 | 8/2004 | Yamamoto | 204/403.06 | 6,863,800 B2 | 3/2005 | Karinka | 205/777.5 |
| 6,780,645 B2 | 8/2004 | Hayter | 436/8 | 6,863,801 B2 | 3/2005 | Hodges | 205/792 |
| 6,780,647 B2 | 8/2004 | Fujiwara | 436/169 | 6,865,408 B1 | 3/2005 | Abbink | 600/310 |
| 6,783,502 B2 | 8/2004 | Orloff | 600/583 | 6,866,641 B2 | 3/2005 | Marshall | 600/583 |
| 6,783,537 B1 | 8/2004 | Kuhr | 606/182 | 6,866,675 B2 | 3/2005 | Perez | 606/181 |
| 6,784,274 B2 | 8/2004 | van Antwerp | 528/77 | 6,866,758 B2 | 3/2005 | Bhullar | 204/403.2 |
| 6,786,874 B2 | 9/2004 | Grace | 600/573 | 6,866,822 B1 | 3/2005 | House | 422/82.05 |
| 6,787,013 B2 | 9/2004 | Chang | 204/412 | 6,869,418 B2 | 3/2005 | Marano-Ford | 604/192 |
| 6,787,109 B2 | 9/2004 | Haar | 422/82.05 | 6,872,200 B2 | 3/2005 | Mann | 604/890.1 |
| 6,790,327 B2 | 9/2004 | Nankai | 204/403.1 | 6,872,297 B2 | 3/2005 | Mansouri | 205/775 |
| 6,790,599 B1 | 9/2004 | Madou | 430/320 | 6,872,298 B2 | 3/2005 | Kermani | 205/777.5 |
| 6,792,791 B2 | 9/2004 | Sato | 73/1.02 | 6,872,299 B2 | 3/2005 | Kermani | 205/777.5 |
| 6,793,632 B2 | 9/2004 | Sohrab | 600/573 | 6,872,358 B2 | 3/2005 | Hagen | 422/61 |
| 6,793,633 B2 | 9/2004 | Douglas | 600/583 | 6,875,208 B2 | 4/2005 | Santini | 604/890.1 |
| 6,793,802 B2 | 9/2004 | Lee | 205/777.5 | 6,875,223 B2 | 4/2005 | Argauer | 606/181 |
| 6,797,150 B2 | 9/2004 | Kermani | 205/777.5 | 6,875,327 B1 | 4/2005 | Miyazaki | 204/403.14 |
| 6,800,488 B2 | 10/2004 | Khan | 436/166 | 6,875,613 B2 | 4/2005 | Shartle | 436/63 |
| 6,801,041 B2 | 10/2004 | Karinka | 324/444 | 6,878,120 B2 | 4/2005 | Roe | 600/583 |
| 6,801,804 B2 | 10/2004 | Miller | 604/20 | 6,878,251 B2 | 4/2005 | Hodges | 204/403.14 |
| 6,802,199 B2 | 10/2004 | Hilgers | 72/370.1 | 6,878,255 B1 | 4/2005 | Wang | 204/452 |
| 6,802,811 B1 | 10/2004 | Slepian | 600/309 | 6,878,262 B2 | 4/2005 | Taniike | 205/777.5 |
| 6,802,957 B2 | 10/2004 | Jung | 205/777.5 | 6,880,968 B1 | 4/2005 | Haar | 374/131 |
| 6,805,780 B1 | 10/2004 | Ryu | 204/403.01 | 6,881,203 B2 | 4/2005 | Delmore | 604/272 |
| 6,808,499 B1 | 10/2004 | Churchill | 600/587 | 6,881,322 B2 | 4/2005 | Tokunaga | 205/775 |
| 6,808,908 B2 | 10/2004 | Yao | 435/181 | 6,881,378 B1 | 4/2005 | Zimmer | 422/58 |
| 6,808,937 B2 | 10/2004 | Ligler | 436/518 | 6,881,541 B2 | 4/2005 | Petersen | 435/6 |
| 6,809,807 B1 | 10/2004 | Erickson | 356/213 | 6,881,550 B2 | 4/2005 | Phillips | 435/14 |
| 6,811,406 B2 | 11/2004 | Grube | 439/66 | 6,881,551 B2 | 4/2005 | Heller | 435/14 |
| 6,811,557 B2 | 11/2004 | Schraga | 606/182 | 6,881,578 B2 | 4/2005 | Otake | 436/44 |
| 6,811,659 B2 | 11/2004 | Vachon | 204/224 | 6,882,940 B2 | 4/2005 | Potts | 702/23 |
| 6,811,753 B2 | 11/2004 | Hirao | 422/101 | 6,884,592 B2 | 4/2005 | Matzinger | 435/7.1 |
| 6,811,792 B2 | 11/2004 | Roser | 424/423 | 6,885,196 B2 | 4/2005 | Taniike | 324/444 |
| 6,812,031 B1 | 11/2004 | Carlsson | 436/52 | 6,885,883 B2 | 4/2005 | Parris | 600/347 |
| 6,814,843 B1 | 11/2004 | Bhullar | 204/403.01 | 6,887,202 B2 | 5/2005 | Currie | 600/309 |
| 6,814,844 B2 | 11/2004 | Bhullar | 204/403.1 | 6,887,239 B2 | 5/2005 | Elstrom | 606/41 |
| 6,814,845 B2 | 11/2004 | Wilson | 204/486 | 6,887,253 B2 | 5/2005 | Schraga | 606/181 |
| 6,815,186 B2 | 11/2004 | Clark | 435/183 | 6,887,254 B1 | 5/2005 | Curie | 606/181 |
| 6,816,742 B2 | 11/2004 | Kim | 600/345 | 6,887,426 B2 | 5/2005 | Phillips | 422/56 |
| 6,818,180 B2 | 11/2004 | Douglas | 422/58 | 6,887,709 B2 | 5/2005 | Leong | 436/8 |
| 6,821,483 B2 | 11/2004 | McGarraugh | 422/58 | 6,889,069 B2 | 5/2005 | Routt | 600/319 |
| 6,823,750 B2 | 11/2004 | Hodges | 73/864.72 | 6,890,319 B1 | 5/2005 | Crocker | 604/131 |
| 6,825,047 B1 | 11/2004 | Woudenberg | 436/518 | 6,890,421 B2 | 5/2005 | Ohara | 205/777.5 |
| 6,827,250 B2 | 12/2004 | Uhland | 228/110.1 | 6,890,484 B2 | 5/2005 | Bautista | 422/58 |
| 6,827,829 B2 | 12/2004 | Kawanaka | 204/403.02 | 6,891,936 B2 | 5/2005 | Kai | 379/106.02 |
| 6,829,507 B1 | 12/2004 | Lidman | 607/19 | 6,892,085 B2 | 5/2005 | McIvor | 600/347 |
| 6,830,551 B1 | 12/2004 | Uchigaki | 600/584 | 6,893,396 B2 | 5/2005 | Schulze | 600/300 |
| 6,830,668 B2 | 12/2004 | Musho | 204/400 | 6,893,545 B2 | 5/2005 | Gotoh | 204/403.5 |
| 6,830,669 B2 | 12/2004 | Miyazaki | 204/409 | 6,893,552 B1 | 5/2005 | Wang | 205/777.5 |
| 6,830,934 B1 | 12/2004 | Harding | 436/166 | 6,895,263 B2 | 5/2005 | Shin | 600/316 |
| 6,833,540 B2 | 12/2004 | MacKenzie | 250/214 | 6,895,264 B2 | 5/2005 | Rice | 600/319 |
| 6,835,184 B1 | 12/2004 | Sage | 604/46 | 6,895,265 B2 | 5/2005 | Silver | 600/345 |
| 6,835,553 B2 | 12/2004 | Han | 435/14 | 6,896,793 B2 | 5/2005 | Erdosy | 205/775 |
| 6,835,570 B2 | 12/2004 | Patel | 436/8 | 6,897,788 B2 | 5/2005 | Khair | 340/870.16 |
| 6,837,858 B2 | 1/2005 | Cunningham | 600/573 | 6,902,905 B2 | 6/2005 | Burson | 435/14 |
| 6,837,976 B2 | 1/2005 | Cai | 204/403.14 | 6,904,301 B2 | 6/2005 | Raskas | 600/310 |
| 6,837,988 B2 | 1/2005 | Leong | 205/792 | 6,905,733 B2 | 6/2005 | Russell | 427/393.5 |
| 6,840,912 B2 | 1/2005 | Kloepfer | 600/583 | 6,908,008 B2 | 6/2005 | Pugh | 221/135 |
| 6,841,052 B2 | 1/2005 | Musho | 204/401 | 6,908,535 B2 | 6/2005 | Rankin | 204/406 |
| 6,843,254 B2 | 1/2005 | Tapper | 128/898 | 6,908,591 B2 | 6/2005 | MacPhee | 422/22 |
| 6,843,902 B1 | 1/2005 | Penner | 205/76 | 6,908,593 B1 | 6/2005 | Shartle | 422/58 |
| 6,844,149 B2 | 1/2005 | Goldman | 435/4 | 6,911,130 B2 | 6/2005 | Brenneman | 204/400 |
| 6,847,451 B2 | 1/2005 | Pugh | 356/436 | 6,911,131 B2 | 6/2005 | Miyazaki | 204/403.14 |
| 6,849,052 B2 | 2/2005 | Uchigaki | 600/584 | 6,911,621 B2 | 6/2005 | Bhullar | 219/121.69 |

| Patent | Date | Name | Ref |
|---|---|---|---|
| 6,911,937 B1 | 6/2005 | Sparrow | 342/188 |
| 6,913,210 B2 | 7/2005 | Baasch | 239/407 |
| 6,913,668 B2 | 7/2005 | Matzinger | 156/256 |
| 6,916,410 B2 | 7/2005 | Katsuki | 204/403 |
| 6,918,901 B1 | 7/2005 | Theeuwes | 604/500 |
| 6,918,918 B1 | 7/2005 | Schraga | 606/182 |
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |
| 6,925,393 B1 | 8/2005 | Kalatz | 702/27 |
| 6,929,631 B1 | 8/2005 | Brugger | 604/502 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,939,685 B2 | 9/2005 | Ouyang | 435/26 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,953,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |
| 6,960,287 B2 | 11/2005 | Charlton | 205/775 |
| 6,960,289 B2 | 11/2005 | Hodges | 205/778 |
| 6,960,323 B2 | 11/2005 | Guo | 422/60 |
| 6,964,871 B2 | 11/2005 | Bell | 436/95 |
| 6,965,791 B1 | 11/2005 | Hitchcock | 600/345 |
| 6,966,880 B2 | 11/2005 | Boecker | 600/583 |
| 6,966,977 B2 | 11/2005 | Hasegawa | 204/403.07 |
| 6,967,105 B2 | 11/2005 | Nomura | 436/169 |
| 6,968,375 B1 | 11/2005 | Brown | 709/224 |
| 6,969,359 B2 | 11/2005 | Duchon | 600/583 |
| 6,969,450 B2 | 11/2005 | Taniike | 204/403.01 |
| 6,969,451 B2 | 11/2005 | Shin | 204/412 |
| 6,973,706 B2 | 12/2005 | Say | 29/595 |
| 6,975,893 B2 | 12/2005 | Say | 600/347 |
| 6,977,032 B2 | 12/2005 | Hasegawa | 204/403.05 |
| 6,977,722 B2 | 12/2005 | Wohlstadter et al. | 356/246 |
| 6,979,544 B2 | 12/2005 | Keen | 435/6 |
| 6,979,571 B2 | 12/2005 | Modzelewski | 436/164 |
| 6,982,027 B2 | 1/2006 | Yagi | 204/403.06 |
| 6,982,431 B2 | 1/2006 | Modlin | 250/573 |
| 6,983,176 B2 | 1/2006 | Gardner | 600/310 |
| 6,983,177 B2 | 1/2006 | Rule | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 | 1/2006 | Roe | 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/345 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,210 B2 | 5/2006 | Hodges | 205/792 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,043,821 B2 | 5/2006 | Hodges | 29/594 |
| 7,044,911 B2 | 5/2006 | Drinan | 600/300 |
| 7,045,046 B2 | 5/2006 | Chambers | 204/400 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,087 B2 | 5/2006 | Jenny | 435/13 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D522,656 S | 6/2006 | Orr | D24/169 |
| D523,555 S | 6/2006 | Loerwald | D24/146 |
| 7,056,425 B2 | 6/2006 | Hasegawa | 204/403.04 |
| 7,056,495 B2 | 6/2006 | Roser | 424/45 |
| 7,058,437 B2 | 6/2006 | Buse | 600/347 |
| 7,059,352 B2 | 6/2006 | Bohm | 137/828 |
| 7,060,059 B2 | 6/2006 | Keith | 604/504 |
| 7,060,168 B2 | 6/2006 | Taniike | 204/403.04 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |

| Patent No. | Date | Name | Class |
|---|---|---|---|
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,079,252 B1 | 7/2006 | Debreczeny | 356/451 |
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,006 B2 | 9/2006 | Shraga | 606/182 |
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,113,172 B2 | 9/2006 | Hohl | 345/168 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,550 B2 | 11/2006 | Groth | 206/366 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,034 B2 | 11/2006 | Eppstein | 604/22 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorczyk | 205/792 |
| 7,144,496 B2 | 12/2006 | Meserol | 205/792 |
| 7,144,709 B2 | 12/2006 | Ouyang | 435/7.9 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,156,117 B2 | 1/2007 | Bohm | 137/14 |
| 7,156,810 B2 | 1/2007 | Cho | 600/365 |
| 7,157,723 B2 | 1/2007 | Colvin | 250/458.1 |
| 7,160,251 B2 | 1/2007 | Neel | 600/365 |
| 7,160,313 B2 | 1/2007 | Galloway | 606/167 |
| 7,160,678 B1 | 1/2007 | Kayyem | 435/6 |
| 7,162,289 B2 | 1/2007 | Shah | 600/345 |
| 7,163,616 B2 | 1/2007 | Vreeke | 205/777.5 |
| 7,166,074 B2 | 1/2007 | Reghabi | 600/365 |
| 7,166,208 B2 | 1/2007 | Zweig | 205/777.5 |
| 7,167,734 B2 | 1/2007 | Khalil | 600/310 |
| 7,167,735 B2 | 1/2007 | Uchida | 600/310 |
| 7,167,818 B2 | 1/2007 | Brown | 703/11 |
| 7,169,116 B2 | 1/2007 | Day | 600/583 |
| 7,169,117 B2 | 1/2007 | Allen | 600/584 |
| 7,169,289 B2 | 1/2007 | Schulein | 205/777.5 |
| 7,169,600 B2 | 1/2007 | Hoss | 435/287.1 |
| 7,172,728 B2 | 2/2007 | Otake | 422/58 |
| 7,174,199 B2 | 2/2007 | Berner | 600/347 |
| 7,175,641 B1 | 2/2007 | Schraga | 606/181 |
| 7,175,642 B2 | 2/2007 | Briggs | 606/181 |
| 7,179,233 B2 | 2/2007 | Chang | 600/584 |
| 7,182,910 B2 | 2/2007 | Allen | 422/50 |
| 7,183,068 B2 | 2/2007 | Burson | 435/14 |
| 7,183,102 B2 | 2/2007 | Monfre | 200/51.09 |
| 7,188,034 B2 | 3/2007 | Staib | 702/22 |
| 7,189,576 B2 | 3/2007 | Fukuoka | 436/170 |
| 7,190,988 B2 | 3/2007 | Say | 600/345 |
| 7,192,405 B2 | 3/2007 | DeNuzzio | 600/583 |
| 7,192,450 B2 | 3/2007 | Brauker | 623/23.76 |
| 7,195,704 B2 | 3/2007 | Kermani | 205/777.5 |
| 7,198,606 B2 | 4/2007 | Boecker | 600/583 |
| 7,199,594 B2 | 4/2007 | Kermani | 324/663 |
| 7,202,854 B2 | 4/2007 | Hohl | 345/168 |
| 7,206,620 B2 | 4/2007 | Erickson | 600/310 |
| 7,206,623 B2 | 4/2007 | Blank | 600/344 |
| D542,681 S | 5/2007 | Young | D10/80 |
| 7,211,052 B2 | 5/2007 | Roe | 600/584 |
| 7,211,096 B2 | 5/2007 | Kuhr | 606/182 |
| 7,212,925 B2 | 5/2007 | Genshaw | 702/23 |
| 7,213,720 B2 | 5/2007 | Giraud | 220/839 |
| 7,215,982 B2 | 5/2007 | Oshima | 600/310 |
| 7,215,983 B2 | 5/2007 | Cho | 600/316 |
| 7,223,248 B2 | 5/2007 | Erickson | 600/584 |
| 7,225,008 B1 | 5/2007 | Ward | 600/345 |
| D543,878 S | 6/2007 | Castillo | D10/81 |
| D545,438 S | 6/2007 | Huang | D24/186 |
| 7,225,535 B2 | 6/2007 | Feldman | 29/831 |
| 7,226,414 B2 | 6/2007 | Ballerstadt | 600/365 |
| 7,226,461 B2 | 6/2007 | Boecker | 606/181 |
| 7,226,978 B2 | 6/2007 | Tapsak | 525/296 |
| 7,227,156 B2 | 6/2007 | Colvin | 250/458.1 |
| 7,228,159 B2 | 6/2007 | Petersson | 600/316 |
| 7,228,162 B2 | 6/2007 | Ward | 600/345 |
| 7,228,163 B2 | 6/2007 | Ackerman | 600/347 |
| 7,229,458 B2 | 6/2007 | Boecker | 606/181 |
| 7,232,451 B2 | 6/2007 | Boecker | 606/181 |
| 7,232,510 B2 | 6/2007 | Miyazaki | 204/403.1 |
| 7,233,816 B2 | 6/2007 | Blank | 600/310 |
| 7,235,056 B2 | 6/2007 | Duchon | 600/583 |
| 7,235,170 B2 | 6/2007 | Watanabe | 205/777.5 |
| 7,235,378 B2 | 6/2007 | Yonehara | 435/14 |
| 7,236,812 B1 | 6/2007 | Ballerstadt | 600/316 |
| 7,236,814 B2 | 6/2007 | Shioi | 600/344 |
| D545,705 S | 7/2007 | Voege | D10/81 |
| D546,216 S | 7/2007 | Bolognesi | D10/81 |
| D546,218 S | 7/2007 | Grasso | D10/81 |
| 7,238,192 B2 | 7/2007 | List | 606/182 |
| 7,238,534 B1 | 7/2007 | Zimmer | 436/169 |
| 7,241,265 B2 | 7/2007 | Cummings | 600/300 |
| 7,244,264 B2 | 7/2007 | Roe | 606/181 |
| 7,244,265 B2 | 7/2007 | Freeman | 606/181 |
| 7,244,266 B2 | 7/2007 | Garthe | 606/181 |
| 7,247,138 B2 | 7/2007 | Reghabi | 600/365 |
| 7,247,144 B2 | 7/2007 | Douglas | 600/583 |
| 7,250,037 B2 | 7/2007 | Shermer | 604/134 |
| 7,250,056 B2 | 7/2007 | Hamamoto | 606/181 |
| 7,250,095 B2 | 7/2007 | Black | 204/403.14 |
| 7,250,105 B1 | 7/2007 | Davies | 205/777.5 |
| 7,251,513 B2 | 7/2007 | Kondoh | 600/310 |
| 7,251,514 B2 | 7/2007 | Cho | 600/316 |
| 7,251,515 B2 | 7/2007 | Cho | 600/316 |
| 7,251,516 B2 | 7/2007 | Walker | 600/316 |
| 7,251,517 B2 | 7/2007 | Cho | 600/316 |
| 7,251,518 B2 | 7/2007 | Herrmann | 600/322 |
| 7,252,804 B2 | 8/2007 | Miyashita | 422/104 |
| 7,254,426 B2 | 8/2007 | Cho | 600/316 |

| Patent No. | Date | Name | Ref |
|---|---|---|---|
| 7,254,427 B2 | 8/2007 | Cho | 600/316 |
| 7,254,428 B2 | 8/2007 | Cho | 600/316 |
| 7,254,429 B2 | 8/2007 | Schurman | 600/316 |
| 7,254,430 B2 | 8/2007 | Cho | 600/316 |
| 7,254,432 B2 | 8/2007 | Fine | 600/335 |
| 7,258,673 B2 | 8/2007 | Racchini | 600/583 |
| 7,258,693 B2 | 8/2007 | Freeman | 606/181 |
| 7,262,061 B2 | 8/2007 | Petrich | 436/169 |
| 7,264,139 B2 | 9/2007 | Brickwood | 221/270 |
| 7,264,627 B2 | 9/2007 | Perez | 606/181 |
| 7,266,400 B2 | 9/2007 | Fine | 600/319 |
| 7,267,665 B2 | 9/2007 | Steil | 604/131 |
| 7,267,750 B2 | 9/2007 | Watanabe | 204/403.04 |
| 7,270,247 B2 | 9/2007 | Charlton | 221/59 |
| 7,271,912 B2 | 9/2007 | Sterling | 356/436 |
| 7,273,484 B2 | 9/2007 | Thoes | 606/181 |
| 7,276,027 B2 | 10/2007 | Haar | 600/309 |
| 7,276,029 B2 | 10/2007 | Goode | 600/365 |
| 7,276,146 B2 | 10/2007 | Wilsey | 205/792 |
| 7,276,147 B2 | 10/2007 | Wilsey | 205/792 |
| 7,276,380 B2 | 10/2007 | Fukuyama | 436/164 |
| 7,277,740 B2 | 10/2007 | Rohleder | 600/316 |
| 7,278,983 B2 | 10/2007 | Ireland | 604/66 |
| 7,279,130 B2 | 10/2007 | Brown | 422/64 |
| 7,282,058 B2 | 10/2007 | Levin | 606/181 |
| 7,287,318 B2 | 10/2007 | Bhullar | 29/825 |
| 7,288,073 B2 | 10/2007 | Effenhauser | 600/584 |
| 7,288,102 B2 | 10/2007 | Griffin | 606/182 |
| 7,288,174 B2 | 10/2007 | Cui | 204/403.14 |
| 7,289,836 B2 | 10/2007 | Colvin, Jr. | 600/316 |
| 7,291,117 B2 | 11/2007 | Boecker | 600/583 |
| 7,291,159 B2 | 11/2007 | Schmelzeisen-Redeker | 606/181 |
| 7,291,256 B2 | 11/2007 | Teodorezyk | 205/777.5 |
| 7,291,497 B2 | 11/2007 | Holmes | 435/287.2 |
| 7,294,246 B2 | 11/2007 | Gundel | 204/403.14 |
| 7,295,867 B2 | 11/2007 | Berner | 600/345 |
| 7,297,122 B2 | 11/2007 | Boecker | 600/583 |
| 7,297,151 B2 | 11/2007 | Boecker | 606/181 |
| 7,297,152 B2 | 11/2007 | Fukuzawa | 606/181 |
| 7,297,241 B2 | 11/2007 | Kontschieder | 204/403.01 |
| 7,297,248 B2 | 11/2007 | Bae | 205/777.5 |
| 7,297,627 B2 | 11/2007 | Shah | 438/622 |
| 7,299,079 B2 | 11/2007 | Rebec | 600/316 |
| 7,299,080 B2 | 11/2007 | Acosta | 600/316 |
| 7,299,081 B2 | 11/2007 | Mace | 600/345 |
| 7,299,082 B2 | 11/2007 | Feldman | 600/347 |
| 7,300,402 B2 | 11/2007 | Iliff | 600/300 |
| 7,301,629 B2 | 11/2007 | Bambot | 356/337 |
| 7,303,573 B2 | 12/2007 | D'Agostino | 606/181 |
| 7,303,726 B2 | 12/2007 | McAllister | 422/68.1 |
| 7,303,922 B2 | 12/2007 | Jeng | 436/164 |
| 7,305,896 B2 | 12/2007 | Howell | 73/864.02 |
| 7,306,560 B2 | 12/2007 | Iliff | 600/300 |
| 7,308,164 B1 | 12/2007 | Banks | 385/12 |
| 7,308,292 B2 | 12/2007 | Colvin | 600/310 |
| 7,310,542 B2 | 12/2007 | Jeon | 600/344 |
| 7,310,543 B2 | 12/2007 | Smart | 600/345 |
| 7,310,544 B2 | 12/2007 | Brister | 600/345 |
| 7,311,718 B2 | 12/2007 | Schraga | 606/181 |
| 7,311,812 B2 | 12/2007 | Forrow | 204/403.06 |
| 7,312,042 B1 | 12/2007 | Petyt | 435/7.1 |
| 7,313,425 B2 | 12/2007 | Finarov | 600/310 |
| 7,314,453 B2 | 1/2008 | Kuo | 600/584 |
| 7,315,752 B2 | 1/2008 | Kraemer | 600/316 |
| 7,316,700 B2 | 1/2008 | Alden | 606/181 |
| 7,316,766 B2 | 1/2008 | Chen | 204/403.01 |
| 7,316,929 B2 | 1/2008 | Purcell | 436/8 |
| 7,317,938 B2 | 1/2008 | Lorenz | 600/316 |
| 7,317,939 B2 | 1/2008 | Fine | 600/322 |
| 7,322,942 B2 | 1/2008 | Roe | 600/583 |
| 7,322,996 B2 | 1/2008 | Taylor | 606/181 |
| 7,322,997 B2 | 1/2008 | Shi | 606/181 |
| 7,322,998 B2 | 1/2008 | Kuhr | 606/182 |
| 7,323,098 B2 | 1/2008 | Miyashita | 205/777.5 |
| 7,323,141 B2 | 1/2008 | Kirchhevel | 422/68.1 |
| 7,323,315 B2 | 1/2008 | Marfurt | 435/7.25 |
| 7,324,012 B2 | 1/2008 | Mann | 340/870.07 |
| 7,328,052 B2 | 2/2008 | Samsoondar | 600/310 |
| 7,331,931 B2 | 2/2008 | Freeman | 600/583 |
| 7,335,292 B2 | 2/2008 | Hodges | 205/775 |
| 7,335,294 B2 | 2/2008 | Heller | 205/792 |
| 7,337,918 B2 | 3/2008 | Fowler | 221/65 |
| 7,338,639 B2 | 3/2008 | Burke | 422/82.1 |
| 7,343,188 B2 | 3/2008 | Sohrab | 600/345 |
| 7,344,499 B1 | 3/2008 | Prausnitz | 600/309 |
| 7,344,500 B2 | 3/2008 | Talbot | 600/365 |
| 7,344,507 B2 | 3/2008 | Briggs | 600/583 |
| 7,344,626 B2 | 3/2008 | Harding | 204/403.01 |
| 7,347,925 B2 | 3/2008 | Hsieh | 205/777.5 |
| 7,347,926 B2 | 3/2008 | Morita | 205/792 |
| 7,347,973 B2 | 3/2008 | Douglas | 422/61 |
| RE40,198 E | 4/2008 | Buck | |
| 7,351,213 B2 | 4/2008 | Wong | 600/584 |
| 7,351,323 B2 | 4/2008 | Iketaki | 205/777.5 |
| 7,351,375 B2 | 4/2008 | Noda | 422/82.01 |
| 7,351,770 B2 | 4/2008 | Liu | 525/283 |
| 7,357,808 B2 | 4/2008 | Kennedy | 606/181 |
| 7,357,851 B2 | 4/2008 | Reid | 204/403.04 |
| 7,361,182 B2 | 4/2008 | Fukuda | 606/181 |
| 7,361,307 B2 | 4/2008 | Schartle | 422/82.01 |
| 7,371,247 B2 | 5/2008 | Boecker | 606/181 |
| 7,372,277 B2 | 5/2008 | Diamond | 324/444 |
| 7,374,544 B2 | 5/2008 | Freeman | 600/583 |
| 7,374,546 B2 | 5/2008 | Roe | 600/583 |
| 7,378,007 B2 | 5/2008 | Moerman | 204/403.03 |
| 7,378,270 B2 | 5/2008 | Azarnia | 435/287.2 |
| 7,402,616 B2 | 7/2008 | Rodgers | 523/160 |
| 7,404,815 B2 | 7/2008 | Kollias | 604/501 |
| 7,410,468 B2 | 8/2008 | Freeman | 600/583 |
| 7,429,630 B2 | 9/2008 | Liu | 525/283 |
| 7,431,814 B2 | 10/2008 | Hodges | 204/403.02 |
| 7,431,820 B2 | 10/2008 | Hodges | 205/777.5 |
| 7,438,694 B2 | 10/2008 | Boozer | 600/583 |
| D579,652 S | 11/2008 | Lim | D3/201 |
| D579,653 S | 11/2008 | Lim | D3/201 |
| 7,462,265 B2 | 12/2008 | Leach | 204/403.14 |
| 7,465,380 B2 | 12/2008 | Rodgers | 204/403.14 |
| 7,468,125 B2 | 12/2008 | Kraft | 205/792 |
| D585,314 S | 1/2009 | Schvetz | D10/78 |
| 7,473,264 B2 | 1/2009 | Allen | 606/181 |
| 7,474,390 B2 | 1/2009 | Robinson | 356/42 |
| 7,474,391 B2 | 1/2009 | Baskeyfield | 356/42 |
| 7,481,776 B2 | 1/2009 | Boecker | 600/583 |
| 7,481,818 B2 | 1/2009 | Allen | 606/181 |
| D586,465 S | 2/2009 | Faulkner | D24/146 |
| D586,466 S | 2/2009 | Smith | D24/186 |
| D586,678 S | 2/2009 | Schvetz | D10/81 |
| D586,916 S | 2/2009 | Faulkner | D24/146 |
| 7,485,128 B2 | 2/2009 | Boecker | 606/181 |
| 7,491,178 B2 | 2/2009 | Boecker | 600/583 |
| 7,498,132 B2 | 3/2009 | Yu | 435/6 |
| 7,501,052 B2 | 3/2009 | Iyengar | 205/777.5 |
| 7,501,093 B2 | 3/2009 | Demelo | 422/58 |
| 7,521,019 B2 | 4/2009 | Polak | 422/82.06 |
| 7,524,293 B2 | 4/2009 | Freeman | 600/583 |
| 7,537,571 B2 | 5/2009 | Freeman | 600/583 |
| 7,547,287 B2 | 6/2009 | Boecker | 600/583 |
| 7,548,772 B2 | 6/2009 | Shartle | 600/345 |
| 7,553,511 B2 | 6/2009 | Hleong | 427/2.28 |
| 7,563,232 B2 | 7/2009 | Freeman | 600/583 |
| D598,126 S | 8/2009 | Alvarez-Icaza | D24/225 |
| 7,572,356 B2 | 8/2009 | Rodgers | 204/403.05 |
| 7,575,558 B2 | 8/2009 | Boecker | 600/573 |
| D600,349 S | 9/2009 | Bell | D24/169 |
| D600,812 S | 9/2009 | Lei | D24/169 |
| D600,813 S | 9/2009 | Bell | D24/169 |
| D601,255 S | 9/2009 | Schvetz | D24/169 |
| D601,258 S | 9/2009 | Bell | D24/169 |
| 7,582,063 B2 | 9/2009 | Wurster | 600/584 |
| 7,582,099 B2 | 9/2009 | Freeman | 606/181 |
| 7,586,590 B2 | 9/2009 | Baskeyfield | 356/42 |
| 7,588,670 B2 | 9/2009 | Rodgers | 204/403.14 |
| 7,589,828 B2 | 9/2009 | Robinson | 356/42 |
| 7,592,151 B2 | 9/2009 | Liu | 435/14 |
| 7,593,097 B2 | 9/2009 | Robinson | 356/42 |
| 7,604,592 B2 | 10/2009 | Freeman | 600/309 |
| 7,604,722 B2 | 10/2009 | Hodges | 204/403.02 |
| 7,608,175 B2 | 10/2009 | Hodges | 204/403.02 |

| | | | |
|---|---|---|---|
| 7,618,522 B2 | 11/2009 | Davies | 204/403.14 |
| 7,648,468 B2 | 1/2010 | Boecker | 600/583 |
| 7,648,469 B2 | 1/2010 | Boecker | 600/583 |
| 7,653,492 B2 | 1/2010 | Davies | 702/22 |
| 7,654,127 B2 | 2/2010 | Krulevitch | 73/1.16 |
| 7,655,119 B2 | 2/2010 | Davies | 204/403.14 |
| 7,665,303 B2 | 2/2010 | Bohm | 60/643 |
| 7,666,287 B2 | 2/2010 | Zhao | 204/600 |
| D611,151 S | 3/2010 | Lei | D24/169 |
| D611,372 S | 3/2010 | Salter | D10/81 |
| D611,489 S | 3/2010 | Bell | D14/486 |
| D611,853 S | 3/2010 | Salter | D10/81 |
| D612,274 S | 3/2010 | Heidemann | D10/78 |
| D612,275 S | 3/2010 | Salter | D10/81 |
| D612,279 S | 3/2010 | Heidemann | D10/103 |
| 7,674,232 B2 | 3/2010 | Boecker | 600/583 |
| 7,682,318 B2 | 3/2010 | Alden | 600/583 |
| 7,713,214 B2 | 5/2010 | Freeman et al. | 600/583 |
| 7,833,172 B2 | 11/2010 | Hein et al. | 600/583 |
| 7,901,365 B2 | 3/2011 | Freeman et al. | 600/583 |
| 2001/0011157 A1 | 8/2001 | Latterell | 600/576 |
| 2001/0016682 A1 | 8/2001 | Berner | 600/345 |
| 2001/0017269 A1 | 8/2001 | Heller | 205/777.5 |
| 2001/0018353 A1 | 8/2001 | Ishigaki | 455/566 |
| 2001/0027328 A1 | 10/2001 | Lum | 606/186 |
| 2001/0031931 A1 | 10/2001 | Cunningham | 600/573 |
| 2001/0037355 A1 | 11/2001 | Britt | 709/201 |
| 2001/0042004 A1 | 11/2001 | Taub | 705/11 |
| 2001/0045355 A1 | 11/2001 | Gephart | 204/400 |
| 2001/0054319 A1 | 12/2001 | Heller | 73/849 |
| 2002/0002326 A1 | 1/2002 | Causey | 600/300 |
| 2002/0002344 A1 | 1/2002 | Douglas | 600/583 |
| 2002/0004196 A1 | 1/2002 | Whitson | 600/573 |
| 2002/0016568 A1 | 2/2002 | Lebel | 604/131 |
| 2002/0016606 A1 | 2/2002 | Moerman | 606/181 |
| 2002/0016923 A1 | 2/2002 | Knaus | 713/200 |
| 2002/0019606 A1 | 2/2002 | Lebel | 604/66 |
| 2002/0019747 A1 | 2/2002 | Ware | 705/2 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040208 A1 | 4/2002 | Flaherty | 604/288.01 |
| 2002/0040230 A1 | 4/2002 | Kuhr | 606/181 |
| 2002/0042090 A1 | 4/2002 | Heller | 435/14 |
| 2002/0042594 A1 | 4/2002 | Lum | 604/117 |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |
| 2002/0057993 A1 | 5/2002 | Maisey | 422/82.01 |
| 2002/0058902 A1 | 5/2002 | Kollias et al. | 604/20 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0082543 A1 | 6/2002 | Park | 604/21 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0099308 A1 | 7/2002 | Bojan | 600/573 |
| 2002/0103499 A1 | 8/2002 | Perez | 606/182 |
| 2002/0120216 A1 | 8/2002 | Fritz | 600/583 |
| 2002/0120261 A1 | 8/2002 | Morris | 606/41 |
| 2002/0123335 A1 | 9/2002 | Luna | 455/419 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0148739 A2 | 10/2002 | Liamos | 205/787 |
| 2002/0156355 A1 | 10/2002 | Gough | 600/345 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0169393 A1 | 11/2002 | Cunningham | 600/573 |
| 2002/0169394 A1 | 11/2002 | Eppstein | 600/573 |
| 2002/0176984 A1 | 11/2002 | Smart | 428/336 |
| 2002/0177761 A1 | 11/2002 | Orloff | 600/309 |
| 2002/0177763 A1 | 11/2002 | Burns | 600/345 |
| 2002/0188224 A1 | 12/2002 | Roe | 600/584 |
| 2003/0014010 A1 | 1/2003 | Carpenter | 604/117 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | |
| 2003/0028126 A1 | 2/2003 | List | 600/583 |
| 2003/0032077 A1 | 2/2003 | Itoh | 435/14 |
| 2003/0038047 A1 | 2/2003 | Sleva | 206/370 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0057391 A1 | 3/2003 | Krulevitch | 251/11 |
| 2003/0060730 A1 | 3/2003 | Perez | 600/576 |
| 2003/0069509 A1 | 4/2003 | Matzinger et al. | 600/504 |
| 2003/0069753 A1 | 4/2003 | Brown | 705/2 |
| 2003/0072647 A1 | 4/2003 | Lum | 415/1 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0109860 A1 | 6/2003 | Black | 606/10 |
| 2003/0111357 A1 | 6/2003 | Black | 205/775 |
| 2003/0113827 A1 | 6/2003 | Burkoth | 435/14 |
| 2003/0116447 A1 | 6/2003 | Surridge | 205/777.5 |
| 2003/0120297 A1 | 6/2003 | Beyerlein | 606/185 |
| 2003/0135333 A1 | 7/2003 | Aceti | 702/31 |
| 2003/0136189 A1 | 7/2003 | Lauman | 73/304 C |
| 2003/0139653 A1 | 7/2003 | Manser | 600/300 |
| 2003/0143113 A2 | 7/2003 | Yuzhakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149377 A1 | 8/2003 | Erickson | 600/573 |
| 2003/0153900 A1 | 8/2003 | Aceti | 604/890.1 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0191376 A1 | 10/2003 | Samuels | 600/309 |
| 2003/0191415 A1 | 10/2003 | Moerman | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199895 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |

| Pub. No. | Date | Inventor | Class |
|---|---|---|---|
| 2003/0210811 A1 | 11/2003 | Dubowsky | 382/128 |
| 2003/0211619 A1 | 11/2003 | Olson et al. | 436/44 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | Yuzhakov | 600/584 |
| 2003/0212347 A1 | 11/2003 | Sohrab | 600/584 |
| 2003/0212379 A1 | 11/2003 | Bylund | 604/504 |
| 2003/0212423 A1 | 11/2003 | Pugh | 606/181 |
| 2003/0212424 A1 | 11/2003 | Briggs | 606/181 |
| 2003/0212579 A1 | 11/2003 | Brown | 705/2 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe | 606/182 |
| 2003/0225430 A1 | 12/2003 | Schraga | 606/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/573 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0019259 A1 | 1/2004 | Brown | 600/300 |
| 2004/0026243 A1 | 2/2004 | Davies | 204/403.14 |
| 2004/0026244 A1 | 2/2004 | Hodges | 204/409 |
| 2004/0030353 A1 | 2/2004 | Schmelzeisen-Redeker | 606/2 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0049219 A1 | 3/2004 | Briggs | 606/181 |
| 2004/0049220 A1 | 3/2004 | Boecker | 606/181 |
| 2004/0050694 A1 | 3/2004 | Yang | 204/403.02 |
| 2004/0054267 A1 | 3/2004 | Feldman | 600/316 |
| 2004/0055898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0069657 A1 | 4/2004 | Hodges | 205/787 |
| 2004/0087990 A1 | 5/2004 | Boecker | 606/181 |
| 2004/0092842 A1 | 5/2004 | Boecker | 600/575 |
| 2004/0092994 A1 | 5/2004 | Briggs | 606/181 |
| 2004/0092995 A1 | 5/2004 | Boecker | 606/181 |
| 2004/0096991 A1 | 5/2004 | Zhang | 436/518 |
| 2004/0098009 A1 | 5/2004 | Boecker | 606/181 |
| 2004/0098010 A1 | 5/2004 | Davison | 606/181 |
| 2004/0102803 A1 | 5/2004 | Boecker | 606/183 |
| 2004/0106855 A1 | 6/2004 | Brown | 600/301 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0107116 A1 | 6/2004 | Brown | 705/2 |
| 2004/0115754 A1 | 6/2004 | Chang | 435/14 |
| 2004/0115831 A1 | 6/2004 | Meathrel | 436/514 |
| 2004/0116780 A1 | 6/2004 | Brown | 600/300 |
| 2004/0116829 A1 | 6/2004 | Raney | 600/573 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0137640 A1 | 7/2004 | Hirao | 436/514 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Keheiri | 606/182 |
| 2004/0167383 A1 | 8/2004 | Kim | 600/365 |
| 2004/0171057 A1 | 9/2004 | Mauze | 435/6 |
| 2004/0171968 A1 | 9/2004 | Katsuki | 600/583 |
| 2004/0172002 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.06 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koilke | 606/181 |
| 2004/0193201 A1 | 9/2004 | Kim | 606/181 |
| 2004/0193377 A1 | 9/2004 | Brown | 702/19 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0199409 A1 | 10/2004 | Brown | 705/3 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219500 A1 | 11/2004 | Brown | 434/307 R |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220564 A1 | 11/2004 | Ho | 606/47 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn et al. | 606/181 |
| 2004/0231983 A1 | 11/2004 | Shen | 204/403.01 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |

| Publication No. | Date | Inventor | Class |
|---|---|---|---|
| 2004/0236268 A1 | 11/2004 | Mitragotri | 604/20 |
| 2004/0236362 A1 | 11/2004 | Schraga | 606/181 |
| 2004/0238357 A1 | 12/2004 | Bhullar | 204/400 |
| 2004/0238358 A1 | 12/2004 | Forrow | 204/403.01 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249254 A1 | 12/2004 | Racchini | 600/347 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/345 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | LeVaughn | 422/56 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode, Jr. | 600/365 |
| 2005/0027211 A1 | 2/2005 | Kuhr | 600/583 |
| 2005/0027562 A1 | 2/2005 | Brown | 705/2 |
| 2005/0033340 A1 | 2/2005 | Lipoma | 606/181 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Nakahara et al. | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Schraga | 606/182 |
| 2005/0038465 A1 | 2/2005 | Schraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 3/403.2 |
| 2005/0049472 A1 | 3/2005 | Manda | 600/345 |
| 2005/0049473 A1 | 3/2005 | Desai | 600/347 |
| 2005/0050859 A1 | 3/2005 | Coppeta | 53/471 |
| 2005/0054082 A1 | 3/2005 | Pachl | 435/287.2 |
| 2005/0054908 A1 | 3/2005 | Blank | 600/316 |
| 2005/0059872 A1 | 3/2005 | Shartle | 600/347 |
| 2005/0059895 A1 | 3/2005 | Brown | 600/481 |
| 2005/0060194 A1 | 3/2005 | Brown | 705/2 |
| 2005/0061668 A1 | 3/2005 | Brenneman et al. | 204/403.01 |
| 2005/0064528 A1 | 3/2005 | Kwon et al. | 435/14 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Gundel | 204/403.2 |
| 2005/0098433 A1 | 5/2005 | Gundel | 204/403.2 |
| 2005/0098434 A1 | 5/2005 | Gundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112712 A1 | 5/2005 | Ouyang et al. | 435/14 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowiz | 705/1 |
| 2005/0114444 A1 | 5/2005 | Brown | 709/203 |
| 2005/0118056 A1 | 6/2005 | Swanson | 423/23 |
| 2005/0118062 A1 | 6/2005 | Otake | 422/68.1 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137535 A1 | 6/2005 | Prausnitz | 604/173 |
| 2005/0137536 A1 | 6/2005 | Gonnelli | 604/264 |
| 2005/0140659 A1 | 6/2005 | Hohl | 345/169 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |

| Pub. No. | Date | Name | Class |
|---|---|---|---|
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0149090 A1 | 7/2005 | Morita | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169810 A1 | 8/2005 | Hagen | 422/102 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0176153 A1 | 8/2005 | O'hara | 436/70 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Saito | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205136 A1 | 9/2005 | Freeman | 137/554 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232258 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245846 A1 | 11/2005 | Casey | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/181 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030050 A1 | 2/2006 | Milne | 436/67 |
| 2006/0030761 A1 | 2/2006 | Raskas | 600/316 |
| 2006/0030788 A1 | 2/2006 | Wong | 600/583 |
| 2006/0034728 A1 | 2/2006 | Kloepfer | 422/68.1 |
| 2006/0037859 A1 | 2/2006 | Hodges | 204/400 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |

| | | | |
|---|---|---|---|
| 2006/0094947 A1 | 5/2006 | Kovatchev ............ 600/365 |
| 2006/0094985 A1 | 5/2006 | Aceti .................... 600/575 |
| 2006/0094986 A1 | 5/2006 | Neel ..................... 600/583 |
| 2006/0095061 A1 | 5/2006 | Trautman .............. 606/185 |
| 2006/0096859 A1 | 5/2006 | Lau .................. 204/403.14 |
| 2006/0099107 A1 | 5/2006 | Yamamoto ............. 422/57 |
| 2006/0099703 A1 | 5/2006 | Choi .................. 435/287.1 |
| 2006/0100542 A9 | 5/2006 | Wong ................... 600/583 |
| 2006/0100543 A1 | 5/2006 | Raney .................. 600/583 |
| 2006/0100654 A1 | 5/2006 | Fukuda ................ 606/181 |
| 2006/0100655 A1 | 5/2006 | Leong .................. 606/181 |
| 2006/0100656 A1 | 5/2006 | Olsen ................... 606/181 |
| 2006/0106373 A1 | 5/2006 | Cahir ......................... 606/9 |
| 2006/0108236 A1 | 5/2006 | Kasielke ............... 205/792 |
| 2006/0113187 A1 | 6/2006 | Deng ................ 204/403.01 |
| 2006/0115857 A1 | 6/2006 | Keen ..................... 435/7.1 |
| 2006/0116562 A1 | 6/2006 | Acosta ................. 600/316 |
| 2006/0116704 A1 | 6/2006 | Ashby .................. 606/167 |
| 2006/0116705 A1 | 6/2006 | Schraga ................ 606/181 |
| 2006/0119362 A1 | 6/2006 | Kermani ............... 324/324 |
| 2006/0121547 A1 | 6/2006 | McIntire ................. 435/14 |
| 2006/0121625 A1 | 6/2006 | Clemens ............... 436/514 |
| 2006/0121759 A1 | 6/2006 | Kasai ................... 439/188 |
| 2006/0122099 A1 | 6/2006 | Aoki ......................... 514/3 |
| 2006/0122536 A1 | 6/2006 | Haar .................... 600/581 |
| 2006/0129065 A1 | 6/2006 | Matsumoto ........... 600/583 |
| 2006/0129172 A1 | 6/2006 | Crossman ............. 606/181 |
| 2006/0129173 A1 | 6/2006 | Wilkinson ............ 606/181 |
| 2006/0134713 A1 | 6/2006 | Rylatt .................. 435/7.92 |
| 2006/0140457 A1 | 6/2006 | Simshauser .......... 382/124 |
| 2006/0144704 A1 | 7/2006 | Ghesquiere ...... 204/403.01 |
| 2006/0151323 A1 | 7/2006 | Cho ................. 204/403.04 |
| 2006/0151342 A1 | 7/2006 | Yaguchi ................ 206/306 |
| 2006/0155215 A1 | 7/2006 | Cha ....................... 600/583 |
| 2006/0155316 A1 | 7/2006 | Perez .................... 606/181 |
| 2006/0155317 A1 | 7/2006 | List ...................... 606/181 |
| 2006/0156796 A1 | 7/2006 | Burke .................. 73/61.44 |
| 2006/0157362 A1 | 7/2006 | Schraga ................ 206/363 |
| 2006/0160100 A1 | 7/2006 | Gao ......................... 435/6 |
| 2006/0161078 A1 | 7/2006 | Schraga ................ 600/583 |
| 2006/0161194 A1 | 7/2006 | Freeman .............. 606/185 |
| 2006/0163061 A1 | 7/2006 | Hodges ................. 204/401 |
| 2006/0166302 A1 | 7/2006 | Clarke .................... 435/25 |
| 2006/0167382 A1 | 7/2006 | Deshmukh ........... 600/583 |
| 2006/0169599 A1 | 8/2006 | Feldman ............... 205/792 |
| 2006/0173254 A1 | 8/2006 | Acosta ................. 600/316 |
| 2006/0173255 A1 | 8/2006 | Acosta ................. 600/316 |
| 2006/0173379 A1 | 8/2006 | Rasch-Menges ..... 600/583 |
| 2006/0173380 A1 | 8/2006 | Hoenes ................. 600/583 |
| 2006/0173478 A1 | 8/2006 | Schraga ................ 606/181 |
| 2006/0175216 A1 | 8/2006 | Freeman .............. 206/363 |
| 2006/0178573 A1 | 8/2006 | Kermani ............... 600/347 |
| 2006/0178599 A1 | 8/2006 | Faupel .................. 600/578 |
| 2006/0178600 A1 | 8/2006 | Kennedy .............. 600/584 |
| 2006/0178686 A1 | 8/2006 | Schraga ................ 606/181 |
| 2006/0178687 A1 | 8/2006 | Freeman .............. 606/181 |
| 2006/0178688 A1 | 8/2006 | Freeman .............. 606/181 |
| 2006/0178689 A1 | 8/2006 | Freeman .............. 606/181 |
| 2006/0178690 A1 | 8/2006 | Freeman .............. 606/181 |
| 2006/0183871 A1 | 8/2006 | Ward ................... 525/464 |
| 2006/0183983 A1 | 8/2006 | Acosta ................. 600/316 |
| 2006/0184065 A1 | 8/2006 | Deshmukh ........... 600/583 |
| 2006/0184101 A1 | 8/2006 | Srinivasan .............. 604/68 |
| 2006/0188395 A1 | 8/2006 | Taniike .................. 422/57 |
| 2006/0189895 A1 | 8/2006 | Neel ..................... 600/584 |
| 2006/0191787 A1 | 8/2006 | Wang ................... 204/400 |
| 2006/0195023 A1 | 8/2006 | Acosta ................. 600/316 |
| 2006/0195047 A1 | 8/2006 | Freeman .............. 600/583 |
| 2006/0195128 A1 | 8/2006 | Alden ................... 606/181 |
| 2006/0195129 A1 | 8/2006 | Freeman .............. 606/181 |
| 2006/0195130 A1 | 8/2006 | Freeman .............. 606/181 |
| 2006/0195131 A1 | 8/2006 | Freeman .............. 606/181 |
| 2006/0195132 A1 | 8/2006 | Freeman .............. 606/181 |
| 2006/0195133 A1 | 8/2006 | Freeman .............. 606/181 |
| 2006/0196031 A1 | 9/2006 | Hoenes ................... 29/432 |
| 2006/0196795 A1 | 9/2006 | Windus-Smith ...... 206/438 |
| 2006/0200044 A1 | 9/2006 | Freeman .............. 600/583 |
| 2006/0200045 A1 | 9/2006 | Roe ...................... 600/583 |
| 2006/0200046 A1 | 9/2006 | Windus-Smith ...... 600/583 |
| 2006/0200181 A1 | 9/2006 | Fukuzawa ............ 606/181 |
| 2006/0200981 A1 | 9/2006 | Bhullar ................... 29/847 |
| 2006/0200982 A1 | 9/2006 | Bhullar ................... 29/847 |
| 2006/0201804 A1 | 9/2006 | Chambers ............ 204/400 |
| 2006/0204399 A1 | 9/2006 | Freeman ................ 422/58 |
| 2006/0205029 A1 | 9/2006 | Heller ..................... 435/25 |
| 2006/0205060 A1 | 9/2006 | Kim .................. 435/287.2 |
| 2006/0206135 A1 | 9/2006 | Uehata ................. 606/181 |
| 2006/0211127 A1 | 9/2006 | Iwaki ................... 436/169 |
| 2006/0211927 A1 | 9/2006 | Acosta ................. 600/316 |
| 2006/0211931 A1 | 9/2006 | Blank ................... 600/344 |
| 2006/0219551 A1 | 10/2006 | Edelbrock ........ 204/403.14 |
| 2006/0222566 A1 | 10/2006 | Brauker et al. ........ 422/68.1 |
| 2006/0222567 A1 | 10/2006 | Kloepfer .............. 422/68.1 |
| 2006/0224171 A1 | 10/2006 | Sakata .................. 606/181 |
| 2006/0224172 A1 | 10/2006 | LeVaughn ........... 606/181 |
| 2006/0229532 A1 | 10/2006 | Wong ................... 600/583 |
| 2006/0229533 A1 | 10/2006 | Hoenes ................. 600/584 |
| 2006/0229651 A1 | 10/2006 | Marshall .............. 606/181 |
| 2006/0231396 A1 | 10/2006 | Yamaoka ......... 204/403.14 |
| 2006/0231418 A1 | 10/2006 | Harding ................ 205/775 |
| 2006/0231421 A1 | 10/2006 | Diamond ........... 205/777.5 |
| 2006/0231423 A1 | 10/2006 | Harding ................ 205/792 |
| 2006/0231425 A1 | 10/2006 | Harding ................ 205/792 |
| 2006/0231442 A1 | 10/2006 | Windus-Smith ...... 206/438 |
| 2006/0232278 A1 | 10/2006 | Diamond .............. 324/444 |
| 2006/0232528 A1 | 10/2006 | Harding .................. 345/87 |
| 2006/0233666 A1 | 10/2006 | Vu ........................ 422/68.1 |
| 2006/0234263 A1 | 10/2006 | Light ......................... 435/6 |
| 2006/0234369 A1 | 10/2006 | Sih ....................... 435/287.1 |
| 2006/0235284 A1 | 10/2006 | Lee ...................... 600/345 |
| 2006/0235454 A1 | 10/2006 | LeVaughn ........... 606/181 |
| 2006/0241517 A1 | 10/2006 | Fowler ................. 600/583 |
| 2006/0241666 A1 | 10/2006 | Briggs .................. 606/181 |
| 2006/0241667 A1 | 10/2006 | Freeman .............. 606/181 |
| 2006/0241668 A1 | 10/2006 | Schraga ................ 606/181 |
| 2006/0241669 A1 | 10/2006 | Stout .................... 606/182 |
| 2006/0247154 A1 | 11/2006 | Palmieri .................. 514/8 |
| 2006/0247554 A1 | 11/2006 | Roe ...................... 600/583 |
| 2006/0247555 A1 | 11/2006 | Harttig ................. 600/584 |
| 2006/0247670 A1 | 11/2006 | LeVaughn ........... 606/181 |
| 2006/0247671 A1 | 11/2006 | LeVaughn ........... 606/182 |
| 2006/0254932 A1 | 11/2006 | Hodges ................. 205/775 |
| 2006/0259057 A1 | 11/2006 | Kim ...................... 606/181 |
| 2006/0259058 A1 | 11/2006 | Schiff ................... 606/181 |
| 2006/0259060 A1 | 11/2006 | Whitson ............... 606/182 |
| 2006/0264718 A1 | 11/2006 | Ruchti .................. 600/310 |
| 2006/0264996 A1 | 11/2006 | Levaughn ............ 606/181 |
| 2006/0264997 A1 | 11/2006 | Colonna ............... 606/181 |
| 2006/0266644 A1 | 11/2006 | Pugh .................... 204/400 |
| 2006/0266765 A1 | 11/2006 | Pugh ......................... 222/1 |
| 2006/0271083 A1 | 11/2006 | Boecker ............... 606/181 |
| 2006/0271084 A1 | 11/2006 | Schraga ................ 606/182 |
| 2006/0276724 A1 | 12/2006 | Freeman .............. 600/583 |
| 2006/0277048 A1 | 12/2006 | Kintzig ................. 704/275 |
| 2006/0278545 A1 | 12/2006 | Henning ............... 206/363 |
| 2006/0279431 A1 | 12/2006 | Bakarania ......... 340/870.02 |
| 2006/0281187 A1 | 12/2006 | Emery .................. 436/169 |
| 2006/0282109 A1 | 12/2006 | Jansen .................. 606/181 |
| 2006/0286620 A1 | 12/2006 | Werner ................... 435/14 |
| 2006/0287664 A1 | 12/2006 | Grage .................. 606/181 |
| 2006/0293577 A1 | 12/2006 | Morrison .............. 600/365 |
| 2007/0004989 A1 | 1/2007 | Dhillon ................. 600/583 |
| 2007/0004990 A1 | 1/2007 | Kistner ................. 600/583 |
| 2007/0007183 A1 | 1/2007 | Schulat ................. 209/573 |
| 2007/0009381 A1 | 1/2007 | Schulat ................... 422/58 |
| 2007/0010839 A1 | 1/2007 | Galloway ............. 606/167 |
| 2007/0010841 A1 | 1/2007 | Teo ...................... 606/181 |
| 2007/0015978 A1 | 1/2007 | Kanayama ............ 600/310 |
| 2007/0016079 A1 | 1/2007 | Freeman .............. 600/476 |
| 2007/0016103 A1 | 1/2007 | Calasso ................ 600/583 |
| 2007/0016104 A1 | 1/2007 | Jansen .................. 600/583 |
| 2007/0016239 A1 | 1/2007 | Sato ..................... 606/181 |
| 2007/0017805 A1 | 1/2007 | Hodges ................. 204/400 |
| 2007/0027370 A1 | 2/2007 | Brauker ................ 600/309 |
| 2007/0027427 A1 | 2/2007 | Trautman ................ 604/46 |
| 2007/0032812 A1 | 2/2007 | Loerwald ............. 606/181 |
| 2007/0032813 A1 | 2/2007 | Flynn ................... 606/181 |
| 2007/0038149 A1 | 2/2007 | Calasso ................ 600/583 |

| | | | |
|---|---|---|---|
| 2007/0038235 A1 | 2/2007 | Freeman | 606/181 |
| 2007/0043305 A1 | 2/2007 | Boecker | 600/583 |
| 2007/0043386 A1 | 2/2007 | Freeman | 606/181 |
| 2007/0049901 A1 | 3/2007 | Wu | 604/506 |
| 2007/0049959 A1 | 3/2007 | Feaster | 606/181 |
| 2007/0055174 A1 | 3/2007 | Freeman | 600/583 |
| 2007/0055297 A1 | 3/2007 | Fukuzawa | 606/181 |
| 2007/0055298 A1 | 3/2007 | Uehata | 606/181 |
| 2007/0060842 A1 | 3/2007 | Alvarez-Icaza | 600/583 |
| 2007/0060843 A1 | 3/2007 | Alvarez-Icaza | 600/583 |
| 2007/0060844 A1 | 3/2007 | Alvarez-Icaza | 600/583 |
| 2007/0060845 A1 | 3/2007 | Perez | 600/583 |
| 2007/0061393 A1 | 3/2007 | Moore | 205/777.5 |
| 2007/0062250 A1 | 3/2007 | Krulevitch | 73/1.16 |
| 2007/0062251 A1 | 3/2007 | Anex | 73/1.36 |
| 2007/0062315 A1 | 3/2007 | Hodges | 73/864.72 |
| 2007/0064516 A1 | 3/2007 | Briggs | 365/230.05 |
| 2007/0066939 A1 | 3/2007 | Krulevitch | 604/152 |
| 2007/0066940 A1 | 3/2007 | Karunaratne | 604/152 |
| 2007/0068807 A1 | 3/2007 | Feldman | 204/403.01 |
| 2007/0073188 A1 | 3/2007 | Freeman | 600/583 |
| 2007/0073189 A1 | 3/2007 | Freeman | 600/583 |
| 2007/0074977 A1 | 4/2007 | Guo | 205/792 |
| 2007/0078358 A1 | 4/2007 | Escutia | 600/573 |
| 2007/0078360 A1 | 4/2007 | Matsumoto | 600/583 |
| 2007/0078474 A1 | 4/2007 | Kim | 606/181 |
| 2007/0080093 A1 | 4/2007 | Boozer | 206/569 |
| 2007/0083130 A1 | 4/2007 | Thomson | 600/583 |
| 2007/0083131 A1 | 4/2007 | Escutia | 600/583 |
| 2007/0083222 A1 | 4/2007 | Schraga | 606/181 |
| 2007/0083335 A1 | 4/2007 | Moerman | 702/19 |
| 2007/0084749 A1 | 4/2007 | Demelo | 206/569 |
| 2007/0088377 A1 | 4/2007 | LeVaughn | 606/181 |
| 2007/0092923 A1 | 4/2007 | Chang | 435/14 |
| 2007/0093728 A1 | 4/2007 | Douglas | 600/583 |
| 2007/0093752 A1 | 4/2007 | Zhao | 604/131 |
| 2007/0093753 A1 | 4/2007 | Krulevitch | 604/131 |
| 2007/0093863 A1 | 4/2007 | Pugh | 606/181 |
| 2007/0093864 A1 | 4/2007 | Pugh | 606/181 |
| 2007/0095178 A1 | 5/2007 | Schraga | 83/13 |
| 2007/0100255 A1 | 5/2007 | Boecker | 600/583 |
| 2007/0100256 A1 | 5/2007 | Sansom | 600/583 |
| 2007/0100364 A1 | 5/2007 | Sansom | 606/181 |
| 2007/0102312 A1 | 5/2007 | Cha | 206/363 |
| 2007/0106178 A1 | 5/2007 | Roe | 600/583 |
| 2007/0108048 A1 | 5/2007 | Wang | 204/403.01 |
| 2007/0112281 A1 | 5/2007 | Olson | 600/583 |
| 2007/0112367 A1 | 5/2007 | Olson | 606/181 |
| 2007/0119710 A1 | 5/2007 | Goldberger | 204/403.01 |
| 2007/0123801 A1 | 5/2007 | Goldberger | 600/583 |
| 2007/0123802 A1 | 5/2007 | Freeman | 600/583 |
| 2007/0129618 A1 | 6/2007 | Goldberger | 600/345 |
| 2007/0129650 A1 | 6/2007 | Freeman | 606/181 |
| 2007/0131565 A1 | 6/2007 | Fujiwara | 205/777.5 |
| 2007/0135828 A1 | 6/2007 | Rutynowski | 606/181 |
| 2007/0142747 A1 | 6/2007 | Boecker | 600/583 |
| 2007/0142748 A1 | 6/2007 | Deshmukh | 600/583 |
| 2007/0142776 A9 | 6/2007 | Kovelman | 604/136 |
| 2007/0142854 A1 | 6/2007 | Schraga | 606/181 |
| 2007/0144235 A1 | 6/2007 | Werner | 73/1.82 |
| 2007/0149875 A1 | 6/2007 | Ouyang | 600/347 |
| 2007/0149897 A1 | 6/2007 | Ghesquiere | 600/583 |
| 2007/0161960 A1 | 7/2007 | Chen | 604/187 |
| 2007/0162064 A1 | 7/2007 | Starnes | 606/181 |
| 2007/0162065 A1 | 7/2007 | Li | 606/182 |
| 2007/0167869 A1 | 7/2007 | Roe | 600/583 |
| 2007/0167870 A1 | 7/2007 | Freeman | 600/583 |
| 2007/0167871 A1 | 7/2007 | Freeman | 600/583 |
| 2007/0167872 A1 | 7/2007 | Freeman | 600/583 |
| 2007/0167873 A1 | 7/2007 | Freeman | 600/583 |
| 2007/0167874 A1 | 7/2007 | Freeman | 600/583 |
| 2007/0167875 A1 | 7/2007 | Freeman | 600/583 |
| 2007/0173739 A1 | 7/2007 | Chan | 600/583 |
| 2007/0173740 A1 | 7/2007 | Chan | 600/583 |
| 2007/0173741 A1 | 7/2007 | Deshmukh | 600/583 |
| 2007/0173742 A1 | 7/2007 | Freeman | 600/583 |
| 2007/0173743 A1 | 7/2007 | Freeman | 600/583 |
| 2007/0173874 A1 | 7/2007 | Uschold | 606/181 |
| 2007/0173875 A1 | 7/2007 | Uschold | 606/181 |
| 2007/0173876 A1 | 7/2007 | Aylett | 606/181 |
| 2007/0176120 A1 | 8/2007 | Schwind | 250/492.1 |
| 2007/0179356 A1 | 8/2007 | Wessel | 600/300 |
| 2007/0179404 A1 | 8/2007 | Escutia | 600/583 |
| 2007/0179405 A1 | 8/2007 | Emery | 600/583 |
| 2007/0179406 A1 | 8/2007 | DeNuzzio | 600/583 |
| 2007/0182051 A1 | 8/2007 | Harttig | 264/138 |
| 2007/0185412 A1 | 8/2007 | Boecker | 600/583 |
| 2007/0185515 A1 | 8/2007 | Stout | 606/181 |
| 2007/0185516 A1 | 8/2007 | Schosnig | 606/181 |
| 2007/0191702 A1 | 8/2007 | Yodfat | 600/365 |
| 2007/0191737 A1 | 8/2007 | Freeman | 600/583 |
| 2007/0191738 A1 | 8/2007 | Raney | 600/583 |
| 2007/0191739 A1 | 8/2007 | Roe | 600/583 |
| 2007/0193019 A1 | 8/2007 | Feldman | 29/592.1 |
| 2007/0193882 A1 | 8/2007 | Dai | 204/403.02 |
| 2007/0196240 A1 | 8/2007 | Boozer | 422/102 |
| 2007/0196242 A1 | 8/2007 | Boozer | 422/102 |
| 2007/0203514 A1 | 8/2007 | Flaherty | 606/181 |
| 2007/0203903 A1 | 8/2007 | Attaran Rezaei | 707/5 |
| 2007/0205103 A1 | 9/2007 | Hodges | 204/403.01 |
| 2007/0207498 A1 | 9/2007 | Palmieri | 435/7.1 |
| 2007/0213601 A1 | 9/2007 | Freeman | 600/300 |
| 2007/0213637 A1 | 9/2007 | Boozer | 600/583 |
| 2007/0213682 A1 | 9/2007 | Haar | 604/500 |
| 2007/0213756 A1 | 9/2007 | Freeman | 606/181 |
| 2007/0218543 A1 | 9/2007 | Flaherty | 435/287.1 |
| 2007/0219346 A1 | 9/2007 | Trifiro | 530/308 |
| 2007/0219432 A1 | 9/2007 | Thompson | 600/300 |
| 2007/0219436 A1 | 9/2007 | Takase | 600/310 |
| 2007/0219462 A1 | 9/2007 | Briggs | 600/583 |
| 2007/0219463 A1 | 9/2007 | Briggs | 600/583 |
| 2007/0219572 A1 | 9/2007 | Deck | 606/181 |
| 2007/0219573 A1 | 9/2007 | Freeman | 606/183 |
| 2007/0219574 A1 | 9/2007 | Freeman | 606/185 |
| 2007/0225741 A1 | 9/2007 | Ikeda | 606/182 |
| 2007/0225742 A1 | 9/2007 | Abe | 606/182 |
| 2007/0227907 A1 | 10/2007 | Shah | 205/777.5 |
| 2007/0227911 A1 | 10/2007 | Wang | 205/792 |
| 2007/0227912 A1 | 10/2007 | Chatelier | 205/792 |
| 2007/0229085 A1 | 10/2007 | Kawai | 324/450 |
| 2007/0232872 A1 | 10/2007 | Prough | 600/316 |
| 2007/0232956 A1 | 10/2007 | Harman | 600/573 |
| 2007/0233013 A1 | 10/2007 | Schoenberg | 604/192 |
| 2007/0233166 A1 | 10/2007 | Stout | 606/181 |
| 2007/0233167 A1 | 10/2007 | Weiss | 606/182 |
| 2007/0233395 A1 | 10/2007 | Neel | 702/19 |
| 2007/0235329 A1 | 10/2007 | Harding | 204/403.01 |
| 2007/0235347 A1 | 10/2007 | Chatelier | 205/792 |
| 2007/0239068 A1 | 10/2007 | Rasch-Menges | 600/573 |
| 2007/0239188 A1 | 10/2007 | Boozer | 606/181 |
| 2007/0239189 A1 | 10/2007 | Freeman | 606/181 |
| 2007/0239190 A1 | 10/2007 | Alden | 606/181 |
| 2007/0240984 A1 | 10/2007 | Popovich | 204/403.01 |
| 2007/0240986 A1 | 10/2007 | Reymond | 204/412 |
| 2007/0244380 A1 | 10/2007 | Say | 600/347 |
| 2007/0244412 A1 | 10/2007 | Lav | 600/584 |
| 2007/0244498 A1 | 10/2007 | Steg | 606/181 |
| 2007/0244499 A1 | 10/2007 | Briggs | 606/182 |
| 2007/0249921 A1 | 10/2007 | Groll | 600/347 |
| 2007/0249962 A1 | 10/2007 | Alden | 600/583 |
| 2007/0249963 A1 | 10/2007 | Alden | 600/583 |
| 2007/0250099 A1 | 10/2007 | Flora | 606/181 |
| 2007/0251836 A1 | 11/2007 | Hsu | 205/792 |
| 2007/0254359 A1 | 11/2007 | Rezania | 435/325 |
| 2007/0255141 A1 | 11/2007 | Esenaliev | 600/475 |
| 2007/0255178 A1 | 11/2007 | Alvarez-Icaza | 600/583 |
| 2007/0255179 A1 | 11/2007 | Alvarez-Icaza | 600/583 |
| 2007/0255180 A1 | 11/2007 | Alvarez-Icaza | 600/583 |
| 2007/0255181 A1 | 11/2007 | Alvarez-Icaza | 600/583 |
| 2007/0255300 A1 | 11/2007 | Vanhiel | 606/181 |
| 2007/0255301 A1 | 11/2007 | Freeman | 606/181 |
| 2007/0255302 A1 | 11/2007 | Koeppel | 606/182 |
| 2007/0260271 A1 | 11/2007 | Freeman | 606/181 |
| 2007/0260272 A1 | 11/2007 | Weiss | 606/181 |
| 2007/0264721 A1 | 11/2007 | Buck | 436/150 |
| 2007/0265511 A1 | 11/2007 | Renouf | 600/319 |
| 2007/0265532 A1 | 11/2007 | Maynard | 600/477 |
| 2007/0265654 A1 | 11/2007 | Iio | 606/185 |

| Pub. No. | Date | Name | Class |
|---|---|---|---|
| 2007/0273901 A1 | 11/2007 | Baskeyfield | 358/1.9 |
| 2007/0273903 A1 | 11/2007 | Baskeyfield | 358/1.9 |
| 2007/0273904 A1 | 11/2007 | Robinson | 358/1.9 |
| 2007/0273928 A1 | 11/2007 | Robinson | 358/1.9 |
| 2007/0276197 A1 | 11/2007 | Harmon | 600/300 |
| 2007/0276211 A1 | 11/2007 | Mir | 600/345 |
| 2007/0276290 A1 | 11/2007 | Boecker | 600/583 |
| 2007/0276425 A1 | 11/2007 | Kim | 606/186 |
| 2007/0276621 A1 | 11/2007 | Davies | 702/104 |
| 2007/0278097 A1 | 12/2007 | Bhullar | 204/403.01 |
| 2007/0282186 A1 | 12/2007 | Gilmore | 600/365 |
| 2007/0282362 A1 | 12/2007 | Berg | 606/181 |
| 2007/0288047 A1 | 12/2007 | Thoes | 606/182 |
| 2007/0293743 A1 | 12/2007 | Monfre | 600/316 |
| 2007/0293744 A1 | 12/2007 | Monfre | 600/316 |
| 2007/0293790 A1 | 12/2007 | Bainczyk | 600/583 |
| 2007/0293882 A1 | 12/2007 | Harttig | 606/181 |
| 2007/0293883 A1 | 12/2007 | Horie | 606/181 |
| 2007/0295616 A1 | 12/2007 | Harding | 205/777.5 |
| 2008/0004651 A1 | 1/2008 | Nicholls | 606/181 |
| 2008/0007141 A1 | 1/2008 | Deck | 310/328 |
| 2008/0009767 A1 | 1/2008 | Effenhauser | 600/583 |
| 2008/0009768 A1 | 1/2008 | Sohrab | 600/583 |
| 2008/0009892 A1 | 1/2008 | Freeman | 606/181 |
| 2008/0009893 A1 | 1/2008 | LeVaughn | 606/181 |
| 2008/0015425 A1 | 1/2008 | Douglas | 600/347 |
| 2008/0015623 A1 | 1/2008 | Deck | 606/181 |
| 2008/0017522 A1 | 1/2008 | Heller | 205/777.5 |
| 2008/0019870 A1 | 1/2008 | Newman | 422/68.1 |
| 2008/0021291 A1 | 1/2008 | Zocchi | 600/300 |
| 2008/0021293 A1 | 1/2008 | Schurman | 600/316 |
| 2008/0021295 A1 | 1/2008 | Wang | 600/347 |
| 2008/0021296 A1 | 1/2008 | Creaven | 600/365 |
| 2008/0021346 A1 | 1/2008 | Haar | 600/583 |
| 2008/0021490 A1 | 1/2008 | Briggs | 606/181 |
| 2008/0021491 A1 | 1/2008 | Freeman | 606/181 |
| 2008/0021492 A1 | 1/2008 | Freeman | 606/181 |
| 2008/0021493 A1 | 1/2008 | Levaughn | 606/181 |
| 2008/0021494 A1 | 1/2008 | Schmelzeisen-Redeker | 606/181 |
| 2008/0027385 A1 | 1/2008 | Freeman | 604/117 |
| 2008/0031778 A1 | 2/2008 | Kramer | 422/68.1 |
| 2008/0033268 A1 | 2/2008 | Stafford | 600/345 |
| 2008/0033318 A1 | 2/2008 | Mace | 600/583 |
| 2008/0033319 A1 | 2/2008 | Kloepfer | 600/583 |
| 2008/0033468 A1 | 2/2008 | Lathrop | 606/181 |
| 2008/0033469 A1 | 2/2008 | Winheim | 606/181 |
| 2008/0034834 A1 | 2/2008 | Schell | 73/1.02 |
| 2008/0034835 A1 | 2/2008 | Schell | 73/1.02 |
| 2008/0039885 A1 | 2/2008 | Purcell | 606/182 |
| 2008/0039886 A1 | 2/2008 | Shi | 606/182 |
| 2008/0039887 A1 | 2/2008 | Conway | 606/182 |
| 2008/0040919 A1 | 2/2008 | Griss | 29/777 |
| 2008/0042594 A1 | 2/2008 | Lopez et al. | 606/183 |
| 2008/0045825 A1 | 2/2008 | Melker | 600/365 |
| 2008/0045992 A1 | 2/2008 | Schraga | 606/182 |
| 2008/0047764 A1 | 2/2008 | Lee | |
| 2008/0053201 A1 | 3/2008 | Roesicke | 73/61.41 |
| 2008/0057484 A1 | 3/2008 | Miyata | 434/739 |
| 2008/0058624 A1 | 3/2008 | Smart | 600/345 |
| 2008/0058626 A1 | 3/2008 | Miyata | 600/365 |
| 2008/0058631 A1 | 3/2008 | Draudt | 600/385 |
| 2008/0058847 A1 | 3/2008 | Abe | 606/181 |
| 2008/0058848 A1 | 3/2008 | Griffin | 606/182 |
| 2008/0058849 A1 | 3/2008 | Conway | 606/183 |
| 2008/0060424 A1 | 3/2008 | Babic | 73/61.41 |
| 2008/0064986 A1 | 3/2008 | Kraemer | 600/583 |
| 2008/0064987 A1 | 3/2008 | Escutia | 600/583 |
| 2008/0065130 A1 | 3/2008 | Patel | 606/181 |
| 2008/0065131 A1 | 3/2008 | List | 606/181 |
| 2008/0065132 A1 | 3/2008 | Trissel | 606/182 |
| 2008/0065133 A1 | 3/2008 | Kennedy | 606/182 |
| 2008/0065134 A1 | 3/2008 | Conway | 606/182 |
| 2008/0073224 A1 | 3/2008 | Diamond | 205/775 |
| 2008/0077048 A1 | 3/2008 | Escutia | 600/583 |
| 2008/0077167 A1 | 3/2008 | Flynn | 606/172 |
| 2008/0077168 A1 | 3/2008 | Nicholls | 606/182 |
| 2008/0081969 A1 | 4/2008 | Feldman | 600/322 |
| 2008/0081976 A1 | 4/2008 | Hodges | 600/345 |
| 2008/0082023 A1 | 4/2008 | Deck | 600/583 |
| 2008/0082116 A1 | 4/2008 | Lathrop | 606/181 |
| 2008/0082117 A1 | 4/2008 | Ruf | 606/182 |
| 2008/0086042 A1 | 4/2008 | Brister | 600/347 |
| 2008/0086044 A1 | 4/2008 | Brister | 600/365 |
| 2008/0086273 A1 | 4/2008 | Schults | 702/19 |
| 2008/0093227 A1 | 4/2008 | Diamond | 205/775 |
| 2008/0093228 A1 | 4/2008 | Diamond | 205/782 |
| 2008/0093230 A1 | 4/2008 | Diamond | 205/792 |
| 2008/0094804 A1 | 4/2008 | Reynolds | 361/727 |
| 2008/0097171 A1 | 4/2008 | Smart | 600/309 |
| 2008/0097241 A1 | 4/2008 | Maltezos | 600/576 |
| 2008/0097503 A1 | 4/2008 | Creaven | 606/182 |
| 2008/0098802 A1 | 5/2008 | Burke | 73/61.61 |
| 2008/0103396 A1 | 5/2008 | Johnson | 600/477 |
| 2008/0103415 A1 | 5/2008 | Roe | 600/583 |
| 2008/0103517 A1 | 5/2008 | Takemoto | 606/182 |
| 2008/0105024 A1 | 5/2008 | Creaven | 73/1.02 |
| 2008/0105568 A1 | 5/2008 | Wu | 205/780.5 |
| 2008/0108130 A1 | 5/2008 | Nakaminami | 435/287.1 |
| 2008/0108942 A1 | 5/2008 | Brister | 604/118 |
| 2008/0109024 A1 | 5/2008 | Berkovitch | 606/181 |
| 2008/0109025 A1 | 5/2008 | Yang | 606/182 |
| 2008/0109259 A1 | 5/2008 | Thompson | 705/3 |
| 2008/0114227 A1 | 5/2008 | Haar | 600/347 |
| 2008/0114228 A1 | 5/2008 | McCluskey | 600/365 |
| 2008/0118400 A1 | 5/2008 | Neel | 422/68.1 |
| 2008/0119703 A1 | 5/2008 | Brister | 600/347 |
| 2008/0119704 A1 | 5/2008 | Brister | 600/347 |
| 2008/0119706 A1 | 5/2008 | Brister | 600/365 |
| 2008/0119761 A1 | 5/2008 | Boecker | 600/583 |
| 2008/0119883 A1 | 5/2008 | Conway | 606/181 |
| 2008/0119884 A1 | 5/2008 | Flora | 606/182 |
| 2008/0121533 A1 | 5/2008 | Hodges | 205/775 |
| 2008/0125800 A1 | 5/2008 | List | 606/181 |
| 2008/0125801 A1 | 5/2008 | List | 606/181 |
| 2008/0134806 A1 | 6/2008 | Capriccio | 73/863.21 |
| 2008/0134810 A1 | 6/2008 | Neel | 73/866 |
| 2008/0135559 A1 | 6/2008 | Byrd | 220/506 |
| 2008/0140105 A1 | 6/2008 | Zhong | 606/182 |
| 2008/0144022 A1 | 6/2008 | Schulat | 356/213 |
| 2008/0146899 A1 | 6/2008 | Ruchti | 600/316 |
| 2008/0146966 A1 | 6/2008 | LeVaughn | 600/583 |
| 2008/0147108 A1 | 6/2008 | Kennedy | 606/182 |
| 2008/0149268 A1 | 6/2008 | Zhao | 156/299 |
| 2008/0149599 A1 | 6/2008 | Bohm | 216/94 |
| 2008/0152507 A1 | 6/2008 | Bohm | 417/44.1 |
| 2008/0154187 A1 | 6/2008 | Krulevitch | 604/48 |
| 2008/0154513 A1 | 6/2008 | Kovatchev | 702/19 |
| 2008/0159913 A1 | 7/2008 | Jung | 422/57 |
| 2008/0161664 A1 | 7/2008 | Mastrototaro | 600/347 |
| 2008/0161724 A1 | 7/2008 | Roe | 600/583 |
| 2008/0161725 A1 | 7/2008 | Wong | 600/583 |
| 2008/0166269 A1 | 7/2008 | Jansen | 422/63 |
| 2008/0167578 A1 | 7/2008 | Bryer | 600/583 |
| 2008/0167673 A1 | 7/2008 | Zhong | 606/181 |
| 2008/0188771 A1 | 8/2008 | Boecker | 600/583 |
| 2008/0194987 A1 | 8/2008 | Boecker | 600/583 |
| 2008/0194989 A1 | 8/2008 | Briggs | 600/583 |
| 2008/0208026 A1 | 8/2008 | Noujaim | 600/365 |
| 2008/0208079 A1 | 8/2008 | Hein | 600/583 |
| 2008/0210574 A1 | 9/2008 | Boecker | 205/777.5 |
| 2008/0214909 A1 | 9/2008 | Fuerst | 600/309 |
| 2008/0214917 A1 | 9/2008 | Boecker | 600/347 |
| 2008/0214919 A1 | 9/2008 | Harmon | 600/365 |
| 2008/0214956 A1 | 9/2008 | Briggs | 600/575 |
| 2008/0228212 A1 | 9/2008 | List | 606/182 |
| 2008/0249435 A1 | 10/2008 | Haar | 600/583 |
| 2008/0249554 A1 | 10/2008 | Freeman | 606/181 |
| 2008/0255598 A1 | 10/2008 | LeVaughn et al. | 606/183 |
| 2008/0262387 A1 | 10/2008 | List | 600/583 |
| 2008/0262388 A1 | 10/2008 | List | 600/583 |
| 2008/0267822 A1 | 10/2008 | List | 422/68.1 |
| 2008/0269723 A1 | 10/2008 | Mastrototaro | 604/890.1 |
| 2008/0269791 A1 | 10/2008 | Hoenes | 606/181 |
| 2008/0275365 A1 | 11/2008 | Guthrie | 600/584 |
| 2008/0275384 A1 | 11/2008 | Mastrototaro | 604/66 |
| 2008/0277291 A1 | 11/2008 | Heller | 205/777.5 |
| 2008/0277292 A1 | 11/2008 | Heller | 205/777.5 |
| 2008/0277293 A1 | 11/2008 | Heller | 205/777.5 |

| | | | | |
|---|---|---|---|---|
| 2008/0277294 A1 | 11/2008 | Heller ......................... 205/777.5 | EP | 0317847 A1 | 5/1989 |
| 2008/0286149 A1 | 11/2008 | Roe ............................... 422/58 | EP | 0320109 | 6/1989 |
| 2008/0294068 A1 | 11/2008 | Briggs ........................... 600/583 | EP | 0364208 A1 | 4/1990 |
| 2008/0300614 A1 | 12/2008 | Freeman ........................ 606/181 | EP | 0170375 | 5/1990 |
| 2008/0318193 A1 | 12/2008 | Alvarez-Icaza ............... 434/262 | EP | 0136362 | 12/1990 |
| 2008/0319284 A1 | 12/2008 | Alvarez-Icaza ............... 600/309 | EP | 0449525 | 10/1991 |
| 2008/0319291 A1 | 12/2008 | Freeman ........................ 600/347 | EP | 0453283 | 10/1991 |
| 2009/0005664 A1 | 1/2009 | Freeman ........................ 600/347 | EP | 0263948 | 2/1992 |
| 2009/0020438 A1 | 1/2009 | Hodges ......................... 205/782 | EP | 0449147 A2 | 8/1992 |
| 2009/0024009 A1 | 1/2009 | Freeman ........................ 600/309 | EP | 0530994 | 3/1993 |
| 2009/0024059 A1 | 1/2009 | Hoerauf ........................ 600/583 | EP | 0374355 | 6/1993 |
| 2009/0026075 A1 | 1/2009 | Harding .................... 204/403.14 | EP | 0351891 | 9/1993 |
| 2009/0026091 A1 | 1/2009 | Harding .................... 205/777.5 | EP | 0593096 | 4/1994 |
| 2009/0027040 A1 | 1/2009 | Kermani ....................... 324/123 | EP | 0630609 A2 | 12/1994 |
| 2009/0029479 A1 | 1/2009 | Docherty ...................... 436/149 | EP | 0415388 | 5/1995 |
| 2009/0043177 A1 | 2/2009 | Milledge ....................... 600/309 | EP | 0654659 | 5/1995 |
| 2009/0043183 A1 | 2/2009 | Kermani ....................... 600/365 | EP | 0505494 | 7/1995 |
| 2009/0048536 A1 | 2/2009 | Freeman ........................ 600/583 | EP | 0662367 A1 | 7/1995 |
| 2009/0054813 A1 | 2/2009 | Freeman ........................ 600/584 | EP | 0359831 | 8/1995 |
| 2009/0057146 A1 | 3/2009 | Teodorczyk ............. 204/403.01 | EP | 0471986 | 10/1995 |
| 2009/0069716 A1 | 3/2009 | Freeman ........................ 600/583 | EP | 0368474 | 12/1995 |
| 2009/0084687 A1 | 4/2009 | Chatelier ....................... 205/792 | EP | 0461601 | 12/1995 |
| 2009/0105572 A1 | 4/2009 | Malecha ........................ 600/365 | EP | 0429076 | 1/1996 |
| 2009/0105573 A1 | 4/2009 | Malecha ........................ 600/365 | EP | 0552223 | 7/1996 |
| 2009/0112123 A1 | 4/2009 | Freeman ........................ 600/583 | EP | 0735363 | 10/1996 |
| 2009/0112155 A1 | 4/2009 | Zhao ............................... 604/67 | EP | 0505504 | 3/1997 |
| 2009/0112180 A1 | 4/2009 | Krulevitch .................... 604/506 | EP | 0777123 | 6/1997 |
| 2009/0112185 A1 | 4/2009 | Krulevitch .................... 604/523 | EP | 0406304 | 8/1997 |
| 2009/0124932 A1 | 5/2009 | Freeman ........................ 606/181 | EP | 0537761 | 8/1997 |
| 2009/0131829 A1 | 5/2009 | Freeman ........................ 600/583 | EP | 0795601 | 9/1997 |
| 2009/0131830 A1 | 5/2009 | Freeman ........................ 600/583 | EP | 0562370 | 11/1997 |
| 2009/0131964 A1 | 5/2009 | Freeman ........................ 606/181 | EP | 0415393 | 12/1997 |
| 2009/0131965 A1 | 5/2009 | Freeman ........................ 606/181 | EP | 0823239 | 2/1998 |
| 2009/0137930 A1 | 5/2009 | Freeman ........................ 600/583 | EP | 0560336 | 5/1998 |
| 2009/0138032 A1 | 5/2009 | Freeman ........................ 606/181 | EP | 0878 708 | 11/1998 |
| 2009/0139300 A1 | 6/2009 | Pugh ............................... 73/1.36 | EP | 0505475 | 3/1999 |
| 2009/0184004 A1 | 7/2009 | Chatelier .................... 205/777.5 | EP | 0898936 A2 | 3/1999 |
| 2009/0187351 A1 | 7/2009 | Orr ................................. 702/19 | EP | 0901018 | 3/1999 |
| 2009/0192410 A1 | 7/2009 | Freeman ........................ 600/583 | EP | 0470649 | 6/1999 |
| 2009/0192411 A1 | 7/2009 | Freeman ........................ 600/583 | EP | 0951939 A2 | 10/1999 |
| 2009/0196580 A1 | 8/2009 | Freeman ........................ 386/124 | EP | 0847447 | 11/1999 |
| 2009/0204025 A1 | 8/2009 | Marsot ........................... 600/573 | EP | 0964059 | 12/1999 |
| 2009/0216100 A1 | 8/2009 | Ebner ............................ 600/347 | EP | 0964060 | 12/1999 |
| 2009/0237262 A1 | 9/2009 | Smith ............................ 340/634 | EP | 0969097 | 1/2000 |
| 2009/0240127 A1 | 9/2009 | Ray ............................... 600/365 | EP | 0985376 A1 | 3/2000 |
| 2009/0247838 A1 | 10/2009 | Cummings ................... 600/309 | EP | 1021950 | 7/2000 |
| 2009/0247982 A1 | 10/2009 | Krulevitch et al. ........... 604/500 | EP | 0894869 | 2/2001 |
| 2009/0259146 A1 | 10/2009 | Freeman ........................ 600/583 | EP | 1074832 | 2/2001 |
| 2009/0280551 A1 | 11/2009 | Cardosi ......................... 435/190 | EP | 1093854 | 4/2001 |
| 2009/0281457 A1 | 11/2009 | Faulkner ....................... 600/583 | EP | 1101443 A2 | 5/2001 |
| 2009/0281458 A1 | 11/2009 | Faulkner ....................... 600/583 | EP | 1114995 | 7/2001 |
| 2009/0281459 A1 | 11/2009 | Faulkner ....................... 600/583 | EP | 0736607 | 8/2001 |
| 2009/0301899 A1 | 12/2009 | Hodges ..................... 205/777.5 | EP | 0874984 | 11/2001 |
| 2009/0302872 A1 | 12/2009 | Haggett ......................... 324/715 | EP | 1157660 | 11/2001 |
| 2009/0302873 A1 | 12/2009 | Haggett ......................... 324/724 | EP | 0730037 | 12/2001 |
| 2009/0322630 A1 | 12/2009 | Friman .......................... 343/720 | EP | 0636879 | 1/2002 |
| 2009/0325307 A1 | 12/2009 | Haggett ......................... 436/150 | EP | 01174083 | 1/2002 |
| 2010/0016700 A1 | 1/2010 | Sieh ............................... 600/365 | EP | 0851224 | 3/2002 |
| 2010/0018878 A1 | 1/2010 | Davies .......................... 205/782 | EP | 0759553 | 5/2002 |
| 2010/0030110 A1 | 2/2010 | Choi ............................. 600/583 | EP | 0856586 | 5/2002 |
| 2010/0041084 A1 | 2/2010 | Stephens ........................ 435/14 | EP | 0817809 | 7/2002 |
| | | | EP | 0872728 | 7/2002 |
| FOREIGN PATENT DOCUMENTS | | | EP | 0795748 | 8/2002 |
| | | | EP | 0685737 | 9/2002 |
| DE | 4420232 | 12/1995 | EP | 0958495 | 11/2002 |
| DE | 29800611 U | 7/1998 | EP | 0937249 | 12/2002 |
| DE | 29824204 | 10/2000 | EP | 1337182 | 8/2003 |
| DE | 10053974 | 12/2000 | EP | 0880692 | 1/2004 |
| DE | 10032042 | 1/2002 | EP | 01374770 | 1/2004 |
| DE | 10057832 | 2/2002 | EP | 1404232 | 4/2004 |
| DE | 10142232 | 3/2003 | EP | 1404233 | 4/2004 |
| DE | 10208575 C1 | 8/2003 | EP | 1246688 | 5/2004 |
| DE | 10245721 | 12/2003 | EP | 1502614 | 2/2005 |
| DE | 10361560 A1 | 7/2005 | EP | 1643908 | 4/2006 |
| EP | 0112498 A2 | 7/1984 | EP | 1790288 | 5/2007 |
| EP | 137975 A2 | 4/1985 | EP | 1921992 | 5/2008 |
| EP | 0160768 | 11/1985 | EP | 2039294 | 3/2009 |
| EP | 0199484 A2 | 10/1986 | FR | 2555432 | 5/1985 |
| EP | 0254246 | 1/1988 | FR | 2622457 | 11/1987 |
| EP | 0289 269 | 11/1988 | | | |

| | | | | | | |
|---|---|---|---|---|---|---|
| GB | 1558111 | 12/1979 | | WO | WO 01/15807 A1 | 3/2001 |
| GB | 2168815 | 6/1986 | | WO | WO 01/16578 A1 | 3/2001 |
| GB | 2331936 | 6/1999 | | WO | WO 01/75433 | 3/2001 |
| GB | 2335860 | 10/1999 | | WO | WO 01/23885 | 4/2001 |
| GB | 2335990 | 10/1999 | | WO | WO 01/25775 | 4/2001 |
| JP | HEI 4 1992 194660 | 7/1992 | | WO | WO 01/26813 | 4/2001 |
| JP | 1996010208 | 12/1992 | | WO | WO 01/33216 | 5/2001 |
| JP | 9-276235 | 10/1997 | | WO | WO 01/34029 | 5/2001 |
| JP | 1014906 | 1/1998 | | WO | WO 01/36955 | 5/2001 |
| JP | 2000-116768 | 4/2000 | | WO | WO 01/37174 | 5/2001 |
| WO | WO 80/01389 | 7/1980 | | WO | WO 01/45014 A1 | 6/2001 |
| WO | WO 85/04089 | 9/1985 | | WO | WO 01/40788 | 7/2001 |
| WO | WO 86/07632 | 12/1985 | | WO | WO 01/57510 | 8/2001 |
| WO | WO 91/09139 | 6/1991 | | WO | WO 01/63271 | 8/2001 |
| WO | WO92/07263 | 4/1992 | | WO | WO 01/64105 | 9/2001 |
| WO | WO92/07468 | 5/1992 | | WO | WO 01/66010 | 9/2001 |
| WO | WO93/00044 | 1/1993 | | WO | WO 01/69505 | 9/2001 |
| WO | WO 93/02720 | 2/1993 | | WO | WO 01/72220 A1 | 10/2001 |
| WO | WO 93/06979 | 4/1993 | | WO | WO 01/72225 | 10/2001 |
| WO | WO 93/12726 | 7/1993 | | WO | WO 01/73124 | 10/2001 |
| WO | WO 93/25898 | 12/1993 | | WO | WO 01/73395 | 10/2001 |
| WO | WO 94/27140 | 11/1994 | | WO | WO 02/00101 | 1/2002 |
| WO | WO 94/29703 | 12/1994 | | WO | WO 02/02796 | 1/2002 |
| WO | WO 94/29704 | 12/1994 | | WO | WO 02/08750 | 1/2002 |
| WO | WO 94/29731 | 12/1994 | | WO | WO 02/08753 | 1/2002 |
| WO | WO 95/00662 | 1/1995 | | WO | WO 02/08950 | 1/2002 |
| WO | WO 95/06240 | 3/1995 | | WO | WO 02/18940 | 3/2002 |
| WO | WO 95/10223 | 4/1995 | | WO | WO 02/21317 | 3/2002 |
| WO | WO 95/22597 | 8/1995 | | WO | WO 02/25551 | 3/2002 |
| WO | WO 96/30431 | 10/1996 | | WO | WO 02/32559 | 4/2002 |
| WO | WO96/37148 | 11/1996 | | WO | WO 02/41227 | 5/2002 |
| WO | WO 97/02359 | 1/1997 | | WO | WO 02/41779 | 5/2002 |
| WO | WO 97/02487 | 1/1997 | | WO | WO 02/44948 | 6/2002 |
| WO | WO 97/18464 | 5/1997 | | WO | WO 02/49507 | 6/2002 |
| WO | WO97/28741 | 8/1997 | | WO | WO 02/056769 | 7/2002 |
| WO | WO 97/30344 | 8/1997 | | WO | WO 02/059734 | 8/2002 |
| WO | WO 97/42882 | 11/1997 | | WO | WO 02/069791 | 9/2002 |
| WO | WO 97/45720 | 12/1997 | | WO | WO 02/077638 | 10/2002 |
| WO | WO 98/03431 | 1/1998 | | WO | WO 02/100251 | 12/2002 |
| WO | WO 98/19159 | 5/1998 | | WO | WO 02/100252 | 12/2002 |
| WO | WO 98/20332 | 5/1998 | | WO | WO 02/100253 | 12/2002 |
| WO | WO 98/20348 | 5/1998 | | WO | WO 02/100254 | 12/2002 |
| WO | WO 98/24366 | 6/1998 | | WO | WO 02/100460 | 12/2002 |
| WO | WO 98 24373 | 6/1998 | | WO | WO 02/100461 | 12/2002 |
| WO | WO 98/35225 | 8/1998 | | WO | WO 02/101343 | 12/2002 |
| WO | WO 99/03584 | 1/1999 | | WO | WO 02/101359 | 12/2002 |
| WO | WO 99/05966 | 2/1999 | | WO | WO 03/000321 | 1/2003 |
| WO | WO 99/07431 | 2/1999 | | WO | WO 03/023389 | 3/2003 |
| WO | WO 99/62576 | 3/1999 | | WO | WO 03/042691 | 5/2003 |
| WO | WO 99/17854 | 4/1999 | | WO | WO 03039369 A | 5/2003 |
| WO | WO 99/18532 | 4/1999 | | WO | WO 03/045557 | 6/2003 |
| WO | WO 99/19507 | 4/1999 | | WO | WO 03/046542 | 6/2003 |
| WO | WO 99/19717 | 4/1999 | | WO | WO 03/049609 | 6/2003 |
| WO | WO 99/27483 | 6/1999 | | WO | WO 03/050534 | 6/2003 |
| WO | WO 99/27852 | 6/1999 | | WO | WO 03/066128 | 8/2003 |
| WO | WO 99/13100 | 12/1999 | | WO | WO 03/070099 | 8/2003 |
| WO | WO 99/64580 | 12/1999 | | WO | WO 03/071940 | 9/2003 |
| WO | WO 00/06024 | 2/2000 | | WO | WO 03/082091 | 10/2003 |
| WO | WO 00/09184 | 2/2000 | | WO | WO 03/088851 A1 | 10/2003 |
| WO | WO 00/11578 | 3/2000 | | WO | WO 03/094752 | 11/2003 |
| WO | WO 00/15103 | 3/2000 | | WO | WO 03/101297 | 12/2003 |
| WO | WO 00/17799 | 3/2000 | | WO | WO 2004/008130 | 1/2004 |
| WO | WO 00/17800 | 3/2000 | | WO | WO 2004/022133 | 3/2004 |
| WO | WO 00/18293 | 4/2000 | | WO | WO 2004/026130 | 4/2004 |
| WO | WO 00/19346 | 4/2000 | | WO | WO 2004/040285 A2 | 5/2004 |
| WO | WO 00/30186 | 5/2000 | | WO | WO 2004/040287 A1 | 5/2004 |
| WO | WO 00/32097 | 6/2000 | | WO | WO 2004/040948 | 5/2004 |
| WO | WO 00/32098 | 6/2000 | | WO | WO 2004/041082 | 5/2004 |
| WO | WO 00/33236 | 6/2000 | | WO | WO 2004/054455 | 7/2004 |
| WO | WO 00/39914 | 7/2000 | | WO | WO 2004/060174 | 7/2004 |
| WO | WO 00/42422 | 7/2000 | | WO | WO 2004/060446 | 7/2004 |
| WO | WO 00/44084 | 7/2000 | | WO | WO 2004/091693 | 10/2004 |
| WO | WO 00/50771 | 8/2000 | | WO | WO 2004/098405 | 11/2004 |
| WO | WO 00/60340 | 10/2000 | | WO | WO 2004/003147 | 12/2004 |
| WO | WO 00/64022 | 10/2000 | | WO | WO 2004/107964 | 12/2004 |
| WO | WO 00/67245 | 11/2000 | | WO | WO 2004/107975 | 12/2004 |
| WO | WO 00/67268 | 11/2000 | | WO | WO 2004/112602 | 12/2004 |
| WO | WO 00/72452 | 11/2000 | | WO | WO 2005/001418 | 1/2005 |
| WO | WO 01/00090 | 1/2001 | | WO | WO 2005/006939 | 1/2005 |

| | | |
|---|---|---|
| WO | WO 2005/013824 | 2/2005 |
| WO | WO 2005/016125 | 2/2005 |
| WO | WO 2006/015615 | 2/2005 |
| WO | WO 2005/018425 | 3/2005 |
| WO | WO 2005/018430 | 3/2005 |
| WO | WO 2005/018454 | 3/2005 |
| WO | WO 2005/018709 | 3/2005 |
| WO | WO 2005/018710 | 3/2005 |
| WO | WO 2005/018711 | 3/2005 |
| WO | WO 2005/022143 | 3/2005 |
| WO | WO 2005/023088 | 3/2005 |
| WO | WO 2005/033659 | 4/2005 |
| WO | WO 2005/034720 | 4/2005 |
| WO | WO 2005/034721 | 4/2005 |
| WO | WO 2005/034741 | 4/2005 |
| WO | WO 2005/034778 | 4/2005 |
| WO | WO 2005/035017 | 4/2005 |
| WO | WO 2005/035018 | 4/2005 |
| WO | WO 2005/037095 | 4/2005 |
| WO | WO 2005/046477 | 5/2005 |
| WO | WO 2005/065399 | 7/2005 |
| WO | WO 2005/065414 | 7/2005 |
| WO | WO 2005/065415 | 7/2005 |
| WO | WO 2005/072604 | 8/2005 |
| WO | WO 2005/084557 | 9/2005 |
| WO | WO 2005/104948 | 11/2005 |
| WO | WO 2005/116622 | 12/2005 |
| WO | WO 2005/119234 | 12/2005 |
| WO | WO 2005/121759 | 12/2005 |
| WO | WO 2006/001973 | 1/2006 |
| WO | WO 2006005545 A2 | 1/2006 |
| WO | WO 2006/011062 | 2/2006 |
| WO | WO 2006/013045 | 2/2006 |
| WO | WO 2006/027702 A2 | 3/2006 |
| WO | WO 2006/032391 | 3/2006 |
| WO | WO 2006/072004 | 7/2006 |
| WO | WO 2007/025635 | 3/2007 |
| WO | WO 2007/054335 | 5/2007 |
| WO | WO 2007/088905 A1 | 8/2007 |
| WO | WO 2007/119900 | 10/2007 |

OTHER PUBLICATIONS

Wolfbeis et al. (Sol-gel based glucose biosensors employing optical oxygen transducers, and a method for compensating for variable oxygen background, Biosensors & Bioelectronics 15 (2000) pp. 69-76).

METHOD OF MANUFACTURING A FLUID SAMPLING DEVICE WITH IMPROVED ANALYTE DETECTING MEMBER CONFIGURATION

CROSS-REFERENCE TO RELATED APPLICATIONS

The present application is a divisional application of U.S. application Ser. No. 11/028,952 filed Jan. 3, 2005, now U.S. Pat. No. 7,822,454, and claims the benefit of priority to U.S. Provisional Application Ser. No. 60/533,997 filed Dec. 31, 2003. The present application also claims the benefit of priority to U.S. Provisional Application Ser. No. 60/533,969 filed Dec. 31, 2003. These applications are incorporated herein by reference for all purposes.

BACKGROUND OF THE INVENTION

1. Field of the Invention

The invention relates to the collection of body fluid and transporting it to detecting members for determining certain aspects such as blood chemistry.

2. Description of Related Art

Treatment of diabetes requires frequent monitoring of levels of blood glucose. This is traditionally done in a series of steps involving the preparation of a lancing device, preparation of a glucose meter, lancing a finger, transporting the resulting blood drop to the meter, and finally obtaining a blood glucose reading.

Lancing devices are known in the medical health-care products industry for piercing the skin to produce blood for analysis. Biochemical analysis of blood samples is a diagnostic tool for determining clinical information. Many point-of-care tests are performed using capillary whole blood, the most common being monitoring diabetic blood glucose level. Other uses for this method include the analysis of oxygen and coagulation based on Prothrombin time measurement. Typically, a drop of blood for this type of analysis is obtained by making a small incision in the fingertip, creating a small wound, which generates a small blood droplet on the surface of the skin.

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. Typically, the device is pre-cocked or the user cocks the device. The device is held against the skin and mechanically triggers the ballistic launch of the lancet. The forward movement and depth of skin penetration of the lancet is determined by a mechanical stop and/or dampening, as well as a spring or cam to retract the lancet. Spontaneous blood droplet generation is dependent on reaching the blood capillaries and venuoles, which yield the blood sample.

As lancing devices have become more advanced, so have the device used to measure the glucose levels in the blood samples. These analyte measurement devices now operate using increasing lower volumes of blood sample. Some of these analyte sensors are designed for use with lancing devices that create smaller wounds, which is beneficial in that there is less pain and tissue damage, but also provide less blood to work with. As the required amount of blood decreases, it becomes increasing important to guide the ever shrinking volumes of blood towards the sensor in an efficient manner that does not waste the small volumes of blood.

SUMMARY OF THE INVENTION

The present invention provides solutions for at least some of the drawbacks discussed above. By combining analytical chemistry with a lancing device, the present invention allows the elimination of most of the steps used in known devices. Multiple individual analytical sets are combined in a single disposable module that indexes through a single user action, eliminating all of the setup and disposal steps currently required. At least some of these and other objectives described herein will be met by embodiments of the present invention.

The present invention provides solutions for at least some of the drawbacks discussed above. The present invention seeks to improve the amount of feedback to the user. The present invention desires to show more the internal workings of the device. At least some of these and other objectives described herein will be met by embodiments of the present invention.

In one embodiment, the present invention provides a directly observable user feedback on whether the sample has been captured. The housing may include a transparent window where the user can see if the their blood sample was successfully obtained by the tissue penetrating device. This addresses the human factors issue that will arise with more complex devices.

In another embodiment, a body fluid sampling system is provided for measuring analyte levels in the body fluid. The system may comprise of a housing having a transparent window; a cartridge in the housing; a plurality of penetrating member in the cartridge; a plurality of analyte detecting members mounted on the cartridge; wherein the window allows a user to see the cartridge within the housing, the window sized and positioned to show body fluid fill in the cartridge. In one embodiment, the window allows a user to see if they are successfully using the sampling system.

In one embodiment of the present invention, a device is provided for use in a body fluid sampling system for measuring analyte levels in the body fluid. The device comprises a cartridge; a plurality of penetrating member in said cartridge; and a plurality of analyte detecting members mounted on the cartridge, said detecting members mounted on an upper, outer surface of said cartridge and positioned to receive fluid flowing from a wound created by said penetrating member in the tissue. The device may have a wicking member that is coupled to each of said analyte detecting member and positioned to extend over at least a portion of a penetrating member exit chamber on said cartridge.

It should be understood that a wicking member may be coupled to each of said analyte detecting member and positioned near a penetrating member exit chamber on said cartridge. A wicking member may be coupled to each of said analyte detecting member and positioned to at least partially surround a penetrating member exit chamber on said cartridge. A wicking member may be coupled to each of said analyte detecting member and positioned to surround a penetrating member exit chamber on said cartridge, the wicking member defining one of the following: a circular opening, a square opening, or a rectangular opening. The analyte detecting member may comprise of a plurality reference electrodes, counter electrodes, working electrodes, wherein all of said reference electrodes are electrically coupled together, and only one set of counter and working electrodes can be active at any one time. Each of the analyte detecting member may comprise of at least one reference electrode, at least one working electrode, and at least one counter electrode. Each of the analyte detecting member may comprise of at least one reference electrode, at least one working electrode, and at least one counter electrode, wherein contact pads for each electrode is also on the top surface of the cartridge. The analyte detecting member may comprise of a plurality reference electrodes, counter electrodes, working electrodes, wherein all of said reference electrodes are electrically coupled together, and only one set of counter and working electrodes can be active at any one time. The cartridge may comprise of a radial disc with a plurality of cavities, each of said cavities holding one of said penetrating members. The cartridge may comprise of a radial disc with a plurality of cavities with openings on an upper surface of the cartridge, wherein each of the cavities holds one of said penetrating members, said analyte detecting member attached on the side of the cartridge with the cavity openings. The cartridge may comprise of a radial disc with a plurality of cavities with openings on an upper surface of the cartridge, wherein each of the cavities holds one of said penetrating members, said analyte detecting members attached on the side of the cartridge with the cavity openings, wherein electrical contact pads for the analyte detecting members also positioned on the side of the cartridge with the cavity openings.

In one embodiment of the present invention, an actuation device may comprise of a combined lancing and blood sample analysis device in a single disposable cartridge; wherein the cartridge is manufactured by allowing penetrating members to be pre-sterilized before assembling the analytical analyte detecting members on the cartridge, wherein the analyte detecting members are mounted on an exterior surface of a sealed cartridge containing a plurality of penetrating members in a sterile condition.

In yet another embodiment of the present invention, another actuation device may comprise of a combined lancing and blood sample analysis device in a single disposable cartridge; wherein the cartridge manufacture by allowing penetrating members to be pre-sterilized before assembling the analytical analyte detecting members on the cartridge, wherein the analyte detecting members are mounted on an exterior surface of a sealed cartridge containing a plurality of penetrating members in a sterile condition; and a second protective layer added to protect the analyte detecting members mounted on an outer surface of the sealed cartridge.

In a still further embodiment of the present invention, a method is provided for the manufacture of an actuation device. The method comprises providing a cartridge containing a plurality of penetrating members; sterilizing the cartridge and the penetrating members before assembling the analytical analyte detecting members on the cartridge, sealing the cartridge to form a sealed cartridge; mounting the analyte detecting members on an exterior surface of a sealed cartridge containing the plurality of penetrating members in a sterile condition; and adding a second protective layer to protect the analyte detecting members mounted on an outer surface of the sealed cartridge.

It should be understood that the cartridge may comprise of a radial disc with a plurality of cavities, each of said cavities holding one of said penetrating members. The cartridge may be sealed with a metallic foil. The analyte detecting members may be coupled to at least one reference electrode and at least one working electrode. The method may also include attaching a wicking member to each of the analyte detecting members to bring body fluid from a wound created on a patient to the analyte detecting member. The method may also include attaching a wicking member to each of the analyte detecting members to bring body fluid from a wound created on a patient to the analyte detecting member, said wicking member placed on an exterior surface of a sealed cartridge and positioned on the side of the cartridge with sealed cavity openings. A second foil layer may be included that covers the analyte detecting member and the second protective layer.

In another embodiment of the present invention, a body fluid sampling system is provided for measuring analyte levels in the body fluid. The system comprises a housing having a transparent window; a cartridge in said housing; a plurality of penetrating member in said cartridge; a plurality of analyte detecting members mounted on said cartridge; wherein the window allows a user to see the cartridge within the housing, said window sized and positioned to show body fluid fill in the cartridge.

It should be understood that a wicking member may be coupled to each of said analyte detecting member and positioned to extend over at least a portion of a penetrating member exit chamber on said cartridge. The entire housing may be made of a transparent material. The cartridge has markings visible through said window. The cartridge may have markings visible through said window, said marking indicating at least one of the following: number of penetrating members used, number of glucose tests used, number of unused penetrating members remaining, number of unused glucose tests remaining, color indicating whether it is time to change the cartridge, markings showing sufficient fluid fill, and/or the expiration date of the cartridge.

A further understanding of the nature and advantages of the invention will become apparent by reference to the remaining portions of the specification and drawings.

DESCRIPTION OF THE SPECIFIC EMBODIMENTS

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

Figure 1:
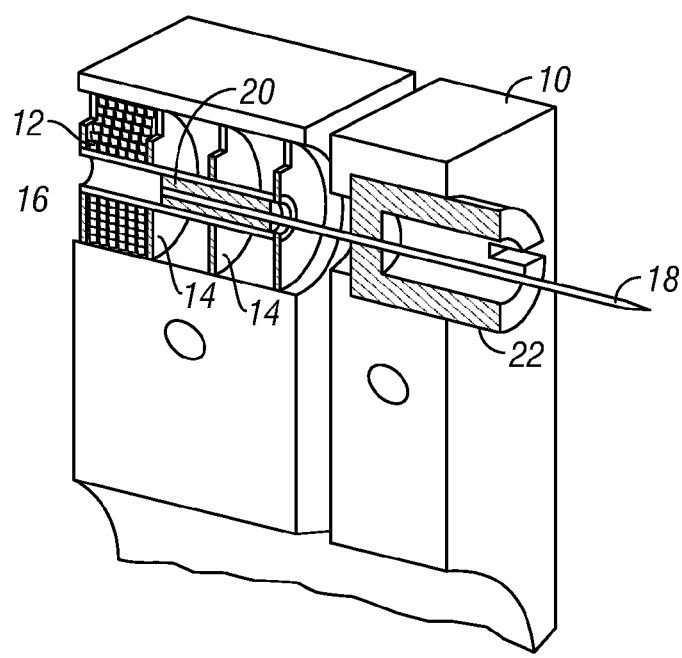
FIG. 1 illustrates an embodiment of a controllable force driver in the form of a cylindrical electric penetrating member driver using a coiled solenoid-type configuration.

The present invention may be used with a variety of different penetrating member drivers. It is contemplated that these penetrating member drivers may be spring based, solenoid based, magnetic driver based, nanomuscle based, or based on any other mechanism useful in moving a penetrating member along a path into tissue. It should be noted that the present invention is not limited by the type of driver used with the penetrating member feed mechanism. One suitable penetrating member driver for use with the present invention is shown in FIG. 1. This is an embodiment of a solenoid type electromagnetic driver that is capable of driving an iron core or slug mounted to the penetrating member assembly using a direct current (DC) power supply. The electromagnetic driver includes a driver coil pack that is divided into three separate coils along the path of the penetrating member, two end coils and a middle coil. Direct current is alternated to the coils to advance and retract the penetrating member. Although the driver coil pack is shown with three coils, any suitable number of coils may be used, for example, 4, 5, 6, 7 or more coils may be used.

Referring to the embodiment of FIG. 1, the stationary iron housing 10 may contain the driver coil pack with a first coil 12 flanked by iron spacers 14 which concentrate the magnetic flux at the inner diameter creating magnetic poles. The inner insulating housing 16 isolates the penetrating member 18 and iron core 20 from the coils and provides a smooth, low friction guide surface. The penetrating member guide 22 further centers the penetrating member 18 and iron core 20. The penetrating member 18 is protracted and retracted by alternating the current between the first coil 12, the middle coil, and the third coil to attract the iron core 20. Reversing the coil sequence and attracting the core and penetrating member back into the housing retracts the penetrating member. The penetrating member guide 22 also serves as a stop for the iron core 20 mounted to the penetrating member 18.

Figure 2A:
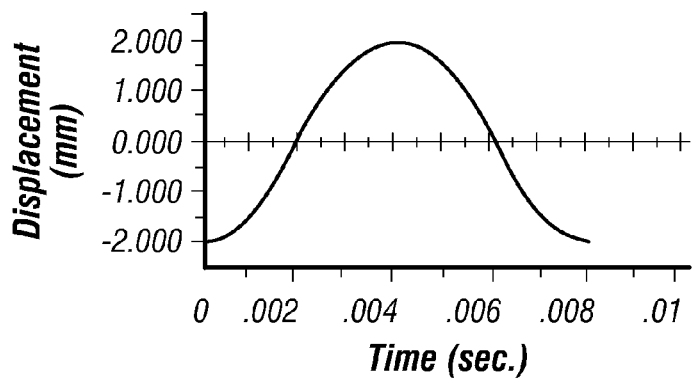
FIG. 2A illustrates a displacement over time profile of a penetrating member driven by a harmonic spring/mass system.
Figure 2B:
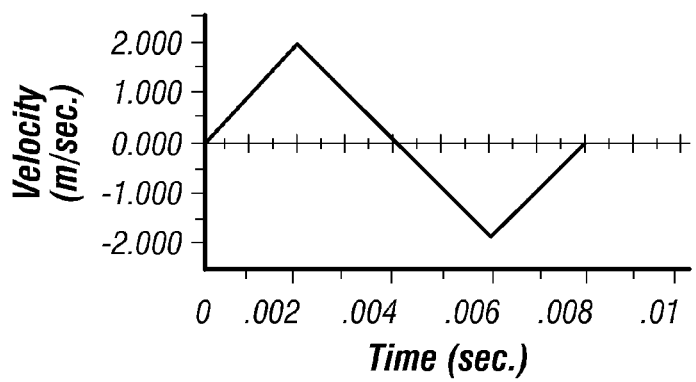
FIG. 2B illustrates the velocity over time profile of a penetrating member driver by a harmonic spring/mass system.
Figure 2C:
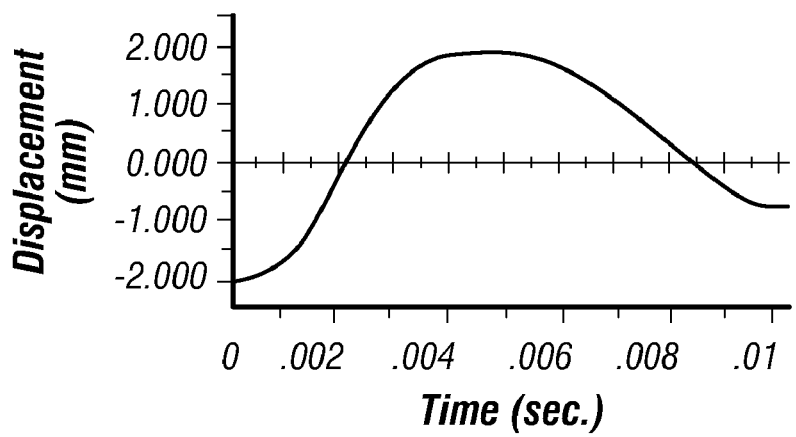
FIG. 2C illustrates a displacement over time profile of an embodiment of a controllable force driver.
Figure 2D:
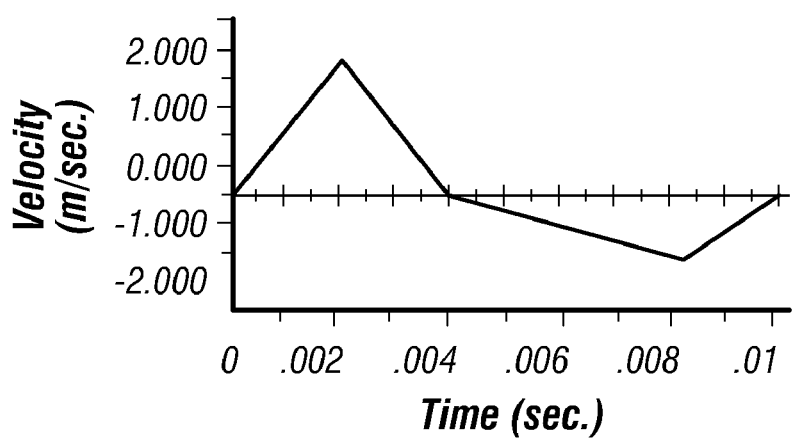
FIG. 2D illustrates a velocity over time profile of an embodiment of a controllable force driver.
Figure 3:
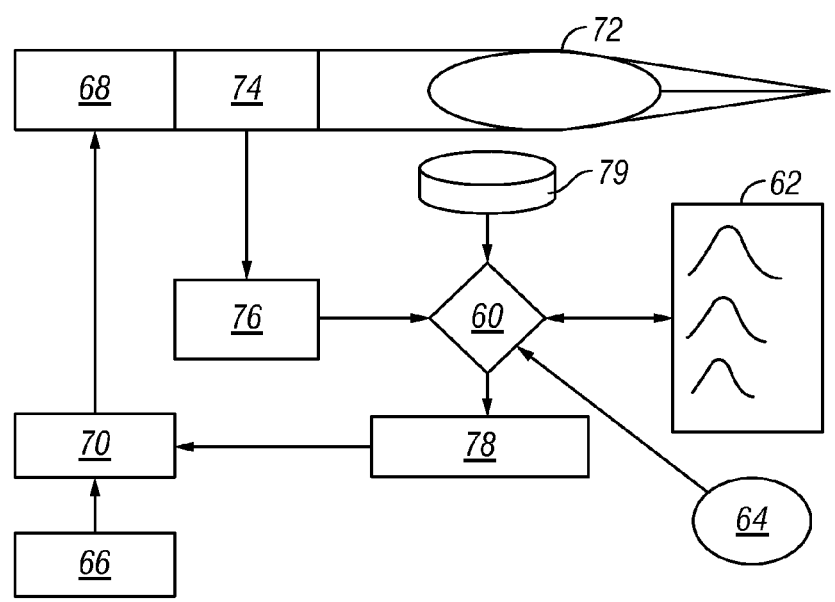
FIG. 3 is a diagrammatic view illustrating a controlled feed-back loop.

As discussed above, tissue penetration devices which employ spring or cam driving methods have a symmetrical or nearly symmetrical actuation displacement and velocity profiles on the advancement and retraction of the penetrating member as shown in FIGS. 2 and 3. In most of the available lancet devices, once the launch is initiated, the stored energy determines the velocity profile until the energy is dissipated. Controlling impact, retraction velocity, and dwell time of the penetrating member within the tissue can be useful in order to achieve a high success rate while accommodating variations in skin properties and minimize pain. Advantages can be achieved by taking into account of the fact that tissue dwell time is related to the amount of skin deformation as the penetrating member tries to puncture the surface of the skin and variance in skin deformation from patient to patient based on skin hydration.

In this embodiment, the ability to control velocity and depth of penetration may be achieved by use of a controllable force driver where feedback is an integral part of driver control. Such drivers can control either metal or polymeric penetrating members or any other type of tissue penetration element. The dynamic control of such a driver is illustrated in Figure. 2C which illustrates an embodiment of a controlled displacement profile and FIG. 2D which illustrates an embodiment of a the controlled velocity profile. These are compared to FIGS. 2A and 2B, which illustrate embodiments of displacement and velocity profiles, respectively, of a harmonic spring/mass powered driver. Reduced pain can be achieved by using impact velocities of greater than about 2 m/s entry of a tissue penetrating element, such as a lancet, into tissue. Other suitable embodiments of the penetrating member driver are described in commonly assigned, U.S. patent application Ser. No. 10/127,395, filed Apr. 19, 2002, now U.S. Pat. No. 7,025,774, and previously incorporated herein.

FIG. 3 illustrates the operation of a feedback loop using a processor 60. The processor 60 stores profiles 62 in non-volatile memory. A user inputs information 64 about the desired circumstances or parameters for a lancing event. The processor 60 selects a driver profile 62 from a set of alternative driver profiles that have been preprogrammed in the processor 60 based on typical or desired tissue penetration device performance determined through testing at the factory or as programmed in by the operator. The processor 60 may customize by either scaling or modifying the profile based on additional user input information 64. Once the processor has chosen and customized the profile, the processor 60 is ready to modulate the power from the power supply 66 to the penetrating member driver 68 through an amplifier 70. The processor 60 may measure the location of the penetrating member 72 using a position sensing mechanism 74 through an analog to digital converter 76 linear encoder or other such transducer. Examples of position sensing mechanisms have been described in the embodiments above and may be found in the specification for commonly assigned, copending U.S. patent application Ser. No. 10/127,395, filed Apr. 19, 2002 and previously incorporated herein. The processor 60 calculates the movement of the penetrating member by comparing the actual profile of the penetrating member to the predetermined profile. The processor 60 modulates the power to the penetrating member driver 68 through a signal generator 78, which may control the amplifier 70 so that the actual velocity profile of the penetrating member does not exceed the predetermined profile by more than a preset error limit. The error limit is the accuracy in the control of the penetrating member.

After the lancing event, the processor 60 can allow the user to rank the results of the lancing event. The processor 60 stores these results and constructs a database 80 for the individual user. Using the database 79, the processor 60 calculates the profile traits such as degree of painlessness, success rate, and blood volume for various profiles 62 depending on user input information 64 to optimize the profile to the individual user for subsequent lancing cycles. These profile traits depend on the characteristic phases of penetrating member advancement and retraction. The processor 60 uses these calculations to optimize profiles 62 for each user. In addition to user input information 64, an internal clock allows storage in the database 79 of information such as the time of day to generate a time stamp for the lancing event and the time between lancing events to anticipate the user's diurnal needs. The database stores information and statistics for each user and each profile that particular user uses.

In addition to varying the profiles, the processor 60 can be used to calculate the appropriate penetrating member diameter and geometry suitable to realize the blood volume required by the user. For example, if the user requires about 1-5 microliter volume of blood, the processor 60 may select a 200 micron diameter penetrating member to achieve these results. For each class of lancet, both diameter and lancet tip geometry, is stored in the processor 60 to correspond with upper and lower limits of attainable blood volume based on the predetermined displacement and velocity profiles.

The lancing device is capable of prompting the user for information at the beginning and the end of the lancing event to more adequately suit the user. The goal is to either change to a different profile or modify an existing profile. Once the profile is set, the force driving the penetrating member is varied during advancement and retraction to follow the profile. The method of lancing using the lancing device comprises selecting a profile, lancing according to the selected profile, determining lancing profile traits for each characteristic phase of the lancing cycle, and optimizing profile traits for subsequent lancing events.

Figure 4:
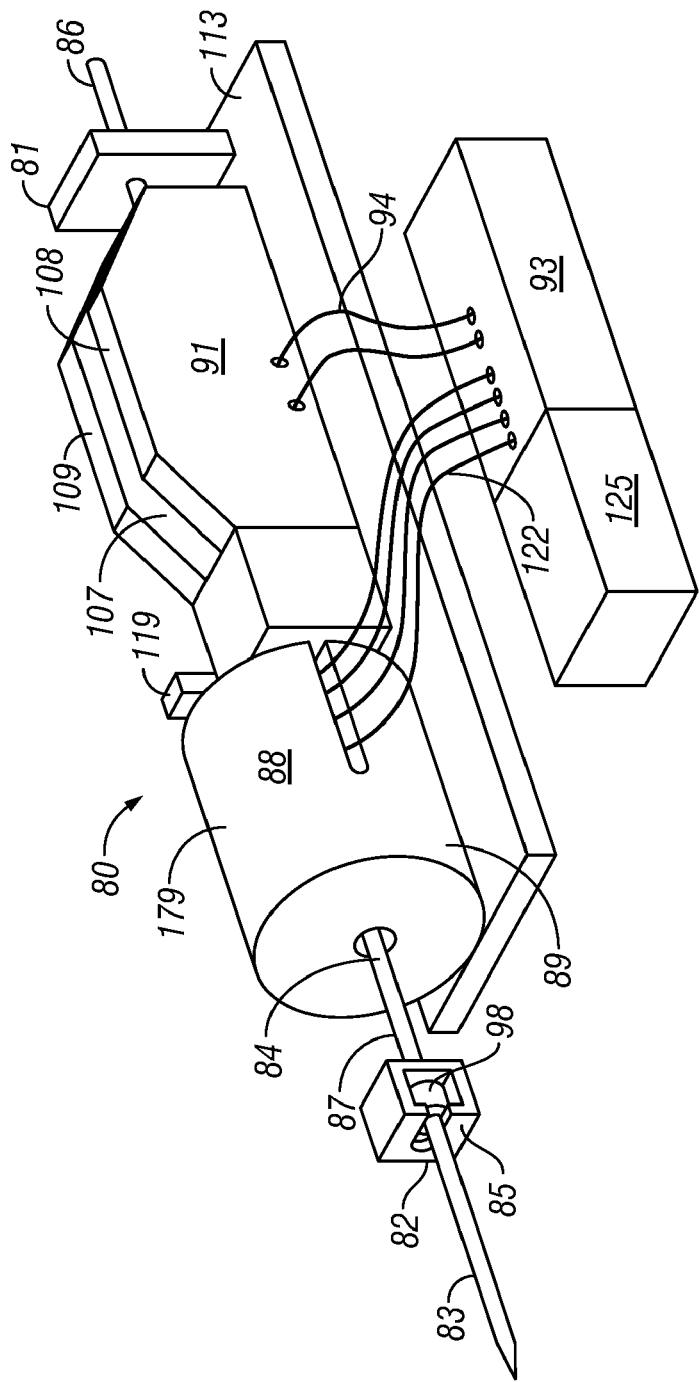
FIG. 4 is a perspective view of a tissue penetration device having features of the invention.

FIG. 4 illustrates an embodiment of a tissue penetration device, more specifically, a lancing device 80 that includes a controllable driver 179 coupled to a tissue penetration element. The lancing device 80 has a proximal end 81 and a distal end 82. At the distal end 82 is the tissue penetration element in the form of a penetrating member 83, which is coupled to an elongate coupler shaft 84 by a drive coupler 85. The elongate coupler shaft 84 has a proximal end 86 and a distal end 87. A driver coil pack 88 is disposed about the elongate coupler shaft 84 proximal of the penetrating member 83. A position sensor 91 is disposed about a proximal portion 92 of the elongate coupler shaft 84 and an electrical conductor 94 electrically couples a processor 93 to the position sensor 91. The elongate coupler shaft 84 driven by the driver coil pack 88 controlled by the position sensor 91 and processor 93 form the controllable driver, specifically, a controllable electromagnetic driver.

Figure 5:
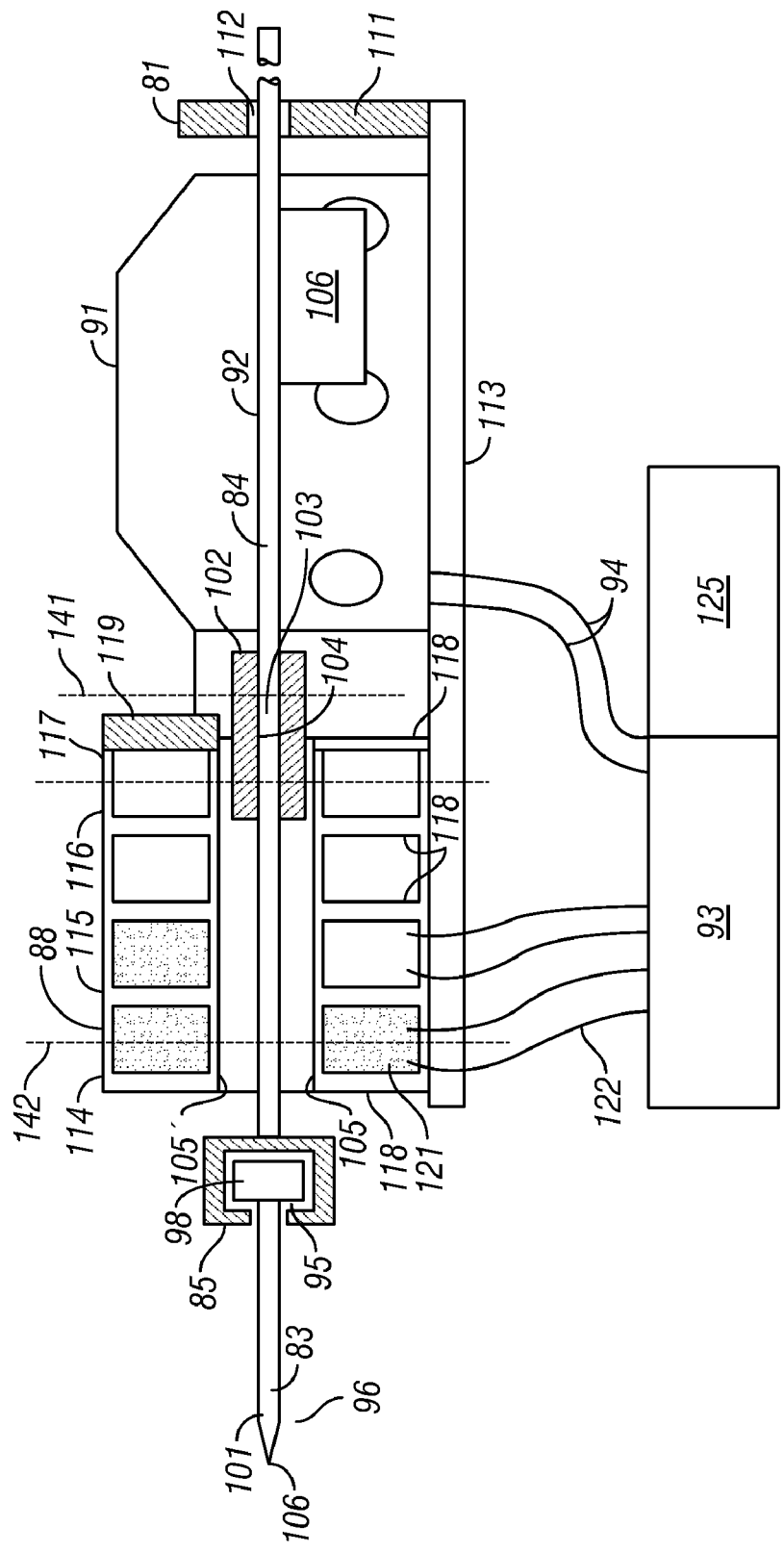
FIG. 5 is an elevation view in partial longitudinal section of the tissue penetration device of FIG. 4.

Referring to FIG. 5, the lancing device 80 can be seen in more detail, in partial longitudinal section. The penetrating member 83 has a proximal end 95 and a distal end 96 with a sharpened point at the distal end 96 of the penetrating member 83 and a drive head 98 disposed at the proximal end 95 of the penetrating member 83. A penetrating member shaft 201 is disposed between the drive head 98 and the sharpened point 97. The penetrating member shaft 201 may be comprised of stainless steel, or any other suitable material or alloy and have a transverse dimension of about 0.1 to about 0.4 mm. The penetrating member shaft may have a length of about 3 mm to about 50 mm, specifically, about 15 mm to about 20 mm. The drive head 98 of the penetrating member 83 is an enlarged portion having a transverse dimension greater than a transverse dimension of the penetrating member shaft 201 distal of the drive head 98. This configuration allows the drive head 98 to be mechanically captured by the drive coupler 85. The drive head 98 may have a transverse dimension of about 0.5 to about 2 mm.

A magnetic member 102 is secured to the elongate coupler shaft 84 proximal of the drive coupler 85 on a distal portion 203 of the elongate coupler shaft 84. The magnetic member 102 is a substantially cylindrical piece of magnetic material having an axial lumen 204 extending the length of the magnetic member 102. The magnetic member 102 has an outer transverse dimension that allows the magnetic member 102 to slide easily within an axial lumen 105 of a low friction, possibly lubricious, polymer guide tube 105' disposed within the driver coil pack 88. The magnetic member 102 may have an outer transverse dimension of about 1.0 to about 5.0 mm, specifically, about 2.3 to about 2.5 mm. The magnetic member 102 may have a length of about 3.0 to about 5.0 mm, specifically, about 4.7 to about 4.9 mm. The magnetic member 102 can be made from a variety of magnetic materials including ferrous metals such as ferrous steel, iron, ferrite, or the like. The magnetic member 102 may be secured to the distal portion 203 of the elongate coupler shaft 84 by a variety of methods including adhesive or epoxy bonding, welding, crimping or any other suitable method.

Proximal of the magnetic member 102, an optical encoder flag 206 is secured to the elongate coupler shaft 84. The optical encoder flag 206 is configured to move within a slot 107 in the position sensor 91. The slot 107 of the position sensor 91 is formed between a first body portion 108 and a second body portion 109 of the position sensor 91. The slot 107 may have separation width of about 1.5 to about 2.0 mm. The optical encoder flag 206 can have a length of about 14 to about 18 mm, a width of about 3 to about 5 mm and a thickness of about 0.04 to about 0.06 mm.

The optical encoder flag 206 interacts with various optical beams generated by LEDs disposed on or in the position sensor body portions 108 and 109 in a predetermined manner. The interaction of the optical beams generated by the LEDs of the position sensor 91 generates a signal that indicates the longitudinal position of the optical flag 206 relative to the position sensor 91 with a substantially high degree of resolution. The resolution of the position sensor 91 may be about 200 to about 400 cycles per inch, specifically, about 350 to about 370 cycles per inch. The position sensor 91 may have a speed response time (position/time resolution) of 0 to about 120,000 Hz, where one dark and light stripe of the flag constitutes one Hertz, or cycle per second. The position of the optical encoder flag 206 relative to the magnetic member 102, driver coil pack 88 and position sensor 91 is such that the optical encoder 91 can provide precise positional information about the penetrating member 83 over the entire length of the penetrating member's power stroke.

An optical encoder that is suitable for the position sensor 91 is a linear optical incremental encoder, model HEDS 9200, manufactured by Agilent Technologies. The model HEDS 9200 may have a length of about 20 to about 30 mm, a width of about 8 to about 12 mm, and a height of about 9 to about 11 mm. Although the position sensor 91 illustrated is a linear optical incremental encoder, other suitable position sensor embodiments could be used, provided they posses the requisite positional resolution and time response. The HEDS 9200 is a two channel device where the channels are 90 degrees out of phase with each other. This results in a resolution of four times the basic cycle of the flag. These quadrature outputs make it possible for the processor to determine the direction of penetrating member travel. Other suitable position sensors include capacitive encoders, analog reflective sensors, such as the reflective position sensor discussed above, and the like.

A coupler shaft guide 111 is disposed towards the proximal end 81 of the lancing device 80. The guide 111 has a guide lumen 112 disposed in the guide 111 to slidingly accept the proximal portion 92 of the elongate coupler shaft 84. The guide 111 keeps the elongate coupler shaft 84 centered horizontally and vertically in the slot 102 of the optical encoder 91.

The driver coil pack 88, position sensor 91 and coupler shaft guide 111 are all secured to a base 113. The base 113 is longitudinally coextensive with the driver coil pack 88, position sensor 91 and coupler shaft guide 111. The base 113 can take the form of a rectangular piece of metal or polymer, or may be a more elaborate housing with recesses, which are configured to accept the various components of the lancing device 80.

As discussed above, the magnetic member 102 is configured to slide within an axial lumen 105 of the driver coil pack 88. The driver coil pack 88 includes a most distal first coil 114, a second coil 115, which is axially disposed between the first coil 114 and a third coil 116, and a proximal-most fourth coil 117. Each of the first coil 114, second coil 115, third coil 116 and fourth coil 117 has an axial lumen. The axial lumens of the first through fourth coils are configured to be coaxial with the axial lumens of the other coils and together form the axial lumen 105 of the driver coil pack 88 as a whole. Axially adjacent each of the coils 114-117 is a magnetic disc or washer 118 that augments completion of the magnetic circuit of the coils 114-117 during a lancing cycle of the device 80. The magnetic washers 118 of the embodiment of FIG. 5 are made of ferrous steel but could be made of any other suitable magnetic material, such as iron or ferrite. The outer shell 89 of the driver coil pack 88 is also made of iron or steel to complete the magnetic path around the coils and between the washers 118. The magnetic washers 118 have an outer diameter commensurate with an outer diameter of the driver coil pack 88 of about 4.0 to about 8.0 mm. The magnetic washers 118 have an axial thickness of about 0.05, to about 0.4 mm, specifically, about 0.15 to about 0.25 mm.

Wrapping or winding an elongate electrical conductor 121 about an axial lumen until a sufficient number of windings have been achieved forms the coils 114-117. The elongate electrical conductor 121 is generally an insulated solid copper wire with a small outer transverse dimension of about 0.06 mm to about 0.88 mm, specifically, about 0.3 mm to about 0.5 mm. In one embodiment, 32 gauge copper wire is used for the coils 114-117. The number of windings for each of the coils 114-117 of the driver pack 88 may vary with the size of the coil, but for some embodiments each coil 114-117 may have about 30 to about 80 turns, specifically, about 50 to about 60 turns. Each coil 114-117 can have an axial length of about 1.0 to about 3.0 mm, specifically, about 1.8 to about 2.0 mm. Each coil 114-117 can have an outer transverse dimension or diameter of about 4.0, to about 2.0 mm, specifically, about 9.0 to about 12.0 mm. The axial lumen 105 can have a transverse dimension of about 1.0 to about 3.0 mm.

It may be advantageous in some driver coil 88 embodiments to replace one or more of the coils with permanent magnets, which produce a magnetic field similar to that of the coils when the coils are activated. In particular, it may be desirable in some embodiments to replace the second coil 115, the third coil 116 or both with permanent magnets. In addition, it may be advantageous to position a permanent magnet at or near the proximal end of the coil driver pack in order to provide fixed magnet zeroing function for the magnetic member (Adams magnetic Products 23A0002 flexible magnet material (800) 747-7543).

Figure 6B:
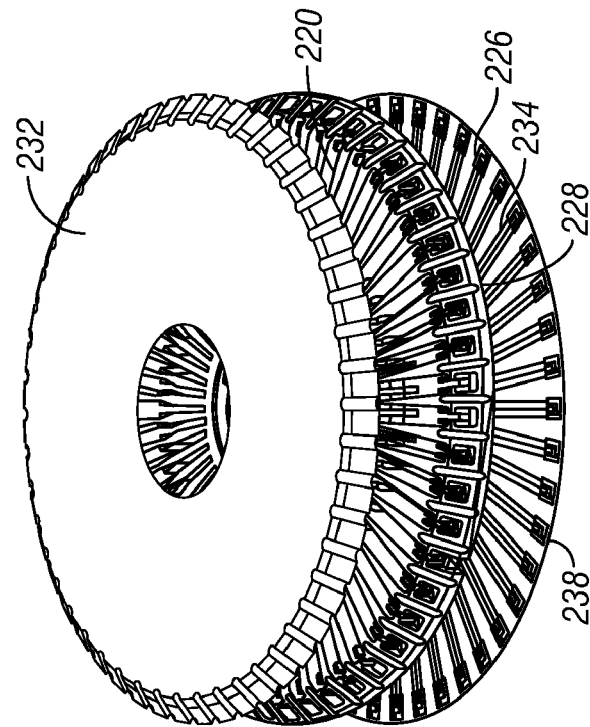
FIG. 6B shows one embodiment of a cartridge according to the present invention.
Figure 6A:
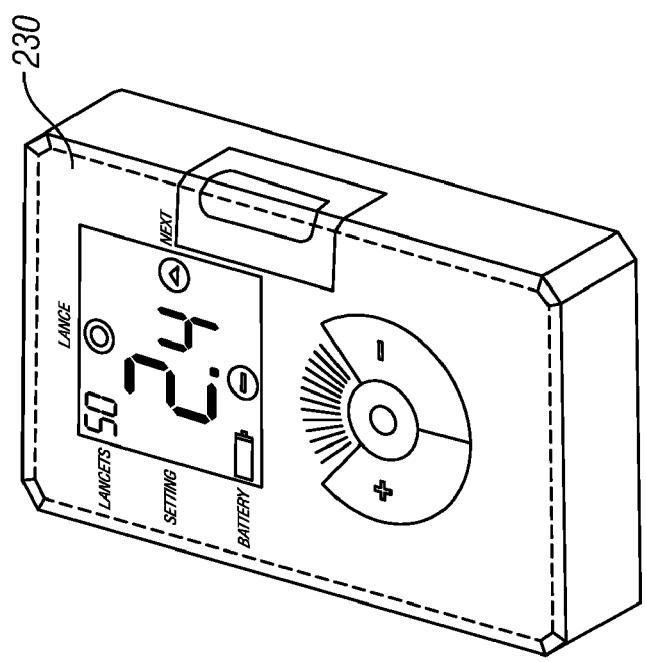
FIG. 6A shows one embodiment of a device which may use the present invention.

Referring now to FIGS. 6A and 6B, yet another embodiment of the present invention will now be described. It should be understood that this embodiment may be adapted for use with devices described in commonly assigned copending U.S. patent application Ser. No. 10/323,624 filed Dec. 18, 2002. FIG. 6A shows a device that may optionally use a cartridge as shown in FIG. 6B. FIG. 6B shows a radial cartridge 220. The cartridge 220 may optionally include a sterility barrier 232 and a substrate 238 having a plurality of analyte detecting members 226. In this embodiment, the cartridge 220 is designed so that blood will enter the fluid chamber 228 and be held there for analysis.

FIG. 6B shows the radial cartridge 220 may optionally be used with a lancing device 230. The radial cartridge 220 may optionally be sealed with a sterility barrier 232 and be coupled to analyte detecting members mounted on a substrate 234. A suitable device is described in commonly assigned, U.S. patent application Ser. No. 10/429,196, now U.S. Pat. No. 7,297,151, fully incorporated herein by reference for all purposes.

Figure 7:
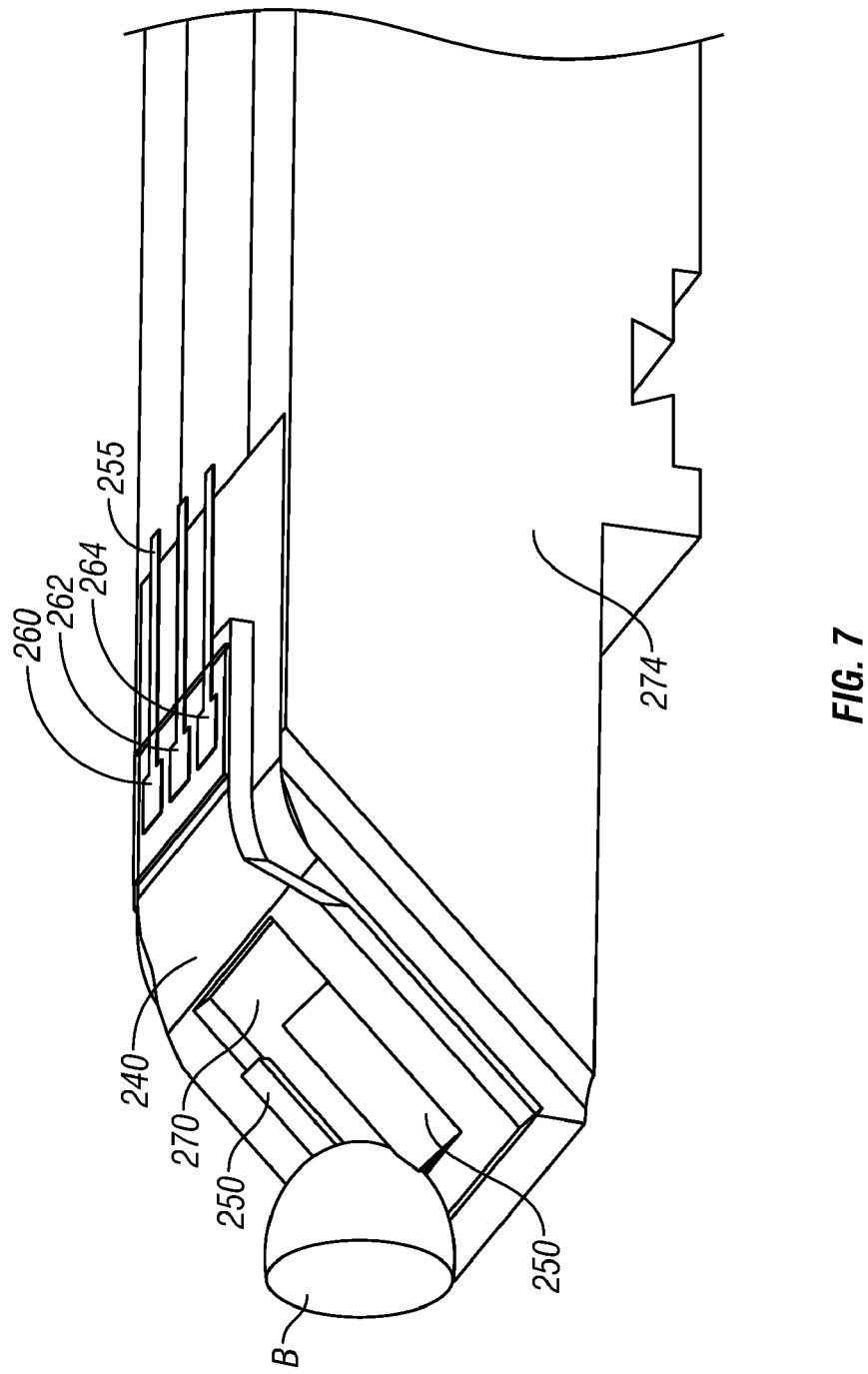
FIGS. 7 and 8 show one embodiment of the present invention.

In an embodiment of the present invention as seen in FIG. 7, an adhesively mounted analyte detecting member disc is added to the top of the present radial disc described in the U.S. patent application Ser. No. 10/323,624 and the member 226 on the disc (seen in FIG. 6B) may optionally be removed and replaced by the adhesively mounted members. Some embodiments may retain the members 226 on the underside. Some embodiments may only retain the conductive members on the underside. In the present embodiment, as a nonlimiting example, the analyte detecting member disc may comprise:

1. An adhesive film, or some other mounting means.
2. A non-conductive substrate such as but not limited to plastic.
3. Printed-on carbon paste conductors connecting the active chemistry areas with contact pads for communication with analysis electronics. One feature of the present embodiment is the use of perforations in the substrate that allow the conductive carbon paste to print through to the other side of the substrate. Traces may be printed on both sides of the substrate allowing three electrodes to be spaced down the narrow separators between adjacent chambers.
4. Analytical chemistry may be printed onto pads at the end of the carbon paste conductors.
5. A protective gel may be printed over the chemistry.
6. A wicking mesh may be laminated to the substrate, covering the chemistry and gel, and surrounding the lancet launch area.
7. A protective covering (plastic/foil/paper) may be laminated to the wicking mesh. This cover may be cut away to avoid interfering with the operation of the actuator punch, or the cover may be designed to be pierced by the punch at the same time the lancet chamber is opened. The protective outer cover is not shown in the figures.

Figure 8:
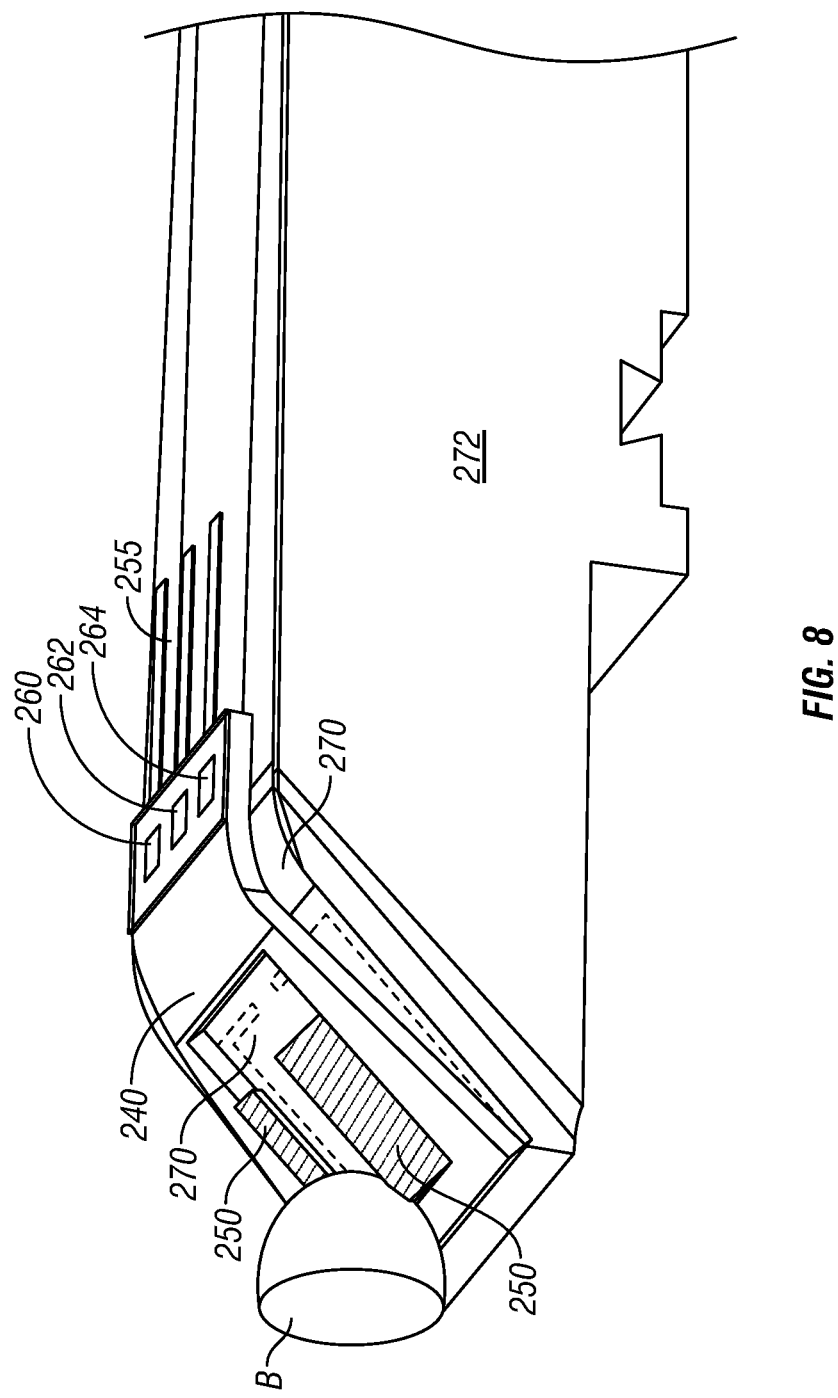

Referring to FIGS. 7 and 8, the wicking material 240 is shown with flaps 250 that are free standing, or fold out when the penetrating member chamber is opened. The flaps 250 are free to move out of the way of the chamber punch (as described in U.S. patent application Ser. No. 10/323,624) so as to not interfere with its operation, yet spring back to provide good contact with the blood drop B. The flaps 250 are trimmed or sized short enough that they do not touch the lancet as it moves into the finger. FIG. 7 also shows an alternate location for the analyte detecting member electrodes on top of the mesh. FIG. 7 shows that the counter electrode 260, working electrode 262, and reference electrode 264 may be positioned as shown. In one embodiment, the electrodes may optionally be printed onto the underside of an outer protective covering (not shown). The conductive lines 255 may extend back to make electrical contact with contact pads connected to a metering device. The line drawing of FIG. 8 shows some of the features discussed with regards to FIG. 7. It should be understood that FIGS. 7 and 8 are cutaway views of one section of a radial disc cartridge similar to a cartridge shown in FIG. 6. In one embodiment, a protective layer 270 may be included to maintain the penetrating member in the cartridge 272 in a sterile condition.

Referring to FIG. 9A, one embodiment of the present invention will be described. The substrate 280 is shown cut off near the electrical contacts. One embodiment would extend the substrate 280 toward the center of the disc to provide a larger disc for handling and strength (FIG. 10 shows a larger substrate 280). The carbon paste conductors 255 are shown terminating in contact pads 282 distributed radially within each segment. Larger contact pads can be achieved by spreading the contact pads across the segment area, and by elongating the pads. As a nonlimiting example, the wicking mesh 240 as shown has a gross volume of 0.992 µl. The volume of strands in the mesh reduces the actual wicking volume of blood.

In various embodiments, analyte detecting member determines a concentration of an analyte in a body fluid using a sample that does not exceed a volume of, 1 µL of a body fluid disposed in mesh 240, 0.75 µL, of a body fluid disposed in mesh 240, 0.5 µL of a body fluid disposed in mesh 240, 0.25 µL of a body fluid disposed in 240, 0.1 µL of a body fluid disposed in mesh 240, and the like. For example and not by way of limitation, the mesh may be of a size so that so that volumes greater than the above may be used, but the analyte detecting member can obtain an analyte reading using the amounts of fluid described above.

Figure 9:
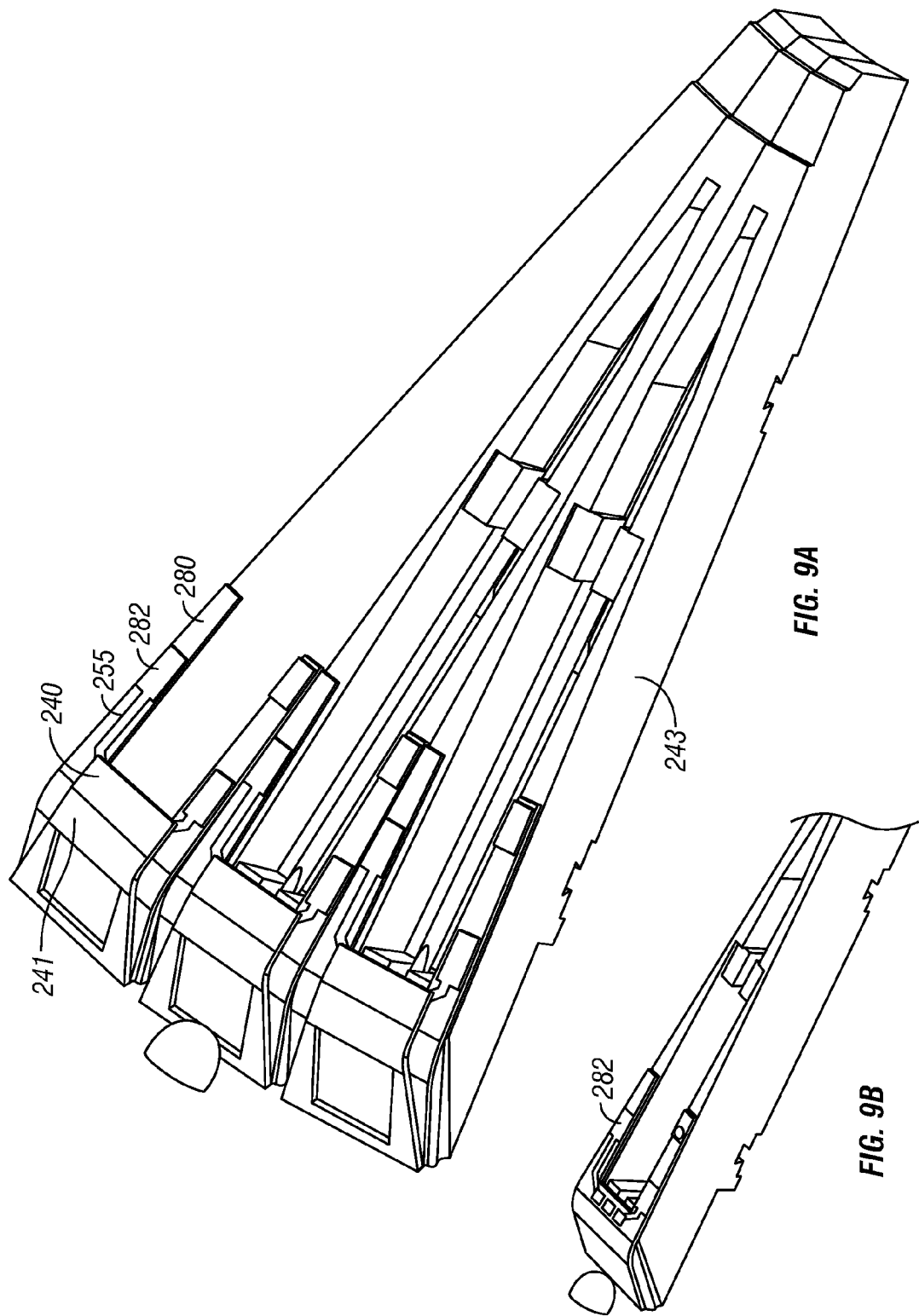
FIGS. 9A and 9B show top down views of a portion of a cartridge according to the present invention.
Figure 10:
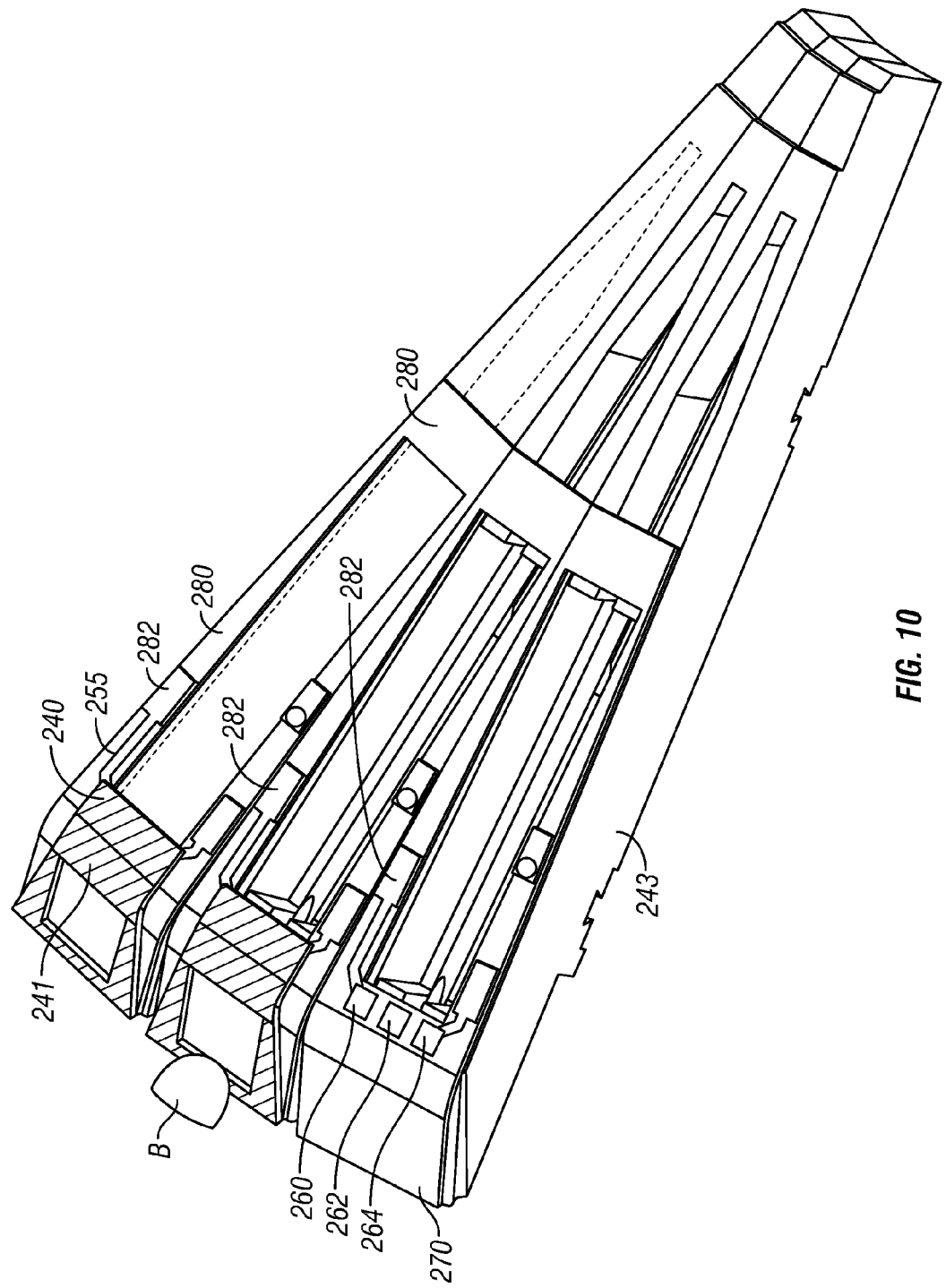
FIG. 10 shows another view of one embodiment of the present invention.

The embodiment in FIGS. 9A and 9B also show that in some embodiments, an additional foil may be applied to seal the analyte detecting members. The punch can open both seals. FIG. 9A also shows that the plastic substrate for the analyte detecting member may also extend to the inner diameter. The wicking member 240 may also have a segmented portion 241 that folds to sloped surface of the cartridge and attaches adhesively. The solid disk portion 243 may be adhesively applied to the disc. FIG. 9A also shows that the center contact feeds through substrate to back trace, then feeds through to contact pad. The trace is insulated by the adhesive layer. As seen in FIG. 9, it should be understood that the penetrating member exit chamber on the cartridge may be covered by the wicking member with one of the following: a circular opening, a square opening, a rectangular opening, a polygonal opening, or an oval opening to allow a penetrating member to pass through. Some embodiments may have no opening.

FIG. 9B shows a view with the layer 240 removed to show details of the electrodes and electrical leads underneath the layer 240.

In FIGS. 7-10, the analyte detecting member assembly may be fabricated as a flat disc that is registered to the sealed and sterilized lancet disc, and adhesively mounted to the protective foil. The wicking area 240 of each analyte detecting member assembly may be cut into a separate finger that is folded around the edge of the disc and adhered to the sloping outer surface. The conductive traces do not bend around the curve at the edge of the disc.

In some embodiments, it is desirable that a protective covering (not shown) that may used over the wicking material 240 not block access of the blood to the edges of the wicking material 240 after the covering is pierced and folded by the punch.

Figure 11:
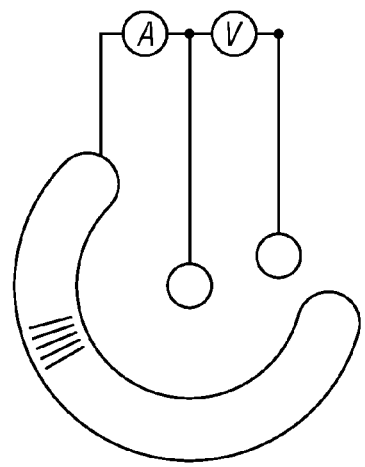
FIGS. 11 and 12 show configurations of electrodes and electrical leads according to the present invention.
Figure 12:
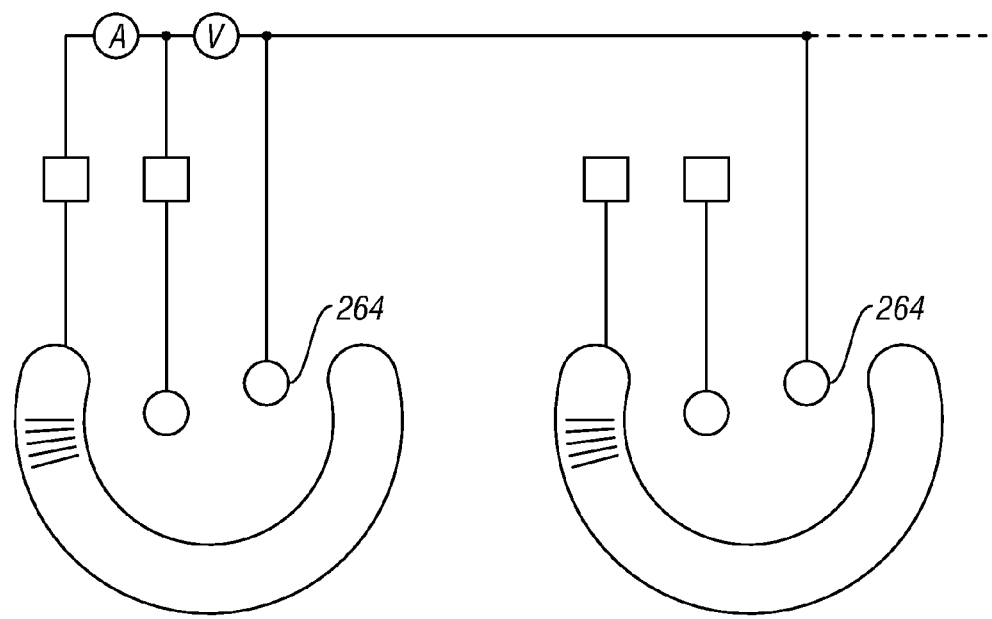

Referring to FIG. 11, the first illustration describes present technology analysis cells using a counter electrode, a working electrode, and a reference electrode. In one embodiment of the present invention as seen in FIG. 12, contact fingers or pads 280 in the actuating device connect to the counter and working electrodes when those particular electrodes in the "working" cell that are associated with the "active" penetrating member on the cartridge. Since contact with the counter and working electrodes of all of the other cells is broken until moved into position, it is possible to connect all of the reference electrodes 264 together without affecting the working circuit. This allows the disc design to use a single central contact for the reference electrodes 264, simplifying the arrangement of the two remaining contacts. Thus, in a multiple cell configuration, contacts connect the working and counter electrodes only when they are in the correct position. In this embodiment, when voltage is applied to all reference electrodes, only the current in the "working" cell is measured. A single central electrode does not need to make and break contact, and can have minimal sliding between contact and wiper. In some embodiments, it may even be possible to use the surface of the penetrating member protective foil as the reference electrode contact.

Figure 13:
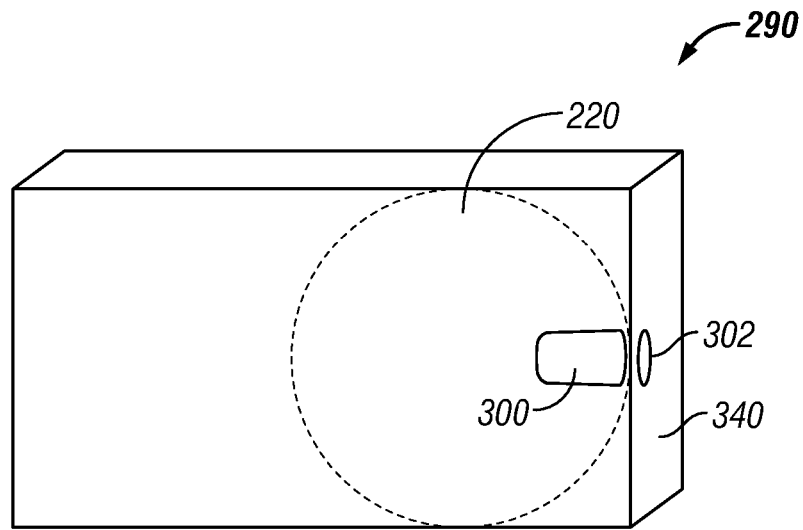
FIGS. 13 and 14 show one embodiment of the present invention with a window on the housing.
Figure 14:
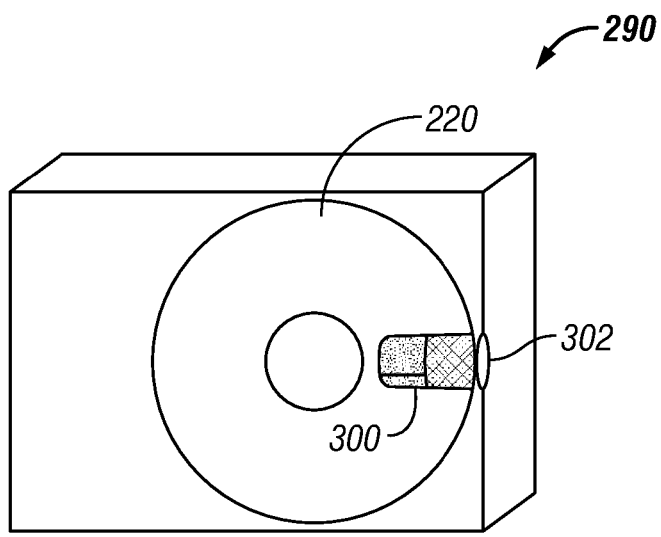

Referring now to FIGS. 13 and 14, in one embodiment of an integrated sampling device 290, an optically clear window 300 on the side of housing capable of showing the cartridge 220 inside can allow the user to assess whether the blood sample has been obtained for analysis in the analyte detecting member. The window 300, in some embodiments, is located near a penetrating member exit port 302. If it has not been obtained, alternate methods to achieve analysis of the blood via the wound generated by the lancing may be used. In some embodiments, the window 300 extends on the underside all the way to the edge of the underside closest to the penetrating member exit port. This allows the user to see the penetrating member exit from the underside. The cartridge 220 inside (and specifically the fluid pathway to the analyte detecting member or the member itself) could be illuminated by the ambient light or by the same element that is used for the guiding light feature discussed in U.S. patent application (attorney docket no. 38187-2657). A color shield filter may be used to disguise the blood for user preference. A convex lens (not shown) may be used and mounted on the window 300 to increase the size of the sensor area for easier reference to the user. In some alternative embodiments, a cutout is used instead of a window.

Figure 15A:
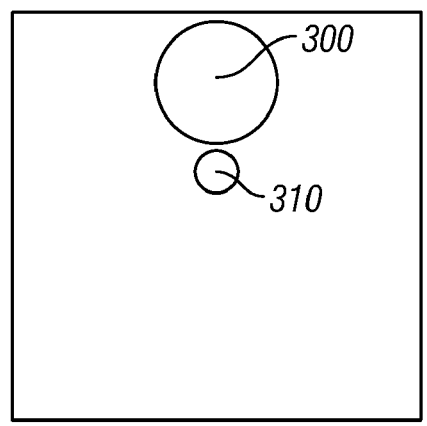
FIGS. 15A through 15C show other embodiments the present invention with a window on the housing.
Figure 15B:
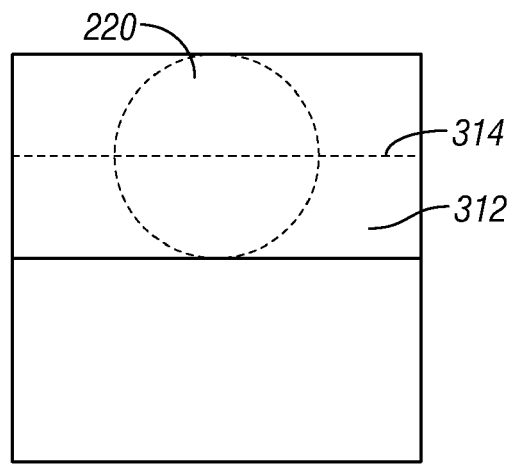
Figure 15C:
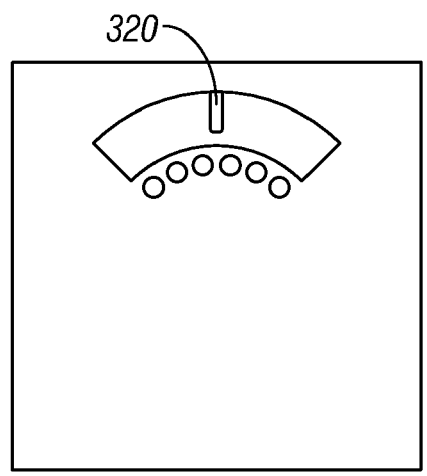
Figure 16:
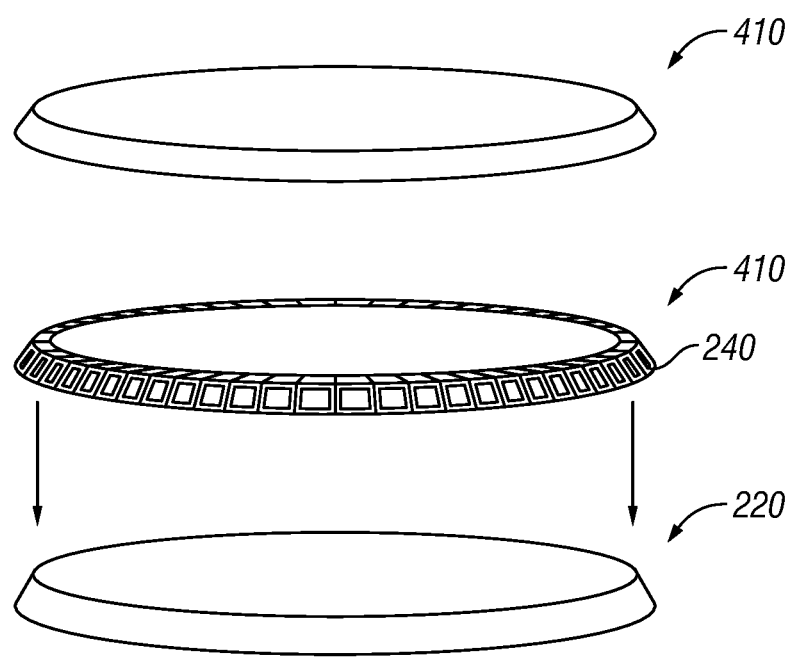
FIG. 16 shows yet another embodiment of the present invention.

Referring now to FIGS. 15A-15C, a plurality of window or cutout shapes may be used. FIG. 15A shows two windows 300 and 310. The smaller window 310 may be used to read writing or color or codes on the cartridge. FIG. 15B shows that half the underside may be transparent as indicated by window 312. In some embodiments, the window may be not be as large, as indicated by line 314, where only half of the cartridge 220 is visible. FIG. 15C shows a still further embodiment. Each cartridge may also have a fill indicator where filling the entire chamber will cause the area 320 on the cartridge to be colored.

If a visible light photometric sensor is used, the signal light may be used as a dual-purpose reference for the user. A one-way filter may be used to prevent ambient light pollution introducing noise to the sensor.

In an indexing system, the invention may also provide physical reference to the user that the next module of lancet and sensor needs to be advanced before the next lancing and sampling event may occur.

It should be understood that in some embodiments, the window is sized and extends to the penetrating member exit port so that a user may see the penetrating member contact the tissue or skin. Some embodiments may have the entire or substantially all of the underside transparent. Other embodiments may have the surface 340 or at least a portion of it transparent. Some embodiments will have the entire housing transparent. They may also be colored transparent material used to provide aesthetics to the device.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). With any of the above embodiments, the penetrating members may be a bare penetrating member during launch. With any of the above embodiments, the penetrating members may be bare penetrating members prior to launch as this may allow for significantly tighter densities of penetrating members. In some embodiments, the penetrating members may be bent, curved, textured, shaped, or otherwise treated at a proximal end or area to facilitate handling by an actuator. The penetrating member may be configured to have a notch or groove to facilitate coupling to a gripper. The notch or groove may be formed along an elongate portion of the penetrating member. With any of the above embodiments, the cavity may be on the bottom or the top of the cartridge, with the gripper on the other side. In some embodiments, analyte detecting members may be printed on the top, bottom, or side of the cavities. The front end of the cartridge maybe in contact with a user during lancing. The same driver may be used for advancing and retraction of the penetrating member. The penetrating member may have a diameters and length suitable for obtaining the blood volumes described herein. The penetrating member driver may also be in substantially the same plane as the cartridge. The driver may use a through hole or other opening to engage a proximal end of a penetrating member to actuate the penetrating member along a path into and out of the tissue. For any of the above embodiments, the individual wicking members 240 may be attached to a ring 400 and coupled to the disc 220. A second foil layer 410 may be positioned over the ring 400. It should understood that any of the inventions herein may be used in conjunction with devices disclosed in U.S. Pat. Nos. 7,025,774, 7,198,606 and 7,297,151.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications, patents, and patent applications mentioned herein are incorporated herein by reference to disclose and describe the structures and/or methods in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of manufacturing an actuation device, said method comprising:
    providing a cartridge containing a plurality of penetrating members;
    sterilizing the cartridge and the penetrating members before assembling the analytical analyte detecting members on the cartridge,
    sealing the cartridge to form a sealed cartridge;
    mounting the analyte detecting members on an exterior surface of a sealed cartridge containing the plurality of penetrating members in a sterile condition; and
    adding a second protective layer to protect the analyte detecting members mounted on an outer surface of the sealed cartridge.

2. The method of claim 1 wherein the cartridge comprises a radial disc with a plurality of cavities, each of said cavities holding one of said penetrating members.

3. The method of claim 1 wherein the cartridge is sealed with a metallic foil.

4. The method of claim 1 wherein analyte detecting members are coupled to at least one reference electrode and at least one working electrode.

5. The method of claim 1 further comprising attaching a wicking member to each of the analyte detecting members to bring body fluid from a wound created on a patient to the analyte detecting member.

6. The method of claim 1 further comprising attaching a wicking member to each of the analyte detecting members to bring body fluid from a wound created on a patient to the analyte detecting member, said wicking member placed on an exterior surface of a sealed cartridge and positioned on the side of the cartridge with sealed cavity openings.

7. The method of claim 1 wherein a second foil layer covers the analyte detecting member and the second protective layer.

* * * * *